US011064946B2

(12) United States Patent
Rogers et al.

(10) Patent No.: US 11,064,946 B2
(45) Date of Patent: Jul. 20, 2021

(54) DEVICES AND RELATED METHODS FOR EPIDERMAL CHARACTERIZATION OF BIOFLUIDS

(71) Applicant: The Board of Trustees of the University of Illinois, Urbana, IL (US)

(72) Inventors: John A. Rogers, Champaign, IL (US); Ahyeon Koh, Champaign, IL (US); Daeshik Kang, Urbana, IL (US); YuHao Liu, Urbana, IL (US); Xian Huang, Rolla, MO (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 682 days.

(21) Appl. No.: 15/501,373

(22) PCT Filed: Aug. 11, 2015

(86) PCT No.: PCT/US2015/044638
§ 371 (c)(1),
(2) Date: Feb. 2, 2017

(87) PCT Pub. No.: WO2016/025468
PCT Pub. Date: Feb. 18, 2016

(65) Prior Publication Data
US 2017/0231571 A1    Aug. 17, 2017

Related U.S. Application Data

(60) Provisional application No. 62/035,823, filed on Aug. 11, 2014, provisional application No. 62/142,877, filed on Apr. 3, 2015.

(51) Int. Cl.
*A61B 5/00* (2006.01)
*A61B 5/145* (2006.01)
(Continued)

(52) U.S. Cl.
CPC ............ *A61B 5/6833* (2013.01); *A61B 5/002* (2013.01); *A61B 5/01* (2013.01); *A61B 5/053* (2013.01);
(Continued)

(58) Field of Classification Search
CPC .................................................. A61B 5/6833
See application file for complete search history.

(56) References Cited

U.S. PATENT DOCUMENTS 3,822,115 A    7/1974   Morin et al.
3,852,092 A   12/1974   Patterson et al.
(Continued)

FOREIGN PATENT DOCUMENTS

CN    101490414 A    7/2009
CN    103336007      10/2013
(Continued)

OTHER PUBLICATIONS

Curto, V. F., Fay, C., Coyle, S., Byrne, R., O'Toole, C., Barry, C., . . . & Benito-Lopez, F. (2012). Real-time sweat pH monitoring based on a wearable chemical barcode micro-fluidic platform incorporating ionic liquids. Sensors and Actuators B: Chemical, 171, 1327-1334. (Year: 2012).*

(Continued)

*Primary Examiner* — Daniel L Cerioni
*Assistant Examiner* — Yasmeen S Warsi
(74) *Attorney, Agent, or Firm* — Leydig, Voit & Mayer, Ltd.

(57) ABSTRACT

Skin-mounted or epidermal devices and methods for monitoring biofluids are disclosed. The devices comprise a functional substrate that is mechanically and/or thermally matched to skin to provide durable adhesion for long-term wear. The functional substrates allow for the microfluidic transport of biofluids from the skin to one or more sensors (Continued)

that measure and/or detect biological parameters, such as rate of biofluid production, biofluid volume, and biomarker concentration. Sensors within the devices may be mechanical, electrical or chemical, with colorimetric indicators being observable by the naked eye or with a portable electronic device (e.g., a smartphone). By monitoring changes in an individual's health state over time, the disclosed devices may provide early indications of abnormal conditions.

40 Claims, 32 Drawing Sheets

(51) Int. Cl.
    *A61B 5/103*     (2006.01)
    *A61B 5/1455*     (2006.01)
    *A61B 5/01*     (2006.01)
    *A61B 5/053*     (2021.01)
    *A61B 5/1468*     (2006.01)
    *B01L 3/00*     (2006.01)
    *A61B 5/1477*     (2006.01)

(52) U.S. Cl.
    CPC .......... *A61B 5/1032* (2013.01); *A61B 5/1455* (2013.01); *A61B 5/14517* (2013.01); *A61B 5/4266* (2013.01); *A61B 5/6898* (2013.01); *A61B 5/0059* (2013.01); *A61B 5/0075* (2013.01); *A61B 5/1468* (2013.01); *A61B 5/1477* (2013.01); *A61B 5/14514* (2013.01); *A61B 5/14532* (2013.01); *A61B 5/14539* (2013.01); *A61B 5/14546* (2013.01); *A61B 2562/12* (2013.01); *A61B 2576/00* (2013.01); *B01L 3/505* (2013.01); *B01L 3/502707* (2013.01)

(56) References Cited

U.S. PATENT DOCUMENTS

| | | |
|---|---|---|
| 3,951,133 A | 4/1976 | Reese |
| 3,993,809 A | 11/1976 | Schranz et al. |
| 4,327,742 A | 5/1982 | Meyers et al. |
| 4,393,142 A | 7/1983 | Stephens |
| 4,433,637 A | 2/1984 | Buirley et al. |
| 5,032,506 A | 7/1991 | Palmer et al. |
| 5,053,339 A | 10/1991 | Patel |
| 5,096,671 A | 3/1992 | Kane et al. |
| 5,207,227 A | 5/1993 | Powers |
| 5,290,519 A | 3/1994 | Bar-Or et al. |
| 5,678,566 A | 10/1997 | Dribbon |
| 5,763,282 A | 6/1998 | Zhang |
| 7,195,733 B2 | 3/2007 | Rogers et al. |
| 7,291,497 B2 | 11/2007 | Holmes et al. |
| 7,383,072 B2 | 6/2008 | Edmonson et al. |
| 7,521,292 B2 | 4/2009 | Rogers et al. |
| 7,557,367 B2 | 7/2009 | Rogers et al. |
| 7,622,367 B1 | 11/2009 | Nuzzo et al. |
| 7,635,362 B2 | 12/2009 | Hwang et al. |
| 7,704,684 B2 | 4/2010 | Rogers et al. |
| 7,705,280 B2 | 4/2010 | Nuzzo et al. |
| 7,799,699 B2 | 9/2010 | Nuzzo et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,198,621 B2 | 6/2012 | Rogers et al. |
| 8,217,381 B2 | 7/2012 | Rogers et al. |
| 8,357,335 B1 | 1/2013 | Harvey et al. |
| 8,367,035 B2 | 2/2013 | Rogers et al. |
| 8,394,706 B2 | 3/2013 | Nuzzo et al. |
| 8,440,546 B2 | 5/2013 | Nuzzo et al. |
| 8,470,701 B2 | 6/2013 | Rogers et al. |
| 8,552,299 B2 | 10/2013 | Rogers et al. |
| 8,562,095 B2 | 10/2013 | Alleyene et al. |
| 8,664,699 B2 | 3/2014 | Nuzzo et al. |
| 8,666,471 B2 | 3/2014 | Rogers et al. |
| 8,679,888 B2 | 3/2014 | Rogers et al. |
| 8,722,458 B2 | 5/2014 | Rogers et al. |
| 8,729,524 B2 | 5/2014 | Rogers et al. |
| 8,754,396 B2 | 6/2014 | Rogers et al. |
| 8,865,489 B2 | 10/2014 | Rogers et al. |
| 8,895,406 B2 | 11/2014 | Rogers et al. |
| 8,905,772 B2 | 12/2014 | Rogers et al. |
| 8,934,965 B2 | 1/2015 | Rogers et al. |
| 8,946,683 B2 | 2/2015 | Rogers et al. |
| 9,057,994 B2 | 6/2015 | Rogers et al. |
| 9,061,494 B2 | 6/2015 | Rogers et al. |
| 9,105,555 B2 | 8/2015 | Rogers et al. |
| 9,105,782 B2 | 8/2015 | Rogers et al. |
| 9,117,940 B2 | 8/2015 | Rogers et al. |
| 9,278,522 B2 | 3/2016 | Rogers et al. |
| 9,324,733 B2 | 4/2016 | Rogers et al. |
| 9,349,900 B2 | 5/2016 | Rogers et al. |
| 9,442,285 B2 | 9/2016 | Rogers |
| 9,450,043 B2 | 9/2016 | Nuzzo et al. |
| 9,487,002 B2 | 11/2016 | Rogers et al. |
| 9,496,229 B2 | 11/2016 | Rogers et al. |
| 9,515,025 B2 | 12/2016 | Rogers et al. |
| 9,554,484 B2 | 1/2017 | Rogers et al. |
| 9,555,644 B2 | 1/2017 | Rogers et al. |
| 9,601,671 B2 | 3/2017 | Rogers et al. |
| 9,613,911 B2 | 4/2017 | Rogers et al. |
| 9,647,171 B2 | 5/2017 | Rogers et al. |
| 9,691,873 B2 | 6/2017 | Rogers et al. |
| 9,761,444 B2 | 9/2017 | Nuzzo et al. |
| 9,765,934 B2 | 9/2017 | Rogers et al. |
| 9,768,086 B2 | 9/2017 | Nuzzo et al. |
| 9,825,229 B2 | 11/2017 | Rogers et al. |
| 9,875,974 B2 | 1/2018 | Rogers et al. |
| 2002/0135772 A1 | 9/2002 | Bornhop et al. |
| 2002/0156471 A1 | 10/2002 | Stern et al. |
| 2005/0048571 A1 | 3/2005 | Danielson et al. |
| 2005/0238967 A1 | 10/2005 | Rogers et al. |
| 2006/0038182 A1 | 2/2006 | Rogers et al. |
| 2006/0117859 A1 | 6/2006 | Liu et al. |
| 2006/0286488 A1 | 12/2006 | Rogers et al. |
| 2006/0286785 A1 | 12/2006 | Rogers et al. |
| 2007/0032089 A1 | 2/2007 | Nuzzo et al. |
| 2008/0055581 A1 | 3/2008 | Rogers et al. |
| 2008/0108171 A1 | 5/2008 | Rogers et al. |
| 2008/0157235 A1 | 7/2008 | Rogers et al. |
| 2008/0212102 A1 | 9/2008 | Nuzzo et al. |
| 2008/0275319 A1 | 11/2008 | Van Gogh et al. |
| 2009/0199960 A1 | 8/2009 | Nuzzo et al. |
| 2009/0204100 A1 | 8/2009 | Van Pieterson et al. |
| 2009/0294803 A1 | 12/2009 | Nuzzo et al. |
| 2010/0002402 A1 | 1/2010 | Rogers et al. |
| 2010/0003143 A1 | 1/2010 | Toonder et al. |
| 2010/0052112 A1 | 3/2010 | Rogers et al. |
| 2010/0059863 A1 | 3/2010 | Rogers et al. |
| 2010/0072577 A1 | 3/2010 | Nuzzo et al. |
| 2010/0113894 A1 | 5/2010 | Padiy |
| 2010/0283069 A1 | 11/2010 | Rogers et al. |
| 2010/0289124 A1 | 11/2010 | Nuzzo et al. |
| 2010/0302040 A1 | 12/2010 | Davidowitz |
| 2010/0317132 A1 | 12/2010 | Rogers et al. |
| 2011/0073475 A1 | 3/2011 | Kastanos et al. |
| 2011/0147715 A1 | 6/2011 | Rogers et al. |
| 2011/0152643 A1 | 6/2011 | Xue et al. |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0245713 A1 | 10/2011 | Rensen et al. |
| 2011/0266561 A1 | 11/2011 | Rogers et al. |
| 2011/0277813 A1 | 11/2011 | Rogers et al. |
| 2011/0316120 A1 | 12/2011 | Rogers et al. |
| 2012/0024833 A1 | 2/2012 | Klewer et al. |
| 2012/0071783 A1 | 3/2012 | Klee et al. |
| 2012/0083099 A1 | 4/2012 | Nuzzo et al. |

(56) References Cited

U.S. PATENT DOCUMENTS

| | | |
|---|---|---|
| 2012/0105528 A1 | 5/2012 | Alleyne et al. |
| 2012/0135541 A1 | 5/2012 | Herr et al. |
| 2012/0157804 A1 | 6/2012 | Rogers et al. |
| 2012/0165759 A1 | 6/2012 | Rogers et al. |
| 2012/0190989 A1 | 7/2012 | Kaiser et al. |
| 2012/0238901 A1 | 9/2012 | Augustine |
| 2012/0261551 A1 | 10/2012 | Rogers |
| 2012/0320581 A1 | 12/2012 | Rogers et al. |
| 2012/0321785 A1 | 12/2012 | Rogers et al. |
| 2012/0327608 A1 | 12/2012 | Rogers et al. |
| 2013/0036928 A1 | 2/2013 | Rogers et al. |
| 2013/0041235 A1 | 2/2013 | Rogers et al. |
| 2013/0072775 A1 | 3/2013 | Rogers et al. |
| 2013/0100618 A1 | 4/2013 | Rogers et al. |
| 2013/0140649 A1 | 6/2013 | Rogers et al. |
| 2013/0150685 A1 | 6/2013 | Toth |
| 2013/0218046 A1 | 8/2013 | Bowman et al. |
| 2013/0245546 A1 | 9/2013 | Hayn |
| 2013/0320503 A1 | 12/2013 | Nuzzo et al. |
| 2013/0333094 A1 | 12/2013 | Rogers et al. |
| 2014/0025000 A1* | 1/2014 | Currie ............ A61B 5/0059 604/66 |
| 2014/0092158 A1 | 4/2014 | Alleyne et al. |
| 2014/0140020 A1 | 5/2014 | Rogers et al. |
| 2014/0163390 A1 | 6/2014 | Rogers et al. |
| 2014/0191236 A1 | 7/2014 | Nuzzo et al. |
| 2014/0216524 A1 | 8/2014 | Rogers et al. |
| 2014/0220422 A1 | 8/2014 | Rogers et al. |
| 2014/0288381 A1 | 9/2014 | Faarbaek et al. |
| 2014/0305900 A1 | 10/2014 | Rogers et al. |
| 2014/0323968 A1 | 10/2014 | Rogers et al. |
| 2014/0361409 A1 | 12/2014 | Rogers et al. |
| 2014/0373898 A1 | 12/2014 | Rogers et al. |
| 2014/0374872 A1 | 12/2014 | Rogers et al. |
| 2015/0001462 A1 | 1/2015 | Rogers et al. |
| 2015/0080695 A1 | 3/2015 | Rogers et al. |
| 2015/0132873 A1 | 5/2015 | Rogers et al. |
| 2015/0141767 A1 | 5/2015 | Rogers et al. |
| 2015/0181700 A1 | 6/2015 | Rogers et al. |
| 2015/0207012 A1 | 7/2015 | Rogers et al. |
| 2015/0237711 A1 | 8/2015 | Rogers et al. |
| 2015/0290938 A1 | 10/2015 | Rogers et al. |
| 2015/0373831 A1 | 12/2015 | Rogers et al. |
| 2015/0380355 A1 | 12/2015 | Rogers et al. |
| 2016/0005700 A1 | 1/2016 | Rogers et al. |
| 2016/0027737 A1 | 1/2016 | Rogers et al. |
| 2016/0050750 A1 | 2/2016 | Rogers et al. |
| 2016/0066789 A1 | 3/2016 | Rogers et al. |
| 2016/0072027 A1 | 3/2016 | Rogers et al. |
| 2016/0133843 A1 | 5/2016 | Rogers et al. |
| 2016/0136877 A1 | 5/2016 | Rogers et al. |
| 2016/0284544 A1 | 9/2016 | Nuzzo et al. |
| 2016/0293794 A1 | 10/2016 | Nuzzo et al. |
| 2016/0361715 A1 | 12/2016 | Shi et al. |
| 2016/0374758 A1 | 12/2016 | Jones et al. |
| 2016/0381789 A1 | 12/2016 | Rogers et al. |
| 2017/0020402 A1 | 1/2017 | Rogers et al. |
| 2017/0128015 A1 | 5/2017 | Rogers et al. |
| 2017/0130187 A1 | 5/2017 | Lee et al. |
| 2017/0164482 A1 | 6/2017 | Rogers et al. |
| 2017/0179085 A1 | 6/2017 | Rogers et al. |
| 2017/0179100 A1 | 6/2017 | Rogers et al. |
| 2017/0179356 A1 | 6/2017 | Rogers et al. |
| 2017/0181704 A1 | 6/2017 | Rogers et al. |
| 2017/0200679 A1 | 7/2017 | Rogers et al. |
| 2017/0200707 A1 | 7/2017 | Rogers et al. |
| 2017/0210117 A1 | 7/2017 | Rogers et al. |
| 2017/0224257 A1 | 8/2017 | Rogers et al. |
| 2017/0291817 A1 | 10/2017 | Rogers et al. |
| 2017/0309733 A1 | 10/2017 | Nuzzo et al. |
| 2017/0347891 A1 | 12/2017 | Rogers et al. |
| 2017/0365557 A1 | 12/2017 | Rogers et al. |
| 2018/0014734 A1 | 1/2018 | Rogers et al. |
| 2018/0020966 A1 | 1/2018 | Begtrup et al. |
| 2018/0064377 A1 | 3/2018 | Rogers et al. |

FOREIGN PATENT DOCUMENTS

| | | | |
|---|---|---|---|
| DE | 1087752 | 8/1960 | |
| EP | 3006937 | 4/2016 | |
| JP | 2004-538478 | 12/2004 | |
| JP | 2009-518113 | 5/2009 | |
| JP | 2010-221042 | 10/2010 | |
| JP | 2012-135626 | 7/2012 | |
| JP | 2013-544362 | 12/2013 | |
| WO | WO 1996/004876 | 2/1996 | |
| WO | WO 2001/083027 | 11/2001 | |
| WO | WO 2003/015636 | 2/2003 | |
| WO | WO 2005/057467 | 6/2005 | |
| WO | WO 2007/070093 | 6/2007 | |
| WO | WO 2009/144615 | 12/2009 | |
| WO | WO-2010030609 A1 * | 3/2010 | ......... A61B 5/14532 |
| WO | WO 2010/045247 | 4/2010 | |
| WO | WO 2012/119128 | 9/2012 | |
| WO | WO 2013/152087 | 10/2013 | |
| WO | WO 2016/196673 | 12/2016 | |
| WO | WO 2016/196675 | 12/2016 | |
| WO | WO 2017/004531 | 1/2017 | |
| WO | WO 2017/004576 | 1/2017 | |

OTHER PUBLICATIONS

U.S. Appl. No. 11/001,689, filed Dec. 1, 2004, 2006/0286488, Dec. 21, 2006, U.S. Pat. No. 7,704,684, Apr. 27, 2010.

U.S. Appl. No. 11/115,954, filed Apr. 27, 2005, 2005/0238967, Oct. 27, 2005, U.S. Pat. No. 7,195,733, Mar. 27, 2007.

U.S. Appl. No. 11/145,574, filed Jun. 2, 2005, 2009/0294803, Dec. 3, 2009, U.S. Pat. No. 7,622,367, Nov. 24, 2009.

U.S. Appl. No. 11/145,542, filed Jun. 2, 2005, 2006/0038182, Feb. 23, 2006, U.S. Pat. No. 7,557,367, Jul. 7, 2009.

U.S. Appl. No. 11/421,654, filed Jun. 1, 2006, 2007/0032089, Feb. 8, 2007, U.S. Pat. No. 7,799,699, Sep. 21, 2010.

U.S. Appl. No. 11/423,287, filed Jun. 9, 2006, 2006/0286785, Dec. 21, 2006, U.S. Pat. No. 7,521,292, Apr. 21, 2009.

U.S. Appl. No. 11/423,192, filed Jun. 9, 2006, 2009/0199960, Aug. 13, 2009, U.S. Pat. No. 7,943,491, May 17, 2011.

U.S. Appl. No. 11/465,317, filed Aug. 17, 2006.

U.S. Appl. No. 11/675,659, filed Feb. 16, 2007, 2008/0055581, Mar. 6, 2008.

U.S. Appl. No. 11/782,799, filed Jul. 25, 2007, 2008/0212102, Sep. 4, 2008, U.S. Pat. No. 7,705,280, Apr. 27, 2010.

U.S. Appl. No. 11/851,182, filed Sep. 6, 2007, 2008/0157235, Jul. 3, 2008, U.S. Pat. No. 8,217,381, Jul. 10, 2012.

U.S. Appl. No. 11/858,788, filed Sep. 20, 2007, 2008/0108171, May 8, 2008, U.S. Pat. No. 7,932,123, Apr. 26, 2011.

U.S. Appl. No. 11/981,380, filed Oct. 31, 2007, 2010/0283069, Nov. 11, 2010, U.S. Pat. No. 7,972,875, Jul. 5, 2011.

U.S. Appl. No. 12/372,605, filed Feb. 17, 2009.

U.S. Appl. No. 12/398,811, filed Mar. 5, 2009, 2010/0002402, Jan. 7, 2010, U.S. Pat. No. 8,552,299, Oct. 8, 2013.

U.S. Appl. No. 12/405,475, filed Mar. 17, 2009, 2010/0059863, Mar. 11, 2010, U.S. Pat. No. 8,198,621, Jun. 12, 2012.

U.S. Appl. No. 12/418,071, filed Apr. 3, 2009, 2010/0052112, Mar. 4, 2010, U.S. Pat. No. 8,470,701, Jun. 25, 2013.

U.S. Appl. No. 12/564,566, filed Sep. 22, 2009, 2010/0072577, Mar. 25, 2010, U.S. Pat. No. 7,982,296, Jul. 19, 2011.

U.S. Appl. No. 12/669,287, filed Jan. 15, 2010, 2011/0187798, Aug. 4, 2011, U.S. Pat. No. 9,061,494, Jun. 23, 2015.

U.S. Appl. No. 12/778,588, filed May 12, 2010, 2010/0317132, Dec. 16, 2010, U.S. Pat. No. 8,865,489, Oct. 21, 2014.

U.S. Appl. No. 12/844,492, filed Jul. 27, 2010, 2010/0289124, Nov. 18, 2010, U.S. Pat. No. 8,039,847, Oct. 18, 2011.

U.S. Appl. No. 12/892,001, filed Sep. 28, 2010, 2011/0230747, Sep. 22, 2011, U.S. Pat. No. 8,666,471, Mar. 4, 2014.

U.S. Appl. No. 12/916,934, filed Nov. 1, 2010, 2012/0105528, May 3, 2012, U.S. Pat. No. 8,562,095, Oct. 22, 2013.

U.S. Appl. No. 12/947,120, filed Nov. 16, 2010, 2011/0170225, Jul. 14, 2011, U.S. Pat. No. 9,057,994, Jun. 16, 2015.

U.S. Appl. No. 12/996,924, filed Dec. 8, 2010, 2011/0147715, Jun. 23, 2011, U.S. Pat. No. 8,946,683, Feb. 3, 2015.

(56) References Cited

OTHER PUBLICATIONS

U.S. Appl. No. 12/968,637, filed Dec. 15, 2010, 2012/0157804, Jun. 21, 2012.
U.S. Appl. No. 13/046,191, filed Mar. 11, 2011, 2012/0165759, Jun. 28, 2012.
U.S. Appl. No. 13/071,027, filed Mar. 24, 2011, 2011/0171813, Jul. 14, 2011, U.S. Pat. No. 8,895,406, Nov. 25, 2014.
U.S. Appl. No. 13/095,502, filed Apr. 27, 2011.
U.S. Appl. No. 13/100,774, filed May 4, 2011, 2011/0266561, Nov. 3, 2011, U.S. Pat. No. 8,722,458, May 13, 2014.
U.S. Appl. No. 13/113,504, filed May 23, 2011, 2011/0220890, Sep. 15, 2011, U.S. Pat. No. 8,440,546, May 14, 2013.
U.S. Appl. No. 13/120,486, filed Aug. 4, 2011, 2011/0277813, Nov. 17, 2011, U.S. Pat. No. 8,679,888, Mar. 25, 2014.
U.S. Appl. No. 13/228,041, filed Sep. 8, 2011, 2011/0316120, Dec. 29, 2011.
U.S. Appl. No. 13/270,954, filed Oct. 11, 2011, 2012/0083099, Apr. 5, 2012, U.S. Pat. No. 8,394,706, Mar. 12, 2013.
U.S. Appl. No. 13/349,336, filed Jan. 12, 2012, 2012/0261551, Oct. 18, 2012, U.S. Pat. No. 9,442,285, Sep. 13, 2016.
U.S. Appl. No. 13/441,618, filed Apr. 6, 2012, 2013/0100618, Apr. 25, 2013, U.S. Pat. No. 8,754,396, Jun. 17, 2014.
U.S. Appl. No. 13/441,598, filed Apr. 6, 2012, 2012/0327608, Dec. 27, 2012, U.S. Pat. No. 8,729,524, May 20, 2014.
U.S. Appl. No. 13/472,165, filed May 15, 2012, 2012/0320581, Dec. 20, 2012, U.S. Pat. No. 9,765,934, Sep. 19, 2017.
U.S. Appl. No. 13/486,726, filed Jun. 1, 2012, 2013/0072775, Mar. 21, 2013, U.S. Pat. No. 8,934,965, Jan. 13, 2015.
U.S. Appl. No. 13/492,636, filed Jun. 8, 2012, 2013/0041235, Feb. 14, 2013.
U.S. Appl. No. 13/549,291, filed Jul. 13, 2012, 2013/0036928, Feb. 14, 2013, U.S. Pat. No. 9,555,644, Jan. 31, 2017.
U.S. Appl. No. 13/596,343, filed Aug. 28, 2012, 2012/0321785, Dec. 20, 2012, U.S. Pat. No. 8,367,035, Feb. 5, 2013.
U.S. Appl. No. 13/624,096, filed Sep. 21, 2012, 2013/0140649, Jun. 6, 2013, U.S. Pat. No. 9,691,873, Jun. 27, 2017.
U.S. Appl. No. 13/801,868, filed Mar. 13, 2013, 2013/0320503, Dec. 5, 2013, U.S. Pat. No. 8,664,699, Mar. 4, 2014.
U.S. Appl. No. 13/835,284, filed Mar. 15, 2013, 2014/0220422, Aug. 7, 2014.
U.S. Appl. No. 13/853,770, filed Mar. 29, 2013, 2013/0333094, Dec. 19, 2013, U.S. Pat. No. 9,554,484, Jan. 24, 2017.
U.S. Appl. No. 13/974,963, filed Aug. 23, 2013, 2014/0140020, May 22, 2014, U.S. Pat. No. 8,905,772, Dec. 9, 2014.
U.S. Appl. No. 14/033,765, filed Sep. 23, 2013, 2014/0092158, Apr. 3, 2014, U.S. Pat. No. 9,278,522, Mar. 8, 2016.
U.S. Appl. No. 14/140,299, filed Dec. 24, 2013, 2014/0163390, Jun. 12, 2014.
U.S. Appl. No. 14/155,010, filed Jan. 14, 2014, 2014/0191236, Jul. 10, 2014, U.S. Pat. No. 9,450,043, Sep. 20, 2016.
U.S. Appl. No. 14/173,525, filed Feb. 5, 2014, 2014/0216524, Aug. 7, 2014, U.S. Pat. No. 9,105,782, Aug. 11, 2015.
U.S. Appl. No. 14/209,481, filed Mar. 13, 2014, 2014/0373898, Dec. 25, 2014, U.S. Pat. No. 9,117,940, Aug. 25, 2015.
U.S. Appl. No. 14/220,910, filed Mar. 20, 2014, 2014/0374872, Dec. 25, 2014, U.S. Pat. No. 9,324,733, Apr. 26, 2016.
U.S. Appl. No. 14/220,923, filed Mar. 20, 2014, 2015/0001462, Jan. 1, 2015, U.S. Pat. No. 9,105,555, Aug. 11, 2015.
U.S. Appl. No. 14/246,962, filed Apr. 7, 2014, 2014/0361409, Dec. 11, 2014, U.S. Pat. No. 9,349,900, May 24, 2016.
U.S. Appl. No. 14/251,259, filed Apr. 11, 2014, 2014/0323968, Oct. 30, 2014.
U.S. Appl. No. 14/250,671, filed Apr. 11, 2014, 2014/0305900, Oct. 16, 2014, U.S. Pat. No. 9,496,229, Nov. 15, 2016.
U.S. Appl. No. 14/479,100, filed Sep. 5, 2014, 2015/0132873, May 14, 2015, U.S. Pat. No. 9,647,171, May 9, 2017.
U.S. Appl. No. 14/504,736, filed Oct. 2, 2014, 2015/0141767, May 21, 2015.
U.S. Appl. No. 14/521,319, filed Oct. 22, 2014, 2015/0181700, Jun. 25, 2015.
U.S. Appl. No. 14/532,687, filed Nov. 4, 2014, 2015/0080695, Mar. 19, 2015.
U.S. Appl. No. 14/599,290, filed Jan. 16, 2015, 2015/0207012, Jul. 23, 2015.
U.S. Appl. No. 14/686,304, filed Apr. 14, 2015, 2015/0290938, Oct. 15, 2015, U.S. Pat. No. 9,487,002, Nov. 8, 2016.
U.S. Appl. No. 14/706,733, filed May 7, 2015, 2015/0237711, Aug. 20, 2015.
U.S. Appl. No. 14/789,645, filed Jul. 1, 2015, 2016/0027737, Jan. 28, 2016, U.S. Pat. No. 9,515,025, Dec. 6, 2016.
U.S. Appl. No. 14/800,363, filed Jul. 15, 2015, 2016/0072027, Mar. 10, 2016, U.S. Pat. No. 9,601,671, Mar. 21, 2017.
U.S. Appl. No. 14/818,109, filed Aug. 4, 2015, 2016/0050750, Feb. 18, 2016.
U.S. Appl. No. 14/766,333, filed Aug. 6, 2015, 2015/0380355, Dec. 31, 2015, U.S. Pat. No. 9,613,911, Apr. 4, 2017.
U.S. Appl. No. 14/766,926, filed Aug. 10, 2015, 2016/0066789, Mar. 10, 2016.
U.S. Appl. No. 14/772,354, filed Sep. 2, 2015, 2016/0005700, Jan. 7, 2016, U.S. Pat. No. 9,875,974, Jan. 23, 2018.
U.S. Appl. No. 14/772,312, filed Sep. 2, 2015, 2016/0133843, May 12, 2016, U.S. Pat. No. 9,825,229, Nov. 21, 2017.
U.S. Appl. No. 14/944,039, filed Nov. 17, 2015, 2016/0136877, May 19, 2016.
U.S. Appl. No. 14/766,301, filed Dec. 24, 2015, 2015/0373831, Dec. 24, 2015.
U.S. Appl. No. 15/084,091, filed Mar. 29, 2016, 2016/0284544, Sep. 29, 2016, U.S. Pat. No. 9,761,444, Sep. 12, 2017.
U.S. Appl. No. 15/084,211, filed Mar. 29, 2016, 2016/0293794, Oct. 6, 2016, U.S. Pat. No. 9,768,086, Sep. 19, 2017.
U.S. Appl. No. 15/084,112, filed Mar. 29, 2016, 2016/0381789, Dec. 29, 2016.
U.S. Appl. No. 15/146,629, filed May 4, 2016, 2017/0020402, Jan. 26, 2017.
U.S. Appl. No. 15/339,338, filed Oct. 31, 2016, 2017/0200679, Jul. 13, 2017.
U.S. Appl. No. 15/349,525, filed Nov. 11, 2016, 2017/0128015, May 11, 2017.
U.S. Appl. No. 15/351,234, filed Nov. 14, 2016, 2017/0164482, Jun. 8, 2017.
U.S. Appl. No. 15/354,951, filed Nov. 17, 2016, 2017/0291817, Oct. 12, 2017.
U.S. Appl. No. 15/374,926, filed Dec. 9, 2016, 2017/0210117, Jul. 27, 2017.
U.S. Appl. No. 15/375,514, filed Dec. 12, 2016, 2017/0181704, Dec. 12, 2016.
U.S. Appl. No. 15/402,684, filed Jan. 10, 2017, 2017/0179100, Jun. 22, 2017.
U.S. Appl. No. 15/402,718, filed Jan. 10, 2017, 2017/0179085, Jan. 10, 2017.
U.S. Appl. No. 15/402,723, filed Jan. 10, 2017, 2017/0179356, Jun. 22, 2017.
U.S. Appl. No. 15/501,364, filed Feb. 2, 2017, 2017/0224257, Aug. 10, 2017.
U.S. Appl. No. 15/501,379, filed Feb. 2, 2017, 2018/0014734, Jan. 18, 2018.
U.S. Appl. No. 15/470,780, filed Mar. 27, 2017, 2017/0200707, Jul. 13, 2017.
U.S. Appl. No. 15/515,494, filed Mar. 29, 2017, 2017/0347891, Dec. 7, 2017.
U.S. Appl. No. 15/477,865, filed Apr. 3, 2017, 2017/0365557, Dec. 21, 2017.
U.S. Appl. No. 15/625,087, filed Jun. 16, 2017, 2018/0064377, Mar. 8, 2018.
U.S. Appl. No. 15/632,004, filed Jun. 23, 2017.
U.S. Appl. No. 15/640,206, filed Jun. 30, 2017, 2017/0309733, Oct. 26, 2017.
U.S. Appl. No. 15/578,602, filed Nov. 30, 2017.
U.S. Appl. No. 15/578,617, filed Nov. 30, 2017.
U.S. Appl. No. 15/741,081, filed Dec. 29, 2017.
U.S. Appl. No. 15/738,043, filed Dec. 19, 2017.
U.S. Appl. No. 15/861,257, filed Jan. 3, 2018.
U.S. Appl. No. 15/865,033, filed Jan. 8, 2018.

(56) References Cited

OTHER PUBLICATIONS

PCT/US16/35331, Jun. 1, 2016, WO 2016/196673, Dec. 8, 2016.
PCT/US16/35336, Jun. 1, 2016, WO 2016/196675, Dec. 8, 2016.
PCT/US16/40717, Jul. 1, 2016, WO 2017/004531, Jan. 5, 2017.
PCT/US16/40814, Jul. 1, 2016, WO 2017/004576, Jan. 5, 2017.
Åberg et al. (2004) "Skin cancer identification using multifrequency electrical impedance—a potential screening tool," IEEE Transactions on Biomedical Engineering. 51(12):2097-2102.
Agache et al. (1980) Mechanical properties and Young's modulus of human skin in vivo. Arch. Dermatol. Res. 269:221-232.
Ahn et al. (2012) "Stretchable electronics: materials, architectures and integrations," J. Phys. D: Appl. Phys. 45:103001.
Aitken et al. (1996) "Textile applications of thermochromic systems," Rev. Prog. Coloration. 26:1-8.
Akhtar et al. (2010) "Sensitivity of digital thermal monitoring parameters to reactive hyperemia," J. Biomech. Eng. 132:051005.
Alanen et al. (2004) "Measurement of hydration in the stratum corneum with the MoistureMeter and comparison with the Corneometer," Skin Research and Technology. 10(1):32-37.
Alba (Jul. 11, 2014) "Startup Builds Sensors that Will Analyze Sweat to Track Your Health," Wired. Accessible on the Internet at URL: https://www.wired.com/2014/11/sweat-sensors. [Last Accessed Feb. 27, 2015] 2 pgs.
Allen (2007) "Photoplethysmography and its application in clinical physiological measurement," Physiol. Meas. 28:R1-R39.
Allen et al. (2002) "Microvascular blood flow and skin temperature changes in the fingers following a deep nspiratory gasp," Physiol. Meas. 23:365-373.
Anderson et al. (2005) "Liquid-crystal thermography: Illumination spectral effects. Part 1—Experiments," J. Heat. Trans. 127:581-587.
Armstrong (2007) "Assessing hydration status: the elusive gold standard," Journal of the American College of Nutrition. 26(Suppl 5): 575S-584S.
Armstrong et al. (1997) "Bioimpedance spectroscopy technique: intra-, extracellular, and total body water," Med. Sci. Sports Exerc. 29:1657-1663.
Arnaud et al. (1994) "A micro thermal diffusion sensor for non-invasive skin characterization," Sensors and Actuators: A. Physical. 41:240-243.
Arora et al. (2008) "Effectiveness of a noninvasive digital infrared thermal imaging system in the detection of breast cancer," Am. J. Surg. 196:523-526.
Arora et al. (2008) "Micro-scale devices for transdermal drug delivery," International Journal of Pharmaceutics. 364(2):227-236.
Arumugam et al. (1994) "Effect of strain-rate on the fracture-behavior of skin," Journal of Biosciences. 19:307-313.
Asada et al. (2003) "Hutchinson, Mobile monitoring with wearable photoplethysmographic biosensors," IEEE engineering in medicine and biology magazine: The quarterly magazine of the Engineering in Medicine & Biology Society. 22:28-40.
Badugu et al. (2003) "A Glucose Sensing Contact Lens: A Non-Invasive Technique for Continuous Physiological Glucose Monitoring," J. Fluoresc. 13:371-374.
Badugu et al. (2003) "Non-invasive continuous monitoring of physiological glucose using a monosaccharide-sensing contact lens," Anal. Chem. 76:610-618.
Bakan et al. (1984) "Liquid-crystal microcapsule medical device used for thermographic examination of the human female breast," Appl. Biochem. Biotechnol. 10:289-299.
Bandodkar et al. (2012) "Tattoo-based potentiometric ion-selective sensors for epidermal pH monitoring," Analyst. 138:123-128.
Bandodkar et al. (Apr. 15, 2014) "Epidermal tattoo potentiometric sodium sensors with wireless signal transduction for continuous non-invasive sweat monitoring," Biosensors and Bioelectronics. 54:603-609.
Bandodkar et al. (Dec. 12, 2014) "Tattoo-Based Noninvasive Glucose Monitoring: A Proof-of-Concept Study," Analytical Chemistry. 87(1):394-398.
Bandodkar et al. (Jul. 18, 2013) "Solid-state Forensic Finger sensor for integrated sampling and detection of gunshot residue and explosives: towards 'Lab-on-a-finger'," Analyst. 138:5288-5295.
Bandodkar et al. (Jul. 2014) "Non-invasive wearable electrochemical sensors: a review," Trends in Biotech. 32(7):363-371.
Barone et al. (1992) "Blood-flow measurements of injured peripheral nerves by laser Doppler flowmetry," J. Reconstr. Microsurg. 8(4):319-323.
Batt et al. (1986) "Hydration of the stratum corneum," International Journal of Cosmetic Science. 8(6):253-264.
Benelam et al. (2010) "Hydration and Health: A Review," Nutr. Bull. 35:3-25.
Bernjak et al. (2008) "Low-frequency blood flow oscillations in congestive heart failure and after beta1-blockade treatment," Microvasc. Res. 76:224-232.
Bhadra et al. (2011) "Wireless Passive Sensor for Remote pH Monitoring," J. Nanotechnol. Eng. Med. 2:011011.
Biagi et al. (2012) "Simultaneous determination of lactate and pyruvate in human sweat using reversed-phase high-performance liquid chromatography: a noninvasive approach," Biomedical Chromatography. 26(11):1408-1415.
Birklein et al. (2008) "Neuropeptides, neurogenic inflammation and complex regional pain syndrome (CRPS)," Neurosci. Lett. 437(3):199-202.
Boas et al. (2010) "Laser speckle contrast imaging in biomedical optics," J. Biomed. Opt. 15(1):011109.
Bohling et al. (Jun. 12, 2013) "Comparison of the stratum corneum thickness measured in vivo with confocal Raman spectroscopy and confocal reflectance microscopy," Skin Res. Technol. 20(1):50-57.
Bonato (2010) "Wearable sensors and systems. From enabling technology to clinical applications," IEEE Eng. Med. Biol. Mag. 29:25-36.
Brenner et al. (1995) "A quantitative test for copper using bicinchoninic acid," Anal. Biochem. 226(1):80-84.
Brull et al. (1990) "Comparison of crystalline skin temperature to esophageal temperatures during anesthesia," Anesthesiology. 73(3A):A472.
Caduff et al. (2009) "Non-invasive glucose monitoring in patients with Type 1 diabetes: a Multisensor system combining sensors for dielectric and optical characterisation of skin," Biosens. Bioelectron. 24:2778-84.
Cameron et al. (1991) "Liquid-crystal thermography as a screening-test for deep-vein thrombosis in patients with cerebral infarction," Eur. J. Clin. Invest. 21:548-550.
Cametti et al. (2011) "Dielectric Relaxation Spectroscopy of Lysozyme Aqueous Solutions: Analysis of the δ-Dispersion and the Contribution of the Hydration Water," J. Phys. Chem. B. 115:7144-7153.
Carmichael et al. (2008) "Activation of the 5-HT1B/D receptor reduces hindlimb neurogenic inflammation caused by sensory nerve stimulation and capsaicin," Pain. 134(1-2):97-105.
Celermajer et al. (1992) "Non-invasive detection of endothelial dysfunction in children and adults at risk of atherosclerosis," Lancet. 340:1111-1115.
Chan et al. (2012) "Smart wearable systems: current status and future challenges," Artif. Intell. Med. 56:137-156.
Cheng et al. (Sep. 6, 2013) "Analysis of a concentric coplanar capacitor for epidermal hydration sensing," Sensors and Actuators A: Physical. 203:149-153.
Ching et al. (2008) "Simultaneous Transdermal Extraction of Glucose and Lactate From Human Subjects by Reverse Iontophoresis," Int. J. Nanomedicine. 3(2):211-223.
Chowdhury et al. (2012) "Application of thermochromic colorants on textiles: temperature dependence of colorimetric properties," Color. Technol. 129:232-237.
Chowdhury et al. (Jan. 2014) "Photochromic and thermochromic colorants in textile applications," J. Eng. Fiber. Fabr. 9:107-123.
clinicaltrials.gov (First) "Genetics and Pain Severity in Sickle Cell Disease," National Institutes of Health. Accessible on the Internet at URL: https://clinicaltrials.gov/ct2/show/NCT01441141. [Last Accessed Sep. 5, 2017].
Cohen (1977) "Measurement of thermal-properties of human-skin—review," J. Invest Dermatol. 69:333-338.

(56) References Cited

OTHER PUBLICATIONS

Coyle et al. (2010) "Biotex-Biosensing Textiles for Personalized Healthcare Management," IEEE Trans. Inf. Technol. Biomed. 14(2):364-370.
Coyle et al. (2010) "On-Body Chemical Sensors for Monitoring Sweat," In; Lecture Notes in Electrical Engineering: Wearable and Autonomous Biomedical Devices and Systems for Smart Environment. Eds.: Lay-Ekuakille et al. vol. 75. Springer. pp. 177-193.
Crandall et al. (2005) "Palmar skin blood flow and temperature responses throughout endoscopic sympathectomy," Anesth. Anal. 100:277-283.
Curto et al. (2012) "Real-Time Sweat pH Monitoring Based on a Wearable Chemical Barcode Micro-fluidic Platform Incorporating Ionic Liquids," Sensors and Actuators B. 171-172:327-1334.
Davison et al. (1972) "Detection of breast-cancer by liquid-crystal thermography—preliminary report," Cancer 29:1123-1132.
De La Hera et al. (1988) "Co-expression of Mac-1 and p150,95 on CD5+ B cells. Structural and functional characterization in a human chronic lymphocytic leukemia," Eur. J. Immunol. 18(7):1131-4.
Deshmukh (2012) "Enhancing clinical measures of postural stability with wearable sensors," Presented at Engineering in Medicine and Biology Society (EMBC), 2012 Annual International Conference of the IEEE, Aug. 28, 2012-Sep. 1, 2012.
Deshpande (2007) "Thermal analysis of vascular reactivity," MS thesis, Texas A&M University.
Dolphin et al. (1973) "Low-temperature chiral nematic liquid-crystals derived from beta-methylbutylaniline," J. Chem. Phys. 58:413-419.
Drack et al. (Oct. 20, 2014) "An imperceptible plastic electronic wrap," Adv. Mater. 27:34-40.
Draijer et al. (2009) "Review of laser speckle contrast techniques for visualizing tissue perfusion," Lasers in Medical Science. 24:639-651.
Ducharme et al. (1991) "In vivo thermal conductivity of the human forearm tissues," Journal of Applied Physiology. 70:2682-2690.
Dunn et al. (2001) "Dynamic imaging of cerebral blood flow using laser speckle," Journal of Cerebral Blood Flow and Metabolism. 21:195-201.
Egawa et al. (2007) "In vivo estimation of stratum corneum thickness from water concentration profiles obtained with Raman spectroscopy," Acta Derm. Venereol. 87(1):4-8.
El-Brawany et al. (2009) "Measurement of thermal and ultrasonic properties of some biological tissues," Journal of Medical Engineering and Technology. 33:249-256.
Farina et al. (1994) "Illuminant invariant calibration of thermochromic liquid-crystals," Exp. Therm. Fluid. Sci. 9:1-12.
Fiala et al. (1999) "computer model of human thermoregulation for a wide range of environmental conditions: The passive system," J. App. Physiol. 87:1957-1972.
Flammer et al. (2012) "The assessment of endothelial function: from research into clinical practice," Circulation. 126:753-767.
Fonseca et al. (2002) "Wireless micromachined ceramic pressure sensor for high-temperature application," J. Microelectromech. Syst. 11:337-343.
Fujikawa et al. (2009) "Measurement of hemodynamics during postural changes using a new wearable cephalic laser blood flowmeter," Circ. J. 73:1950-1955.
Gao et al. (Sep. 19, 2014) "Epidermal photonic devices for quantitative imaging of temperature and thermal transport characteristics of the skin," Nat. Commun. 5:4938.
Gorbach et al. (2012) "Infrared imaging of nitric oxide-mediated blood flow in human sickle cell disease," Microvasc. Res. 84:262-269.
Guidotti et al. (2008) "The interpretation of trace element analysis in body fluids," Indian J. Med. Res. 128:524-532.
Guinovart et al. (Sep. 26, 2013) "A potentiometric tattoo sensor for monitoring ammonium in sweat," Analyst. 138:7031-7038.
Gustafsson (1991) "Transient plane source techniques for thermal conductivity and thermal diffusivity measurements of solid materials," Review of Scientific Instruments. 62:797-804.
Hamraoui et al. (2002) "Analytical Approach for the Lucas-Washburn Equation," J. Colloid Interf. Sci. 250:415-421.
Harpster et al. (2002) "A passive wireless integrated humidity sensor," Sens. Actuators A. 95:100-107.
Hassan et al. (2001) "Observation of skin thermal inertia distribution during reactive hyperaemia using a single-hood measurement system," Physiol. Meas. 22:187-200.
Heikenfeld (Oct. 22, 2014) "Sweat Sensors Will Change How Wearables Track Your Health," IEEE Spectrum. Accessible on the Internet at URL: http://spectrum.ieee.org/biomedical/diagnostics/sweat-sensors-will-change-how-wearables-track-your-health. [Last Accessed Feb. 27, 2015] 4 pgs.
Higurashi et al. (2003) "An integrated laser blood flowmeter," Journal of Lightwave Technology. 21:591-595.
Holowatz et al. (2008) "The human cutaneous circulation as a model of generalized microvascular function," J. App. Physiol. 105:370-372.
Hu et al. (2006) "Human body fluid proteome analysis," Proteomics. 6(23):6326-53.
Huang et al. (2007) "Predictive value of reactive hyperemia for cardiovascular events in patients with peripheral arterial disease undergoing vascular surgery," Arterioscl. Throm. Vasc. 27:2113-2119.
Huang et al. (Apr. 6, 2014) "Stretchable, Wireless Sensors and Functional Substrates for Epidermal Characterization of Sweat," Small. 10(15):3083-3090.
Huang et al. (May 31, 2013) "Epidermal impedance sensing sheets for precision hydration assessment and spatial mapping," IEEE Trans. Biomed. Eng. 60(10):2848-57.
Ikeda et al. (1997) "Influence of thermoregulatory vasomotion and ambient temperature variation on the accuracy of core-temperature estimates by cutaneous liquid crystal thermometers," Anesthesiology. 86:603-612.
Ikeda et al. (1998) "Local radiant heating increases subcutaneous oxygen tension," Am. J. Surg. 175:33-37.
Intaglietta (1972) "On-line measurement of microvascular dimensions by television microscopy," J. Appl. Physiol. 32:546-551.
Ireland et al. (1987) "The response-time of a surface thermometer employing encapsulated thermochromic liquid-crystals," J. Phys. E. Sci. Instrum. 20:1195-1199.
Ishibashi et al. (2006) "Short duration of reactive hyperemia in the forearm of subjects with multiple cardiovascular risk factors," Circ. J. 70:115-123.
Jang et al. (Sep. 3, 2014) "Rugged and breathable forms of stretchable electronics with adherent composite substrates for transcutaneous monitoring," Nat. Commun. 5:4779.
Jansky et al. (2003) "Skin temperature changes in humans induced by local peripheral cooling," J. Therm. Biol. 28:429-437.
Jia et al. (Jul. 5, 2013) "Electrochemical tattoo biosensors for real-time noninvasive lactate monitoring in human perspiration," Anal. Chem. 85(14):6553-60.
Jin et al. (2012) "A feasible method for measuring the blood flow velocity in superficial artery based on the laser induced dynamic thermography," Infrared Physics and Technology. 55:462-468.
Kakade et al. (2009) "Accurate heat transfer measurements using thermochromic liquid crystal. Part 1: Calibration and characteristics of crystals," Int. J. Heat. Fluid Fl. 30:939-949.
Kaltenbrunner et al. (Jul. 25, 2013) "An ultra-lightweight design for imperceptible plastic electronics," Nature. 499:458-463.
Kathirgamanathan et al. (2009) "Delineation of distal ulnar nerve anatomy using ultrasound in volunteers to identify an optimum approach for neural blockade," Eur. J. Anaesth. 26:43-46.
Kehoe et al. (Aug. 9, 2013) "Introducing Colorimetric Analysis with Camera Phones and Digital Cameras: An Activity for High School or General Chemistry," J. Chem. Educ. 90:1191-1195.
Kennedy et al. (2009) "A Comparative Review of Thermography as a Breast Cancer Screening Technique," Integr. Cancer Ther. 8:9-16.
Kerr (2004) "Review of the effectiveness of infrared thermal imaging (thermography) for population screening and diagnostic testing of breast cancer," NZHTA Tech Brief Series. vol. 3. No. 3. pp. 1-49.

(56) References Cited

OTHER PUBLICATIONS

Khodagholy et al. (2012) "Organic electrochemical transistor incorporating an ionogel as a solid state electrolyte for lactate sensing," J. Mater. Chem. 22:4440-4443.
Kim et al. (2011) "Epidermal Electronics," Science. 333:838-843.
Kim et al. (2012) "Flexible and stretchable electronics for biointegrated devices," Annu. Rev. Biomed. Eng. 14:113-128.
Kim et al. (Nov. 3, 2014) "Epidermal Electronics with Advanced Capabilities in Near-Field Communication," Small. 11(8):906-912.
Klosowicz et al. (2001) "Liquid-crystal thermography and thermovision in medical applications," Proc. SPIE 4535, Optical Sensing for Public Safety, Health, and Security. 4535:24-29.
Kodzwa et al. (2007) "Angular effects on thermochromic liquid crystal thermography," Exp. Fluids. 43:929-937.
Kohler et al. (1998) "Diagnostic value of duplex ultrasound and liquid crystal contact thermography in preclinical detection of deep vein thrombosis after proximal femur fractures," Arch. Orthop. Trauma Surg. 117:39-42.
Kramer et al. (2009) "Increased pain and neurogenic inflammation in mice deficient of neutral endopeptidase," Neurobiol. Dis. 35(2):177-83.
Kvandal et al. (2006) "Low-frequency oscillations of the laser Doppler perfusion signal in human skin," Microvascular Research. 72:120-127.
Lacour et al. (2004) "Design and performance of thin metal film interconnects for skin-like electronic circuits," IEEE Electr. Device. Lett. 25:179-181.
Larranaga et al. (2012) "Heat Stress," In; Patty's Toxicology. 98:37-78.
Less et al. (1991) "Microvascular architecture in a mammary carcinoma: branching patterns and vessel dimensions," Cancer Research. 51:265-273.
Li et al. (2004) "Stretchability of thin metal films on elastomer substrates," Appl. Phys. Lett. 85:3435-3437.
Liao et al. (2012) "A 3-muhboxW CMOS Glucose Sensor for Wireless Contact-Lens Tear Glucose Monitoring," IEEE J. Solid State Circuits. 47:335-344.
Lindner (2004) "Microbubbles in medical imaging: Current applications and future directions," Nature Reviews Drug Discovery. 3:527-532.
Lossius et al. (1993) "Fluctuations in blood-flow to acral skin in humans-connection with heart-rate and blood-pressure variability," J. Physiol. 460:641-655.
Lu et al. (2012) "A thermal analysis of the operation of microscale, inorganic light-emitting diodes," Proceedings of the Royal Society A. 468:3215-3223.
Lu et al. (2012) "Highly Sensitive Skin-Mountable Strain Gauges Based Entirely on Elastomers," Adv. Funct. Mater. 22:4044-4050.
Lymberis (2010) "Advancced Wearable Sensors and Systems Enabling Personal Applications," In; Lecture Notes in Electrical Engineering: Wearable and Autonomous Biomedical Devices and Systems for Smart Environment. Eds.: Lay-Ekuakille et al. vol. 75. Springer. pp. 237-257.
Mangos et al. (1967) "Sodium Transport: Inhibitory Factor in Sweat of Patients with Cystic Fibrosis," Science. 158:135-136.
Mannsfeld et al. (2010) "Highly sensitive flexible pressure sensors with microstructured rubber dielectric layers," Nat. Mater. 9:859-864.
Marceau et al. (1983) "Pharmacology of kinins: their relevance to tissue injury and inflammation," Gen. Pharmacol. 14(2):209-29.
Martinez et al. (2007) "Patterned Paper as a Platform for Inexpensive, Low-Volume, Portable Bioassays," Angewandte Chemie International Edition. 46(8):1318-1320.
Martinez et al. (2008) "Simple Telemedicine for Developing Regions: Camera Phones and Paper-Based Microfluidic Devices for Real-Time, Off-Site Diagnosis," Analytical Chemistry. 80(10):3699-3707.
Martinez et al. (2010) "Diagnostics for the Developing World: Microfluidic Paper-Based Analytical Devices," Analytical Chemistry. 82(1):3-10.

Martinsen et al. (1999) "Measuring depth depends on frequency in electrical skin impedance measurements," Skin Research and Technology. 5(3):179-181.
Matzeu et al. (May 2015) "Advances in wearable chemical sensor design for monitoring biological fluids," Sensors and Actuators B. 211:403-418.
Mayrovitz et al. (2002) "Inspiration-induced vascular responses in finger dorsum skin," Microvasc. Res. 63:227-232.
McCartney et al. (2007) "Ultrasound Examination of Peripheral Nerves in the Forearm," Reg. Anesth. Pain Med. 32:434-439.
McDonald et al. (2002) "Poly(dimethylsiloxane) as a Material for Fabricating Microfluidic Devices," Accounts of Chemical Research. 35(7):491-499.
Mishra et al. (2005) "The Relevance of Sweat Testing for the Diagnosis of Cystic Fibrosis in the Genomic Era," Clin. Biochem. Rev. 26(4):135-153.
Moyer et al. (2012) "Correlation Between Sweat Glucose and Blood Glucose in Subjects with Diabetes," Diabetes Technology & Therapeutics. 14(5):398-402.
Mukerjee et al. (2004) "Microneedle Array for Transdermal Biological Fluid Extraction and in Situ Analysis," Sensors and Actuators A: Physical. 114(2-3):267-275.
Newman et al. (1984) "Liquid-crystal thermography in the evaluation of chronic back pain—a comparative-study," Pain. 20:293-305.
Nilsson et al. (1980) "Evaluation of a laser Doppler flowmeter for measurement of tissue blood flow," IEEE Transactions on Biomedical Engineering. 27:597-604.
Nitzan et al. (1986) "Theoretical-Analysis of the Transient Thermal Clearance Method for Regional Blood-Flow Measurement," Medical & Biological Engineering & Computing. 24:597-601.
Nitzan et al. (1988) "Simultaneous measurement of skin blood flow by the transient thermal-clearance method and laser Doppler flowmetry," Medical & Biological Engineering & Computing. 26:407-410.
Nopper et al. (2010) "Wireless Readout of Passive LC Sensors," IEEE Trans. Instrum. Meas. 59:2450-57.
Nordin (1990) "Sympathetic discharges in the human supraorbital nerve and their relation to sudo- and vasomotor responses," J. Physiol. 423:241-255.
Oberg (1990) "Laser-Doppler flowmetry," Critical Reviews in Biomedical Engineering. 18(2):125-163.
Oncescu et al. (Jun. 19,2013) "Smartphone based health accessory for colorimetric detection of biomarkers in sweat and saliva," Lab Chip 13:3232-3238.
Paranjape et al. (2003) A PDMS dermal patch for non-intrusive transdermal glucose sensing. Sens. Actuat. A. 104:195-204.
Park et al. (2008) "The effect of heat on skin permeability," Int. J. Pharm. 359(1-2):94-103.
Pelrine et al. (2000) "High-field deformation of elastomeric dielectrics for actuators," Mater. Sci. Eng. C. 11:89-100.
Petrie et al. (1988) "How reproducible is bilateral forearm plethysmography?" British Journal of Clinical Pharmacology. 45:131-139.
Petrofsky (2012) "Resting blood flow in the skin: does it exist, and what is the influence of temperature, aging, and diabetes?" Journal of Diabetes Science and Technology. 6:674-685.
Pochaczevsky (1983) "The value of liquid-crystal thermography in the diagnosis of spinal root compression syndromes," Orthop. Clin. N. Am. 14:271-288.
Pochaczevsky et al. (1979) "Vacuum contoured, liquid-crystal, dynamic breast thermoangiography as an aid to mammography in the detection of breast-cancer," Clin. Radiol. 30:405-411.
Pochaczevsky et al. (1982) "Liquid crystal contact thermography of deep venous thrombosis," Am. J. Roentgenol. 138:717-723.
Pochaczevsky et al. (1982) "Liquid-crystal thermography of the spine and extremities—its value in the diagnosis of spinal root syndromes," J. Neurosurg. 56:386-395.
Polliack et al. (1997) "Sweat analysis following pressure ischaemia in a group of debilitated subjects," J. Rehabil. Res. Dev. 34(3):303-308.
Powers et al. (2009) :Rapid Measurement of Total Body Water to Facilitate Clinical Decision Making in Hospitalized Elderly Patients, J. Gerontol. A. Biol. Sci. Med. Sci. 64(6):664-9.

(56) References Cited

OTHER PUBLICATIONS

Prausnitz et al. (2008) "Transdermal drug delivery," Nature Biotechnology. 26(11):1261-1268.
Raamat et al. (2002) "Simultaneous recording of fingertip skin blood flow changes by multiprobe laser Doppler flowmetry and frequency-corrected thermal clearance," Microvascular Research. 64:214-219.
Rao et al. (2010) "Calibrations and the measurement uncertainty of wide-band liquid crystal thermography," Meas. Sci. Technol. 21(1):015105. pp. 1-8.
Ritz (2001) "Bioelectrical impedance analysis estimation of water compartments in elderly diseased patients: the source study," J. Gerontol. 56:M344-M348.
Robertson et al. (2010) "Variation in epidermal morphology in human skin at different body sites as measured by reflectance confocal microscopy," Acta Derm. Venereol. 90(4):368-73.
Roda et al. (Dec. 21, 2014) "A 3D-printed device for a smartphone-based chemilumin-escence biosensor for lactate in oral fluid and sweat," Analyst. 139:6494-6501.
Rogers et al. (2010) "Materials and mechanics for stretchable electronics," Science. 327:1603-1607.
Rose et al. (Nov. 11, 2014) "Adhesive RFID Sensor Patch for Monitoring of Sweat Electrolytes," IEEE Trans. Biomed. Eng. 62(6):1457-65.
Rosenbaum (2001) "Thermal properties and characterization of methane hydrates," M.S. thesis, University of Pittsburgh.
Sabatino et al. (2000) "A high-accuracy calibration technique for thermochromic liquid crystal temperature measurements," Exp. Fluids. 28:497-505.
Sage (2011) "Thermochromic liquid crystals," Liquid Crystals. 38:1551-1561.
Salvo et al. (2010) "A Wearable Sensor for Measuring Sweat Rate," IEEE Sens. J. 10:1557-1558.
Sandby-Moller et al. (2003) "Epidermal thickness at different body sites: Relationship to age, gender, pigmentation, blood content, skin type and smoking habits," Acta. Derm. Venereol. 83:410-413.
Sangkatumvong et al. (2011) "Peripheral vasoconstriction and abnormal parasympathetic response to sighs and transient hypoxia in sickle cell disease," Am. J. Respir. Crit. Care Med. 184:474-481.
Schrope et al. (1993) "Second harmonic ultrasonic blood perfusion measurement," Ultrasound in Medicine and Biology. 19:567-579.
Schwartz et al. (May 14, 2013) "Flexible polymer transistors with high pressure sensitivity for application in electronic skin and health monitoring," Nat. Commun. 4:1859. pp. 1-8.
Sekitani et al. (2008) "A rubberlike stretchable active matrix using elastic conductors," Science 321:1468-1472.
Sekitani et al. (2009) "Organic nonvolatile memory transistors for flexible sensor arrays," Science. 326:1516-1519.
Shen et al. (2006) "A genomewide scan for quantitative trait loci underlying areal bone size variation in 451 Caucasian families," J. Med. Genet. 43:873-880.
Shih et al. (2002) "Effect of effective tissue conductivity on thermal dose distributions of living tissue with directional blood flow during thermal therapy," International Communications in Heat and Mass Transfer. 29:115-126.
Shima et al. (1996) "An anatomical study on the forearm vascular system," J. Cranio. Maxill. Surg. 24:293-299.
Shpilfoygel et al. (2000) "X-ray videodensitometric methods for blood flow and velocity measurement: a critical review of literature," Medical Physics. 27:2008-2023.
Sieg et al. (2003) "Subcutaneous fat layer in different donor regions used for harvesting microvascular soft tissue flaps in slender and adipose patients," International Journal of Oral and Maxillofacial Surgery. 32:544-547.
Sikirzhytski et al. (2010) "Discriminant Analysis of Raman Spectra for Body Fluid Identification for Forensic Purposes," Sensors. 10(4):2869-2884.
Someya et al. (2005) "Conformable, flexible, large-area networks of pressure and thermal sensors with organic transistor active matrixes," Proc. Natl. Acad. Sci. USA. 102:12321-12325.
Son et al. (Mar. 30, 2014) "Multifunctional wearable devices for diagnosis and therapy of movement disorders," Nat. Nanotechnol. 9:397-404.
Sondheimer (1952) "The Mean Free Path of Electrons in Metals," Adv. Phys. 1:1-42.
Song et al. (1988) "A combined macro and microvascular model for whole limb heat transfer," J. Biomech. Eng. 110:259-268.
Stasiek et al. (2002) "Thermochromic liquid crystals applied for heat transfer research," Proceedings of the SPIE, vol. 4759:374-383.
Strommer et al. (2007) "Ultra-low Power Sensors with Near Field Communication for Mobile Applications," In; Wireless Sensor and Actor Networks. vol. 248. Springer. pp. 131-142.
Su et al. (2011) "A polymer stacking process with 3D electrical routings for flexible temperature sensor array and its heterogeneous integration," In; The 16th International Solid-State Sensors, Actuators and Microsystems Conference (Transducers), 2011. pp. 1396-1399.
Sun et al. (2009) "Inorganic islands on a highly stretchable polyimide substrate," J. Mater. Res. 24:3338-3342.
Sutera et al. (1993) "The History of Poiseuille's Law," Annu. Rev. Fluid Mech. 25:1-20.
Suzuki (1998) "Nickel and gold in skin lesions of pierced earlobes with contact dermatitis. A study using scanning electron microscopy and x-ray microanalysis," Arch. Dermatol. Res. 290:523-527.
Tee et al. (2012) "An electrically and mechanically self-healing composite with pressure- and flexion-sensitive properties for electronic skin applications," Nat. Nanotechnol. 7:825-832.
Ten Berge et al. (2011) "Perforating Veins: An Anatomical Approach to Arteriovenous Fistula Performance in the Forearm," European Journal of Vascular and Endovascular Surgery. 42:103-106.
Thalayasingam et al. (1989) "Thermal Clearance Blood-Flow Sensor Sensitivity, Linearity and Flow Depth Discrimination," Medical & Biological Engineering & Computing. 27:394-398.
Thomas et al. (1989) "Liquid-crystal thermography and c-reactive protein in the detection of deep venous thrombosis," Bri. Med. J. 299:951-952.
Thoresen et al. (1980) "Skin blood-flow in humans as a function of environmental-temperature measured by ultrasound," Acta Physiol. Scand. 109:333-341.
Togawa et al. (1994) "Non-contact imaging of thermal properties of the skin," Physiological Measurement. 15:291-298.
Van De Staak et al. (1968) "Measurements of Thermal Conductivity of Skin as an Indication of Skin Blood Flow," J. Invest. Dermatol. 51:149-154.
Varkey et al. (2011) "Human motion recognition using a wireless sensor-based wearable system," Pers. Ubiquit. Comput. 16(7):897-910.
Virkler et al. (2009) "Analysis of body fluids for forensic purposes: From laboratory testing to non-destructive rapid confirmatory identification at a crime scene," Forensci. Sci. Int. 188(1-3):1-17.
Wang et al. (2012) "Mechanics of Epidermal Electronics," Journal of Applied Mechanics. 79:031022.
Wang et al. (Jul. 21, 2013) "User-interactive electronic-skin for instantaneous pressure visualization," Nat. Mater. 12:899-904.
Wardell et al. (1993) "Laser Doppler perfusion imaging by dynamic light scattering," IEEE Transactions on Biomedical Engineering. 40:309-316.
Washburn (1921) "The Dynamics of Capillary Flow," Phys. Rev. 17(3):273.
Webb et al. (Feb. 6, 2015) "Thermal transport characteristics of human skin measured in vivo using ultrathin conformal arrays of thermal sensors and actuators," PLoS One. 10:e0118131. pp. 1-17.
Webb et al. (Oct. 30, 2015) "Epidermal devices for noninvasive, precise, and continuous mapping of macrovascular and microvascular blood flow," Sci Adv. 1(9):e1500701. pp. 1-13.
Webb et al. (Sep. 15, 2013) "Ultrathin conformal devices for precise and continuous thermal characterization of human skin," Nat. Mater. 12:938-944.
Weber et al. (2001) "Facilitated neurogenic inflammation in complex regional pain syndrome," Pain. 91(3):251-7.
Werner et al. (1992) "Measurement of the thermal diffusivity of human epidermis by studying thermal wave propagation," Physics in Medicine and Biology. 37:21-35.

(56) References Cited

OTHER PUBLICATIONS

Wilkinson et al. (2001) "Venous occlusion plethysmography in cardiovascular research: methodology and clinical applications," British Journal of Clinical Pharmacology. 52:631-646.

Windmiller et al. (Sep. 7, 2012) "Wearable Electrochemical Sensors and Biosensors: A Review," Electroanalysis. 25(1):29-46.

Wright et al. (2006) "Non-invasive methods and stimuli for evaluating the skin's microcirculation," Journal of Pharmacological and Toxicological Methods. 54:1-25.

Xiao et al. (1997) "Optothermal measurement of stratum corneum thickness and hydration-depth profile," In; The Proc. SPIE 2970, Lasers in Surgery: Advanced Characterization, Therapeutics, and Systems VII., 12 pgs.

Xiao et al. (2010) "Opto-thermal in-vivo skin hydration measurements—a comparison study of different measurement techniques," J. Phys. Conf. Ser. 214:012026. pp. 1-4.

Xiao et al. (2010) "Thermal diffusivity effect in opto-thermal skin measurements," J. Phys. Conf. Ser. 214:012027. pp. 1-4.

Xu et al. (Apr. 4, 2014) "Soft Microfluidic Assemblies of Sensors, Circuits, and Radios for the Skin," Science. 344:70-74.

Yamamoto et al. (1976) "Electrical properties of the epidermal stratum corneum," Medical and Biological Engineering. 14(2):151-158.

Yeo et al. (Feb. 26, 2013) "Multifunctional Epidermal Electronics Printed Directly Onto the Skin," Advanced Materials. 25:2773-2778.

Yu et al. (2012) "An Interstitial Fluid Transdermal Extraction System for Continuous Glucose Monitoring," J. Microelectromech. Syst. 21(4):917-925.

Zakharov et al. (2009) "A wearable diffuse reflectance sensor for continuous monitoring of cutaneous blood content," Physics in Medicine and Biology. 54:5301-5320.

Zamir et al. (2012) "Intrinsic microvasculature of the sciatic nerve in the rat," J. Peripher. Nerv. Syst. 17(4):377-84.

Zeng et al. (Jun. 18, 2014) "Fiber-Based Wearable Electronics: A Review of Materials, Fabrication, Devices, and Applications," Adv. Mater. 26:5310-5336.

International Search Report with Written Opinion corresponding to International Patent Application No. PCT/US2015/044573, dated Nov. 19, 2015, 8 pgs.

International Search Report with Written Opinion corresponding to International Patent Application No. PCT/US2015/044588, dated Jan. 7, 2016, 9 pgs.

International Search Report with Written Opinion corresponding to International Patent Application No. PCT/US2015/044638, dated Apr. 21, 2016, 23 pgs.

International Search Report with Written Opinion corresponding to International Patent Application No. PCT/US2015/053452, dated Mar. 10, 2016, 10 pgs.

Supplementary European Search Report corresponding to European Patent Application No. 15831510.1, dated Mar. 8, 2018.

Chinese Second Office Action with English translation, dated Nov. 20, 2019, in Chinese Patent Application No. 2015800551825, 29 pages.

Japanese Patent Office, "Notice of Reasons for Rejection" with English translation, dated Sep. 3, 2019, in Japanese Patent Application No. P2017-507709, 14 pp.

Supplementary Partial European Search Report, completed May 11, 2018, corresponding to European Application No. 15831517.

\* cited by examiner

B

| Type | Channel Width (mm) | Radius of Neutral Circle (mm) | Area (mm²) |
|---|---|---|---|
| A | 1.00 | 10.93 | 67.70 |
| B | 1.58 | 10.93 | 106.96 |
| C | 1.00 | 17.31 | 107.63 |
| D | 1.00 | 10.93 | 107.17 |

DEVICES AND RELATED METHODS FOR EPIDERMAL CHARACTERIZATION OF BIOFLUIDS

CROSS-REFERENCE TO RELATED APPLICATIONS

This application is a U.S. National Stage Application under 35 U.S.C. § 371 of International Application No. PCT/US2015/044638, filed Aug. 11, 2015, which claims the benefit of and priority to U.S. Provisional Patent Application No. 62/035,823, filed Aug. 11, 2014, and U.S. Provisional Patent Application No. 62/142,877, filed Apr. 3, 2015, each of which is hereby incorporated by reference in its entirety to the extent not inconsistent herewith.

STATEMENT REGARDING FEDERALLY SPONSORED RESEARCH OR DEVELOPMENT

Not Applicable.

BACKGROUND

Emerging wearable sensor technologies offer attractive solutions for continuous, personal health/wellness assessment, forensic examination, patient monitoring and motion recognition. Recent advances in epidermal electronics provide classes of skin-mounted sensors and associated electronics in physical formats that enable intimate contact with the skin for long-term, reliable health monitoring.

An important measurement mode in such devices may involve the analysis of body fluids (e.g., blood, interstitial fluid, sweat, saliva, and tear), to gain insights into various aspects of physiological health. Such function in wearable sensors, generally, and epidermal electronics in particular, is relatively unexplored. Existing devices either use complex microfluidic systems for sample handling or involve purely concentration-based measurement without sample collection and storage, or access to parameters related to quantity and rate. In addition, mechanical fixtures, straps and/or tapes that are typically required to maintain contact of these devices with the skin do not lend themselves well to continuous, long term monitoring without discomfort.

SUMMARY OF THE INVENTION

Skin-mounted or epidermal devices and methods for monitoring biofluids are disclosed. The devices comprise a functional substrate that is mechanically and/or thermally matched to skin to provide durable adhesion for long-term wear. The functional substrates allow for the microfluidic transport of biofluids from the skin to one or more sensors that measure and/or detect biological parameters, such as rate of biofluid production, biofluid volume, and biomarker concentration. Sensors within the devices may be mechanical, electrical or chemical, with colorimetric indicators being observable by the naked eye or with a portable electronic device (e.g., a smartphone). By monitoring changes in an individual's health state over time, the disclosed devices may provide early indications of abnormal conditions.

Epidermal devices disclosed herein may be used to monitor parameters such as temperature, pressure, electric potential, impedance and biomarker concentration.

Analytes that may be detected by the disclosed devices include but are not limited to iron ion, copper ion, chromium ion, mercury ion, sodium ion, potassium ion, calcium ion, chloride ion, hydronium, hydroxide, ammonium, bicarbonate, urea, lactate, glucose, creatinine, ethanol, ketone, nitrite, nitrate, uric acid, glutathione, blood urea nitrogen (BUN), human serum albumin (HSA), high-sensitivity C-reactive protein (hs-CRP), interleukin 6 (IL-6), cholesterol, brain naturiuretic peptide (BNP) and glycoprotein.

TABLE 1

Examples of biofluids and their respective sampling methods

| Biological Fluid | Sampling Method |
| --- | --- |
| Saliva | Non-invasive |
| Sweat | |
| Gingival crevicular fluid | |
| Tears | |
| Interstitial fluid | Micro-needle |
| Blood | Reverse iontophoresis |
| | Thermal ablation |

TABLE 2

Potential biomarkers for quantitative colorimetric detection

| Colorimetric detection reagent/scheme | Analyte biomarkers |
| --- | --- |
| Chromogen | Iron ion, copper ion, chloride ion, pH ($H^+$ and $OH^-$), bicarbonate |
| Enzymatic reaction | Urea, lactate, glucose, creatinine, ethanol, ketone, nitrite/nitrate, uric acid, glutathione, blood urea nitrogen (BUN) |
| Immunoassay | Human serum albumin (HSA), high-sensitivity C-reactive protein (hs-CRP), interleukin 6 (IL-6), cholesterol, brain naturiuretic peptide (BNP), glycoprotein |

The disclosed devices may mobilize and access biofluids by mechanical, electrical and/or thermal mechanisms including but not limited to surface wicking, microneedle extraction, reverse iontophoresis and/or thermal microablation.

In an embodiment, a device comprises at least one microneedle or an array of microneedles for accessing interstitial fluid or blood. Microneedles may, for example, be fabricated from polymeric materials, silicon or glass using known micromachining techniques. Some methods for making and using microneedles and microneedle arrays are disclosed, for example, in E. V. Mukerjee, "Microneedle array for transdermal biological fluid extraction and in situ analysis," Sensors and Actuators A, 114 (2004) 267-275. In an embodiment, a microneedle or microneedle array may be disposed at a surface of an epidermal device, for example, at a microchannel opening.

In an aspect, a device for monitoring a biofluid comprises a functional substrate that is mechanically matched to skin; wherein the functional substrate provides for microfluidic transport of the biofluid; and at least one sensor supported by the functional substrate.

In an aspect, a device for monitoring a biofluid comprises a functional substrate that is thermally matched to skin; wherein the functional substrate provides for microfluidic transport of the biofluid; and at least one sensor supported by the functional substrate.

In an aspect, a device for monitoring a biofluid comprises a functional substrate providing for microfluidic transport of the biofluid through one or more microfluidic channels each having a substantially uniform lateral dimension; and at least one sensor supported by the functional substrate.

In an embodiment, a device for monitoring a biofluid further comprises a component for extracting interstitial fluid or blood from a subject. For example, the component for extracting interstitial fluid or blood may be selected from a microneedle component, a reverse iontophoresis component and a thermal microabrasion component.

In an embodiment, a functional substrate is an elastomeric substrate. In an embodiment, the functional substrate is substantially colorless and substantially transparent. In an embodiment, the functional substrate has a modulus less than or equal to 100 MPa and optionally in some embodiments less than or equal to 10 MPa. In an embodiment, the functional substrate has a modulus selected from a range of 10 kPa to 10 MPa and in some embodiments selected from a range of 100 kPa to 1 MPa. In an embodiment, the functional substrate has a thickness selected from a range of 500 μm to 2 mm and in some embodiments selected from a range of 500 μm to 1 mm. In some embodiments, the functional substrate is selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA) and polycarbonate. In some embodiments, the functional substrate has a dielectric constant greater than or equal to 2.0. In some embodiments, the functional substrate has a dielectric constant selected from a range of 2.20 to 2.75. In some embodiments, the functional substrate has lateral dimensions or a diameter less than or equal to 700 mm. In some embodiments, the functional substrate has a permeability for the biofluid greater than or equal to 0.2 g/h m$^2$. In some embodiments, the functional substrate has a coefficient of thermal expansion selected from a range of 1/° C. ($\times 10^{-6}$) to 3/° C. ($\times 10^{-4}$). In some embodiments, the functional substrate has a porosity greater than or equal to 0.5.

In some embodiments, microfluidic transport is spontaneous microfluidic transport via capillary force.

In some embodiments, a device for monitoring a biofluid comprises at least one microfluidic channel having a substantially uniform lateral dimension. For example, the microfluidic channel may have a length selected from a range of 1 mm to 7 cm and optionally in some embodiments selected from a range of 1 cm to 5 cm. In some embodiments, a microfluidic channel has a width selected from a range of 100 μm to 1 mm and optionally in some embodiments selected from a range of 200 μm to 700 μm.

In some embodiments, the biofluid is selected from the group consisting of sweat, tears, saliva, gingival crevicular fluid, interstitial fluid, blood and combinations thereof.

In some embodiments, a sensor of the device is a non-pH colorimetric indicator. In some embodiments, the sensor of the device may comprise an electrical sensor, a chemical sensor, a biological sensor, a temperature sensor, an impedance sensor, an optical sensor, a mechanical sensor or a magnetic sensor. In some embodiments, the sensor of the device is an LC resonator.

In some embodiments, the device further comprises an actuator. For example, the actuator may generate electromagnetic radiation, acoustic energy, an electric field, a magnetic field, heat, a RF signal, a voltage, a chemical change or a biological change. In some embodiments, the actuator comprises a heater, a reservoir containing a chemical agent capable of causing a chemical change or a biological change, a source of electromagnetic radiation, a source of an electric field, a source of RF energy or a source of acoustic energy.

In some embodiment, the device further comprises a transmitter, receiver or transceiver. In some embodiments, the device further comprises at least one coil. For example, the at least one coil may be a near-field communication coil or an inductive coil. In some embodiments, the at least one coil comprises a serpentine trace.

In some embodiments, the sensor is a colorimetric indicator. For example, the colorimetric indicator may be disposed within a cavity of the functional substrate. The cavity may be connected to an opening at a surface of the functional substrate by a microfluidic channel.

In some embodiments, the colorimetric indicator changes color in response to an analyte in the biofluid. In some embodiments, the colorimetric indicator is embedded in a matrix material selected from the group consisting of filter paper, polyhydroxyethylmethacrylate hydrogel (pHEMA), agarose gel, sol-gel and combinations thereof. In some embodiments, the colorimetric indicator comprises a cobalt dichloride salt. In some embodiments, the colorimetric indicator comprises a chemical selected from the group consisting of glucose oxidase, peroxidase, potassium iodide and combinations thereof. In some embodiments, the colorimetric indicator comprises a chemical selected from lactate dehydrogenase, diaphorase, formazan dyes and combinations thereof. In some embodiments, the colorimetric indicator comprises a 2,4,6-tris(2-pyridiyl)-s-triazine (TPTZ) complexed with mercury ion or iron ion. In some embodiments, the colorimetric indicator comprises a 2,2'-bicinchoninic acid. In some embodiments, the colorimetric indicator comprises a 1,10-phenanthroline. In some embodiments, the colorimetric indicator comprises a universal pH indicator.

In some embodiments, the device is a skin-mounted sensor. In some embodiments, the skin-mounted sensor quantitatively and/or qualitatively monitors the biofluid of a subject.

In some embodiments, the device has a modulus and a thickness within a factor of 1000 of a modulus and a thickness of an epidermal layer of the skin of a subject, optionally for some embodiments a factor of 10 of a modulus and a thickness of an epidermal layer of the skin of a subject, and optionally for some embodiments a factor of 2 of a modulus and a thickness of an epidermal layer of the skin of a subject. In an embodiment, for example, the device has an average modulus equal to or less than 100 times, optionally equal to or less than 10 times, the average modulus of the skin at the interface.

In an embodiment, for example, the device has an average thickness less than or equal to 3000 microns, optionally for some embodiments less than or equal to 1000 microns. In an embodiment, for example, the device has an average thickness selected over the range of 1 to 3000 microns, optionally for some applications selected over the range of 1 to 1000 microns.

In some embodiments, the device has an average modulus less than or equal to 100 MPa, optionally for some embodiments less than or equal to 500 kPa, optionally for some embodiments less than or equal to 200 KPa, and optionally for some embodiments less than or equal to 100 KPa. In some embodiments, the device has an average modulus selected from a range of 0.5 kPa to 100 MPa, optionally for some embodiments 0.5 kPa to 500 kPa, and optionally for some embodiments 1 kPa to 100 kPa.

In some embodiments, the device has a net bending stiffness less than or equal to 1 mN m, optionally for some embodiments less than or equal to 1 nN m. In some embodiments, the device has a net bending stiffness selected from a range of 0.1 nN m to 1 N m, optionally for some embodiments selected from a range of 0.1 nN m to 1 mN m, and optionally for some embodiments selected from a range of 0.1 nN m to 1 nN m.

In some embodiments, the device has a footprint selected from a range of 10 mm² to 2000 cm², and optionally selected from a range of 300 mm² to 2000 cm².

In an aspect, a method of making a device for monitoring a biofluid comprises: providing a functional substrate that is mechanically matched to skin; wherein the functional substrate provides for microfluidic transport of the biofluid; and providing at least one sensor supported by the functional substrate.

In an aspect, a method of making a device for monitoring a biofluid comprises: providing a functional substrate that is thermally matched to skin; wherein the functional substrate provides for microfluidic transport of the biofluid; and providing at least one sensor supported by the functional substrate.

In an aspect, a method of making a device for monitoring a biofluid comprises: providing a functional substrate that provides for microfluidic transport of the biofluid through one or more microfluidic channels each having a substantially uniform lateral dimension; and providing at least one sensor supported by the functional substrate.

In an aspect, a method for monitoring a biofluid comprises: providing a device comprising a functional substrate that is mechanically matched to skin; wherein the functional substrate provides for microfluidic transport of the biofluid; and at least one sensor supported by the functional substrate; applying the device to the skin of a subject; and obtaining data from the at least one sensor; wherein the data provide quantitative and/or qualitative information about the biofluid of the subject.

In an aspect, a method for monitoring a biofluid comprises: providing a device comprising a functional substrate that is thermally matched to skin; wherein the functional substrate provides for microfluidic transport of the biofluid; and at least one sensor supported by the functional substrate; applying the device to the skin of a subject; and obtaining data from the at least one sensor; wherein the data provide quantitative and/or qualitative information about the biofluid of the subject.

In an aspect, a method for monitoring a biofluid comprises: providing a functional substrate that provides for microfluidic transport of the biofluid through one or more microfluidic channels each having a substantially uniform lateral dimension; and at least one sensor supported by the functional substrate; applying the device to the skin of a subject; and obtaining data from the at least one sensor; wherein the data provide quantitative and/or qualitative information about the biofluid of the subject.

DETAILED DESCRIPTION OF THE INVENTION

Figure 1:
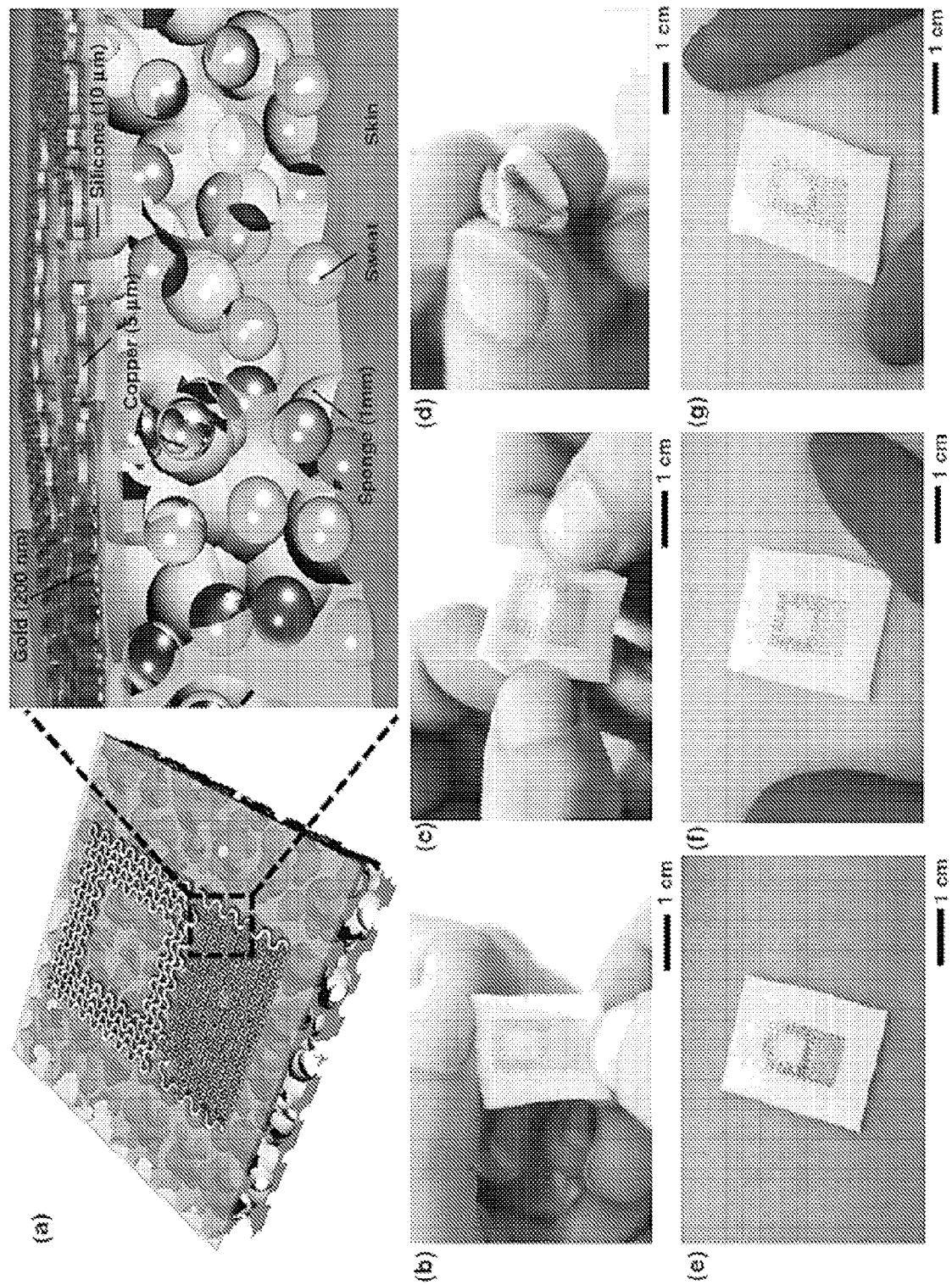
FIG. 1. (a) Schematic illustration of a passive wireless capacitive sensor designed for sensing of sweat from the surface of the skin. Pictures of a device in (b) longitudinal and (c) latitudinal states of deformation, and crumpled between the fingers (d). Pictures of a device mounted on the skin in (e) undeformed, (f) uniaxially stretched and (g) biaxially stretched configurations.

In general, the terms and phrases used herein have their art-recognized meaning, which can be found by reference to standard texts, journal references and contexts known to those skilled in the art. The following definitions are provided to clarify their specific use in the context of the invention.

"Functional substrate" refers to a substrate component for a device having at least one function or purpose other than providing mechanical support for a component(s) disposed on or within the substrate. In an embodiment, a functional substrate has at least one skin-related function or purpose. In an embodiment, a functional substrate of the present devices and methods exhibits a microfluidic functionality, such as providing transport of a bodily fluid through or within the substrate, for example via spontaneous capillary action or via an active actuation modality (e.g. pump, etc.). In an embodiment, a functional substrate has a mechanical functionality, for example, providing physical and mechanical properties for establishing conformal contact at the interface with a tissue, such as skin. In an embodiment, a functional substrate has a thermal functionality, for example, providing a thermal loading or mass small enough so as to avoid interference with measurement and/or characterization of a physiological parameter, such as the composition and amount of a biological fluid. In an embodiment, a functional substrate of the present devices and method is biocompatible and/or bioinert. In an embodiment, a functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another.

In some embodiments, a functional substrate that is mechanically matched to a tissue, such as skin, provides a conformable interface, for example, useful for establishing conformal contact with the surface of the tissue. Devices and methods of certain embodiments incorporate mechanically functional substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

In some embodiments, a mechanically matched functional substrate is characterized by one or more mechanical properties and/or physical properties that are within a specified factor of the same parameter for an epidermal layer of the skin, such as a factor of 10 or a factor of 2. In an embodiment, for example, a functional substrate has a Young's Modulus or thickness that is within a factor of 20, or optionally for some applications within a factor of 10, or optionally for some applications within a factor of 2, of a tissue, such as an epidermal layer of the skin, at the interface with a device of the present invention. In an embodiment, a mechanically matched functional substrate may have a mass or modulus that is equal to or lower than that of skin.

In some embodiments, a functional substrate that is thermally matched to skin has a thermal mass small enough that deployment of the device does not result in a thermal load on the tissue, such as skin, or small enough so as not to impact measurement and/or characterization of a physiological parameter, such as a characteristic of a biological fluid (e.g. composition, rate of release, etc.). In some embodiments, for example, a functional substrate that is thermally matched to skin has a thermal mass low enough such that deployment on skin results in an increase in temperature of less than or equal to 2 degrees Celsius, and optionally for some applications less than or equal to 1 degree Celsius, and optionally for some applications less than or equal to 0.5 degree Celsius, and optionally for some applications less than or equal to 0.1 degree Celsius. In some embodiments, for example, a functional substrate that is thermally matched to skin has a thermal mass low enough that is does not significantly disrupt water loss from the skin, such as avoiding a change in water loss by a factor of 1.2 or greater. Therefore, the device does not substantially induce sweating or significantly disrupt transdermal water loss from the skin.

In an embodiment, the functional substrate may be at least partially hydrophilic and/or at least partially hydrophobic.

In an embodiment, the functional substrate may have a modulus less than or equal to 100 MPa, or less than or equal to 50 MPa, or less than or equal to 10 MPa, or less than or equal to 100 kPa, or less than or equal to 80 kPa, or less than or equal to 50 kPa. Further, in some embodiments, the device may have a thickness less than or equal to 5 mm, or less than or equal to 2 mm, or less than or equal to 100 µm, or less than or equal to 50 µm, and a net bending stiffness less than or equal to 1 nN m, or less than or equal to 0.5 nN m, or less than or equal to 0.2 nN m. For example, the device may have a net bending stiffness selected from a range of 0.1 to 1 nN m, or 0.2 to 0.8 nN m, or 0.3 to 0.7 nN m, or 0.4 to 0.6 nN m.

A "component" is used broadly to refer to an individual part of a device.

"Sensing" refers to detecting the presence, absence, amount, magnitude or intensity of a physical and/or chemical property. Useful device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\Delta$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The invention can be further understood by the following non-limiting examples.

Example 1: Stretchable, Wireless Sensors and Functional Substrates for Epidermal Characterization of Sweat This Example introduces materials and architectures for ultrathin, stretchable wireless sensors that mount on functional elastomeric substrates for epidermal analysis of biofluids. Measurement of the volume and chemical properties of sweat via dielectric detection and colorimetry demonstrates some capabilities. Here, inductively coupled sensors comprising LC resonators with capacitive electrodes show systematic responses to sweat collected in microporous substrates. Interrogation occurs through external coils placed in physical proximity to the devices. The substrates allow spontaneous sweat collection through capillary forces, without the need for complex microfluidic handling systems. Furthermore, colorimetric measurement modes are possible in the same system by introducing indicator compounds into the depths of the substrates, for sensing specific components ($OH^-$, $H^+$, $Cu^+$, and $Fe^{2+}$) in the sweat. The complete devices offer Young's moduli that are similar to skin, thus allowing highly effective and reliable skin integration without external fixtures. Experimental results demonstrate volumetric measurement of sweat with an accuracy of 0.06 $\mu L/mm^2$ with good stability and low drift. Colorimetric responses to pH and concentrations of various ions provide capabilities relevant to analysis of sweat. Similar materials and device designs can be used in monitoring other body fluids.

1. Introduction

Emerging wearable sensor technologies offer attractive solutions for continuous, personal health/wellness assessment,[1,2] forensic examination[3] patient monitoring[4,5] and motion recognition.[6,7] Recent advances in epidermal electronics[8] provide classes of skin-mounted sensors and associated electronics in physical formats that enable intimate, conformal contact with the skin. The soft, non-irritating nature of this contact yields an interface that simultaneously provides high precision, accurate measurement of biophysiological parameters, such as temperature,[9] hydration,[10] strain,[11] and biopotential.[12] Such epidermal sensors are ultrathin, breathable and stretchable, with mechanical and thermal properties that closely match to the skin itself, to enable effective skin integration with minimum constraints on natural processes. The results provide unique capabilities in long-term, reliable health monitoring.

An important measurement mode in such devices may involve the analysis of body fluids (blood, interstitial fluid, sweat, saliva, and tear), to gain insights into various aspects of physiological health.[13-16] Such function in wearable sensors, generally, and epidermal electronics in particular, is relatively unexplored. Existing devices either use complex microfluidic systems for sample handling[17-20] or involve purely concentration-based measurement without sample collection and storage, or access to parameters related to quantity and rate.[21-23] In addition, mechanical fixtures, straps and/or tapes that are typically required to maintain contact of these devices with the skin do not lend themselves well to continuous, long term monitoring without discomfort.[24] In the following, a set of materials and device architectures that provide advanced capabilities in this area is reported. The key concept involves the use of functional soft substrates to serve as a means for microfluidic collection, analysis and presentation to co-integrated electronic sensors and/or external camera systems. The pores of these substrates spontaneously fill with body fluids that emerge from the skin, where they induce colorimetric changes in the substrate and alter the radio frequency characteristics of integrated electrical antenna structures. The results offer valuable insights into the properties and volume of sweat, and their relationships to fluctuations in body temperature,[25] fluid and electrolyte balance,[26] and disease state.[27] The devices also eliminate the need for direct skin-electrode contacts, thereby minimizing irritation that can be caused by contact between the skin and certain metals,[28] while at the same time enabling repeated use of a single device with minimal noise induced by motion artifacts. The sensors exploit inductive coupling schemes, without on-chip detection circuits but with some potential for compatibility using near-field communication systems that are found increasingly in portable consumer electronic devices. The entire sensing system offers flexible and stretchable mechanics, with form factors that approach those of epidermal electronics.

2. Results and Discussion

FIG. 1a shows images and schematic illustrations of a typical device (22×28 $mm^2$ for the surface area of the substrate, and 10×15 $mm^2$ for the dimension of the sensor) that includes an inductive coil and a planar capacitor formed with interdigitated electrodes. The coil consists of four turns of thin copper traces in a filamentary serpentine design that affords both flexibility and stretchability. The width of the trace is 140 μm, and the lengths of the inner and outer turns are 4.8 and 9.5 mm, respectively. The electrodes consist of serpentine wires (50 μm in width) that have lengths between 6.5 to 8.4 mm, to form 9 digits with a digit-to-digit spacing of 600 μm. The dielectric properties of the microporous supporting substrate strongly influence the capacitance of the structure.

Figure 5:
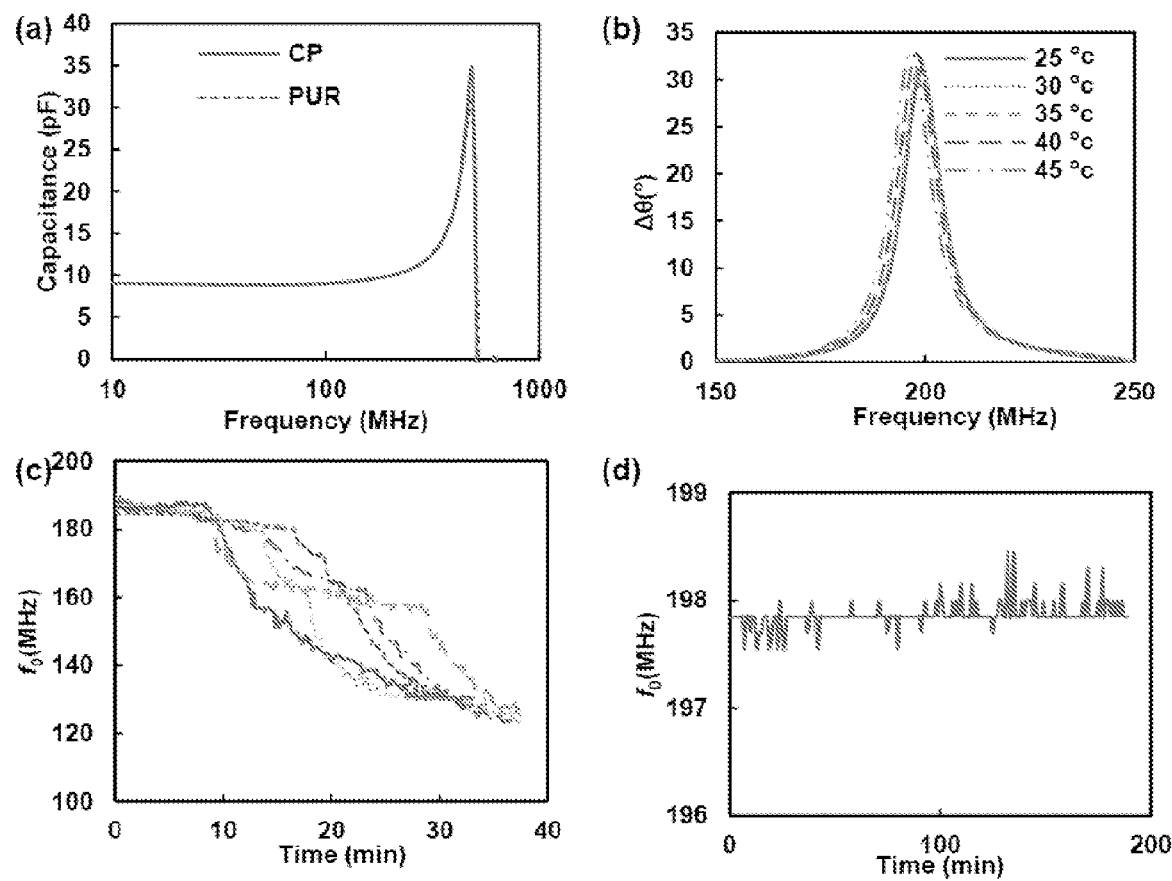
FIG. 5. (a) Capacitance values of a coaxial cable probe when in contact with sensors on CP and PUR substrates injected with 0.6 mL buffer solution. (b) Stability of a sweat sensor at temperatures from 25 to 45° C. (c) Time variation of $f_0$ for a sweat sensor on a silicone substrate in response to the injection of 0.6 mL buffer solution. (d) Drift and stability of a sensor output at dry state over an extended period of 3 hours.

In this way, the sweat sensor enables capacitive detection of the change of the dielectric properties of the substrate as its pores fill with biofluids (e.g. sweat). An external primary coil generates a time varying electromagnetic field that induces a current flow within the sensor. The impedance of the sensor is then determined by the amount of sweat within the substrate; this impedance influences that of the primary coil placed in proximity to the device. The resonance frequency ($f_0$) of the sensor can be determined from the frequency of a phase dip (or a peak in the phase difference, $\Delta\theta$, obtained from the subtraction of the phase of the primary coil with and without the sensor underneath) in the phase-frequency spectrum of the primary coil.[29-32] At measurement frequencies examined here (100 to 200 MHz), free water molecules are under the influence of δ relaxation.[33] The responses of the functional polymer substrates only involve contributions from induced charges. The movement of the water molecules and dynamics of the induced charges are sufficiently fast to respond to the external electromagnetic field. As a result, the combined dielectric properties of substrate and the sweat exhibit an invariant dielectric response over a wide range of frequencies (FIG. 5(a)). For present purposes, the frequency-dependence in the dielectric properties of the substrate can be ignored.

The sensor offers mechanical properties (elastic modulus≈80 kPa) similar to those of the skin.[34] The thickness of the substrate (1 mm), along with its lateral dimensions and porosity define the amount of fluid that it can capture. The devices exhibit robust, elastic behavior under axial stretching (FIGS. 1b and 1c) and other more complex modes of deformation (FIG. 1d). Attachment of the sensor onto the skin (FIG. 1e) using a thin layer of commercial spray-on bandage as adhesive leads to reversible skin/sensor bonding that can withstand significant extension and compression of the skin with sufficient mechanical strength to prevent delamination (FIGS. 1f and 1g).

Figure 2:
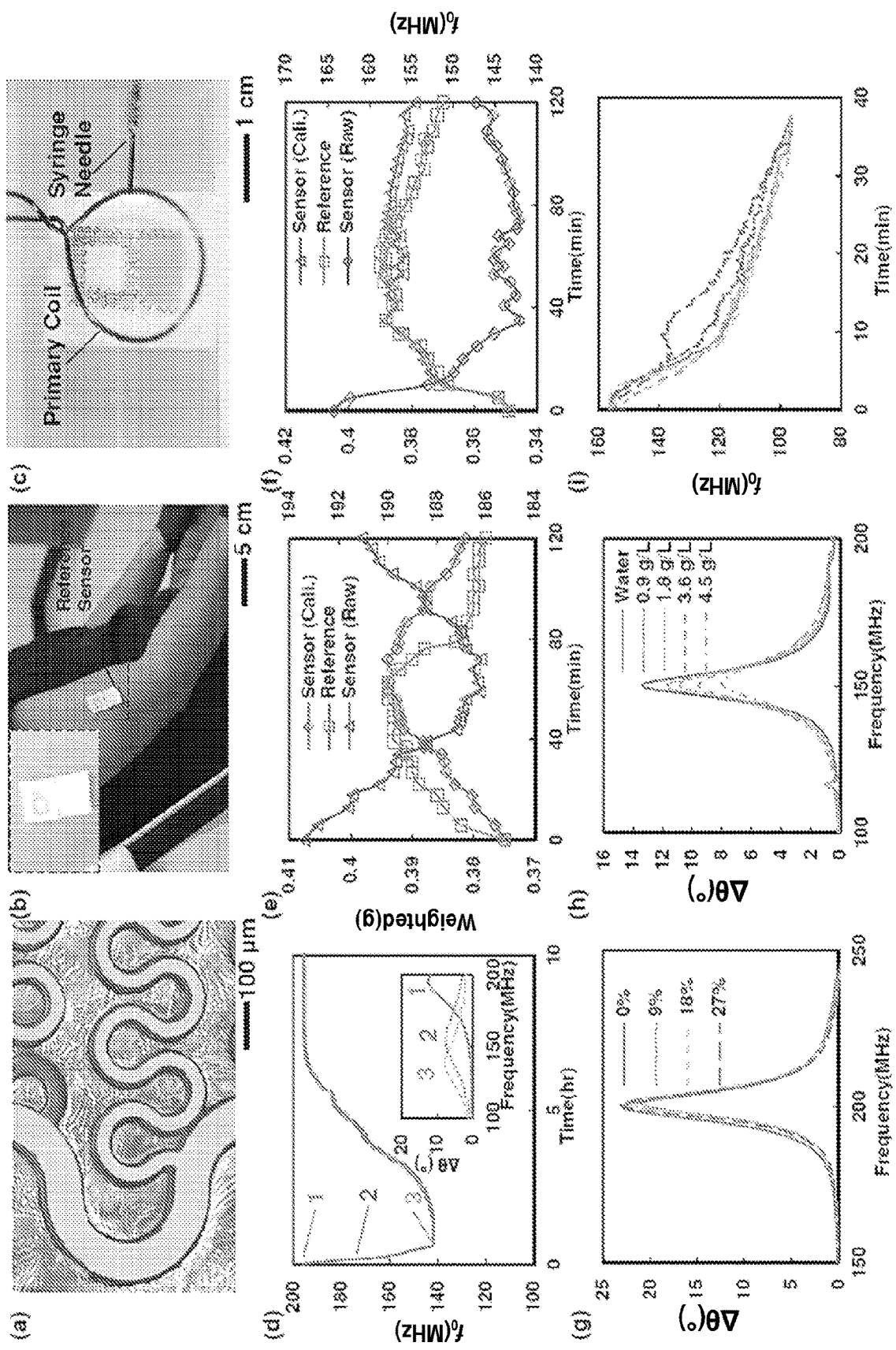
FIG. 2. (a) Scanning electron micrograph of a sensor on a PUR substrate coated with a thin silicone film; the regions colorized in yellow represent the interdigitated gold electrodes. (b) Picture of a sweat sensor and a reference sensor on the arm of a volunteer for in-vivo testing. (c) Picture of a sweat sensor underneath a primary coil. A syringe needle inserted into the sensor delivers controlled amounts of a buffer solution through a syringe pump. (d) Representative data showing the response of the sensor (resonant frequency, $f_0$) as a function of time after introduction of 0.6 mL buffer solution (labeled 1). The initial response (labeled 2) corresponds to wicking of the solution into the porous substrate, to yield a stable overall shift in $f_0$ (labeled 3). As the solution evaporates over the next several hours, $f_0$ recovers to approximately the initial value. The inset shows the phase difference measured by the primary coil at the three time points indicated in the main frame. (e, f) Results of testing on two volunteers, with comparisons to changes in weight evaluated using similar porous substrates (without detection coils) placed next to the sensors. Both $f_0$ and the weight of the sensors calibrated from $f_0$ are shown, along with comparison to the weight of the reference substrates. (g) Phase response of a sensor under biaxial strain from 0 to 27%. (h) Phase response as a function of concentration of sodium chloride, from 0 to 4.5 g/L. (i) Change in $f_0$ of a sweat sensor on a CP substrate as a function of time during controlled injection of 0.6 mL buffer solution.

In vitro experiments involve slow introduction of 0.6 mL of buffer solution (phosphate buffered saline, Sigma-Aldrich Corporation, St. Louis, Mo., USA) onto the substrates with a syringe pump, over the course of ≈40 minutes (FIG. 2d). The resonance frequency of the sensor ($f_0$), as measured by the shift of the phase peak of a primary coil placed in proximity to the device (FIG. 2c), decreases with increasing buffer solution content in the substrate. This response reflects increases in the permittivity due to replacement of air with buffer solution in the pores of the substrate, leading to an increase in the capacitance of the interdigitated electrodes associated with their proximity to the substrate. For a typical porous polyurethane (PUR) (PUR permittivity=7,[35] PUR substrate permittivity=1.42 at 0.93 porosity in air) (FIG. 2a), $f_0$ shifts from 195.3 to 143.3 MHz in this experiment (FIG. 2d). Drying of the sensor in air at room temperature leads to the recovery of $f_0$, eventually to the original value (195.3 MHz) over a period of ≈6 hours, indicating a reversible response with relative insensitivity to residual salt that might remain in the substrate.

Assessment of performance with human subjects involves use of sensors on cellulose paper (CP) and silicone substrates attached to the arms of two volunteers. Reference substrates made of the same materials with similar sizes placed in close proximity to the sensors provide means for determining the accuracy and establishing a calibrated response (FIG. 2b). The monitoring includes measuring the value of $f_0$ of the sensors and the weight of the reference substrates every 5 min for a period of 2 hours. The results indicate that $f_0$ is inversely proportional to the weight of the reference sensor, such that the response can be calibrated with any two measured weights. The calibrated results closely follow weight changes of 0.4 (FIG. 2e) and 0.2 g (FIG. 2f) in the reference substrates, corresponding to 0.4 and 0.2 mL of sweat over the sensing areas.

Figure 6:
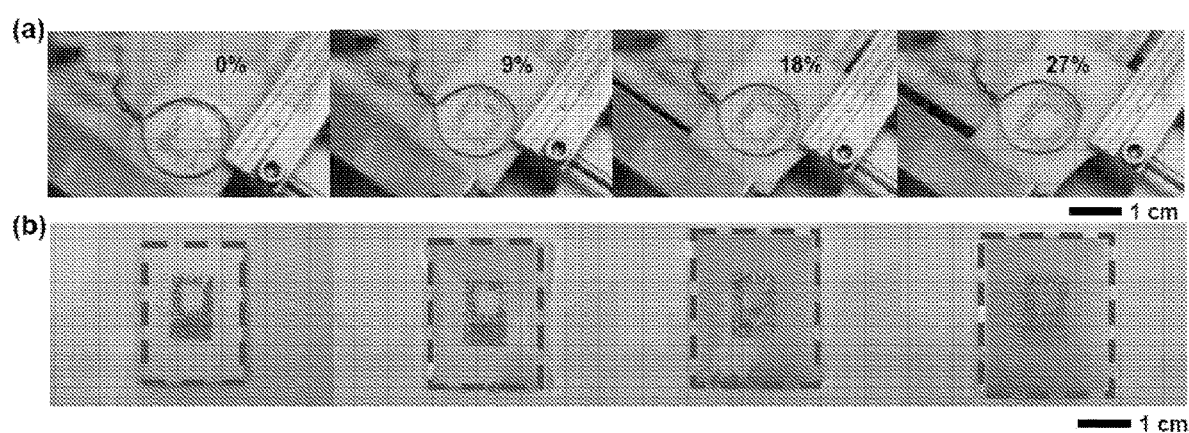
FIG. 6. (a) A sensor is biaxially stretched by two perpendicular stretchers at a strain from 0 to 27%. (b) Expansion of the surface area of the sensor in response to water absorption.

Dimensional changes associated with deformation of the skin or swelling of the device caused by sweat absorption could, conceivably, lead to changes in $f_0$. Strain induced effects can be examined by biaxially stretching a device and measuring $f_0$ at various states of deformation (FIG. 6(a)). The results show changes of only ≈0.9 MHz for biaxial strains of 27% (FIG. 2g) that are comparable to those caused by the absorption of water (FIG. 6(b)). The modest changes in $f_0$ under biaxial stretching may be attributed to the symmetric design of the sensor coil as well as mutual compensation of the changes in lengths and spacings of the interdigitated electrodes. The effects of temperature are also small. In particular, data indicate (FIG. 5(b)) that $f_0$ shifts from 199.25 MHz to 196.63 MHz when the temperature is changed from 25 to 45° C. Finally, although the salinity and ionic content of the sweat may lead to changes in both conductivity and permittivity, experiments with buffer solutions having various concentrations of sodium chloride (0 to 4.5 g/L) reveal only small variations in $f_0$ (≈0.6 MHz; FIG. 2h).

The sensors exhibit excellent repeatability and are suitable for repeated use. Multiple (i.e. five) measurements using sensors on CP and silicone substrates serve as demonstrations. Between each measurement, immersion in water followed by drying on a hot plate regenerates the devices. The changes in $f_0$ are repeatable for experiments that involve injection of 0.6 mL buffer solution (FIGS. 2i and 5(c)). The average change in $f_0$ is 58.3 MHz with a standard deviation of 1.1 MHz for the sensor on CP; the corresponding values for silicone are 60.1 MHz and 3.6 MHz, respectively. The changes in $f_0$ undergo different temporal patterns, as might be expected due to the differences in chemistry, microstructure and pore geometry for these two substrates. Measurements over 3 hours show no drifts in $f_0$ (FIG. 5(d)). The noise levels are <0.7 MHz; this parameter, together with an average change of $f_0$ of 58.3 to 60.1 MHz for 0.6 mL buffer solution over a surface area of 22×28 mm$^2$, suggests a measurement accuracy of ≈0.06 mL/mm$^2$.

Figure 3:
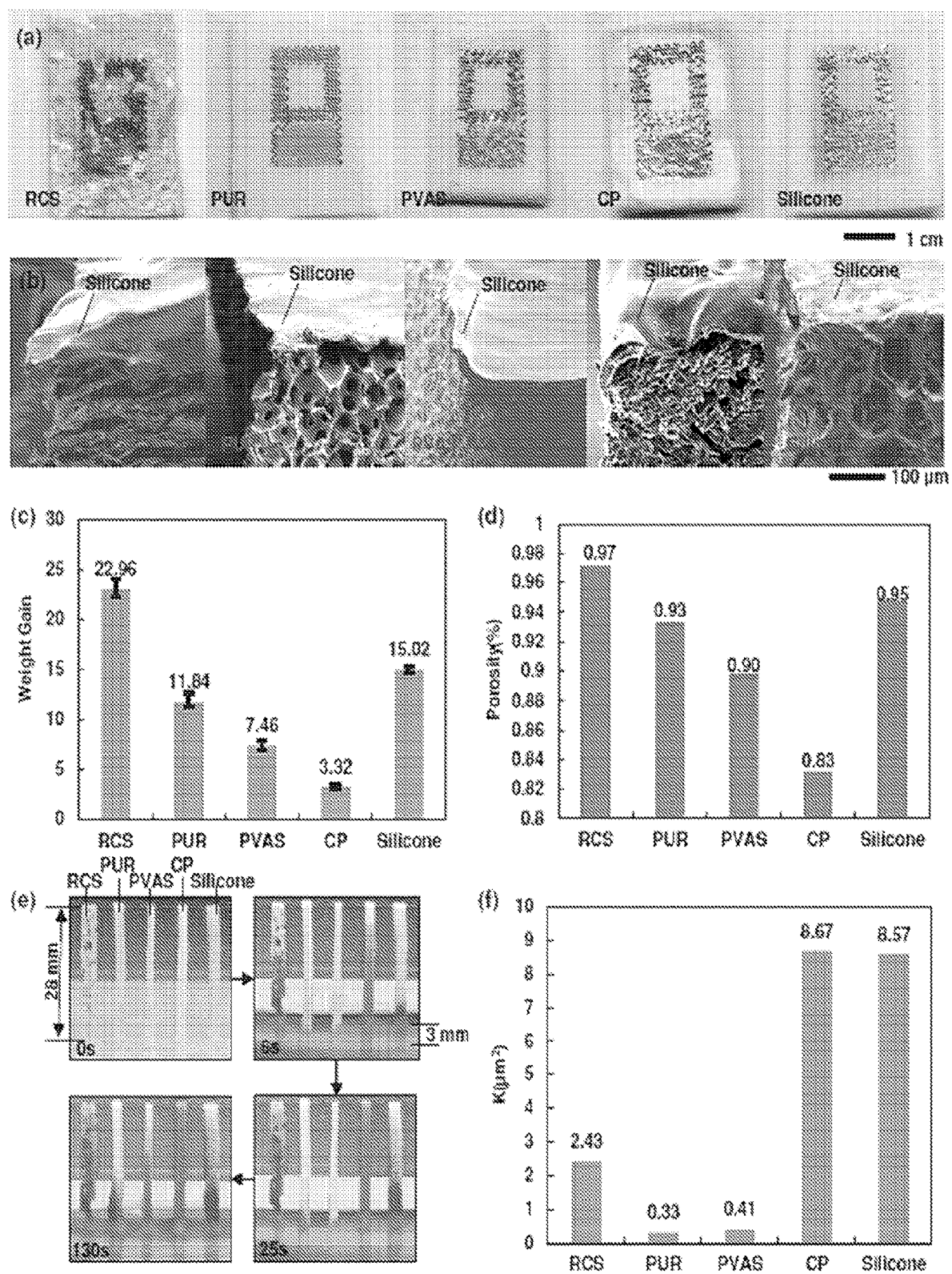
FIG. 3. (a) Wireless sweat sensors based on different porous substrates. (b) SEM images of the substrates coated with thin layer of silicone to facilitate chemical bonding between the sensors and the substrates. (c) Weight gain of different substrate materials associated with immersion in water. (d) Porosity of the substrate materials. (e) Images of strips of the substrate materials when partially immersed into water with red dye. (f) Water permeability of the substrate materials.

The coil structures can be mounted onto various types of functional substrates. Demonstrated examples include recycled cellulose sponge (RCS), polyurethane sponge (PUR), polyvinyl alcohol sponge (PVAS), cellulose paper (CP), and silicone sponge (FIG. 3a). Cutting with a hot-wire device (PUR, silicone) or with a razor blade (other) yields the appropriate lateral dimensions and thicknesses. Spin-coated silicone films with accurately controlled thickness (≈10 μm; FIG. 3b) enable strong bonding between each of these functional substrates and the sensors through surface chemical functionalization, while preventing direct contact between the sensors and the sweat. Relative characteristics in water absorption are also important to consider, as described in the following.

Figure 7:
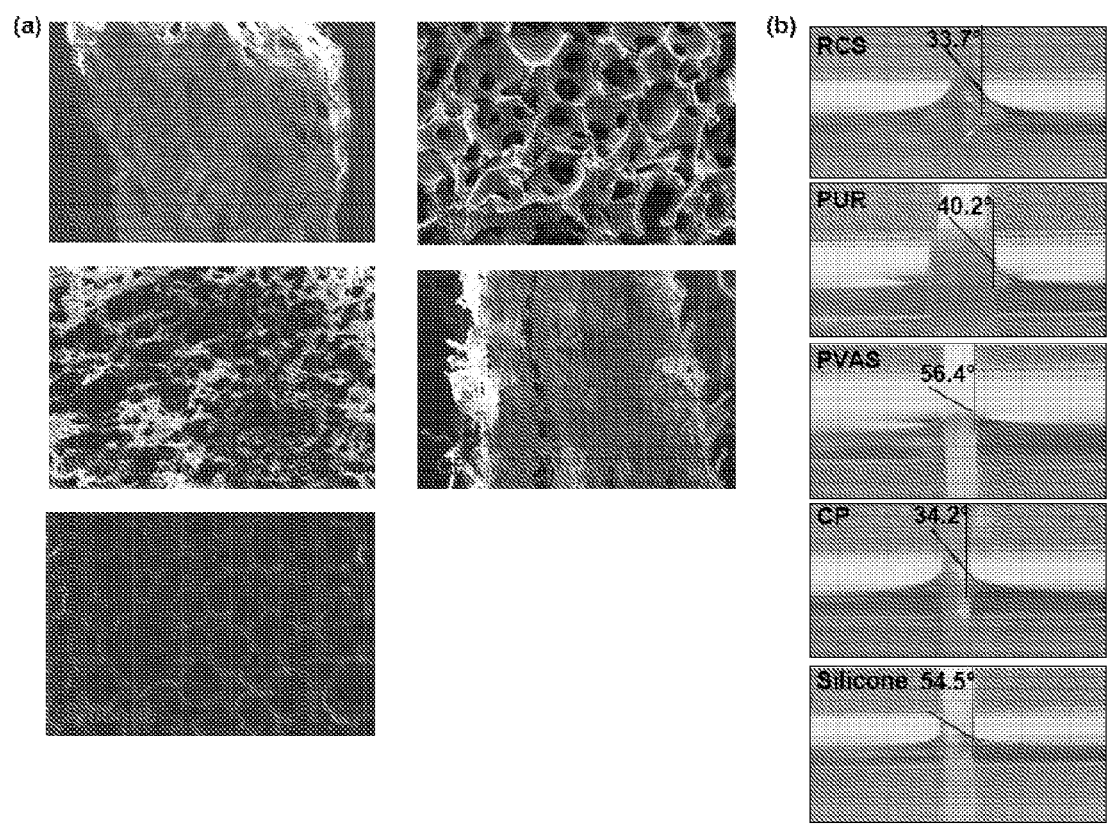
FIG. 7. (a) SEM images of porous materials, showing that the pores of PUR and Silicone dressing are uniform and that the pores of RCS, PVAS, and CP are amorphous. (b) Contact angle measurements performed by partially immersing strips of the porous materials into water dyed with red color, and recording the angle at the interface of two materials.

The percentage gain in weight of the various porous materials after immersion in water defines their ability to hold fluids; the results are ≈2300% (RCS), ≈1200% (PUR), ≈750% (PVAS), ≈350% (CP), and ≈1500% (silicone) (FIG. 3c). These data, together with measured volume changes yield the porosity levels: 0.97 (RCS), 0.93 (PUR), 0.90 (PVAS), 0.83 (CP) and 0.95 (silicone) (FIG. 3d). The water permeability can be determined from the capillary water absorption rate by combining Darcy's law[36] and the Hagen-Poiseuille equation.[37] Strips of the substrates (3 mm in width and 28 mm in length) are partially immersed into water with red dye (3 mm under the water). A camera enables measurements of changes in height of the absorbed water as a function of time (FIG. 3e). The CP material exhibits the fastest absorption rate (complete filling in ≈6 s), followed by the RCS (≈25 s). The PUR shows the smallest rate, with an increase in height of 8.3 mm over 130 s. These rates depend strongly on the pore size and degree of interconnectedness and on the contact angle. The latter can be determined optically (FIG. 7(b)); the former can be obtained by scanning electron microscopy (FIG. 7(a)) or by calculation and measurement of the height of absorbed water at a long period of time (details in supporting information). The permeability of the five substrates are 2.4 (RCS), 0.3 (PUR), 0.4 (PVAS), 8.7 (CP), and 8.6 (silicone) μm$^2$ (FIG. 3f).

Figure 4:
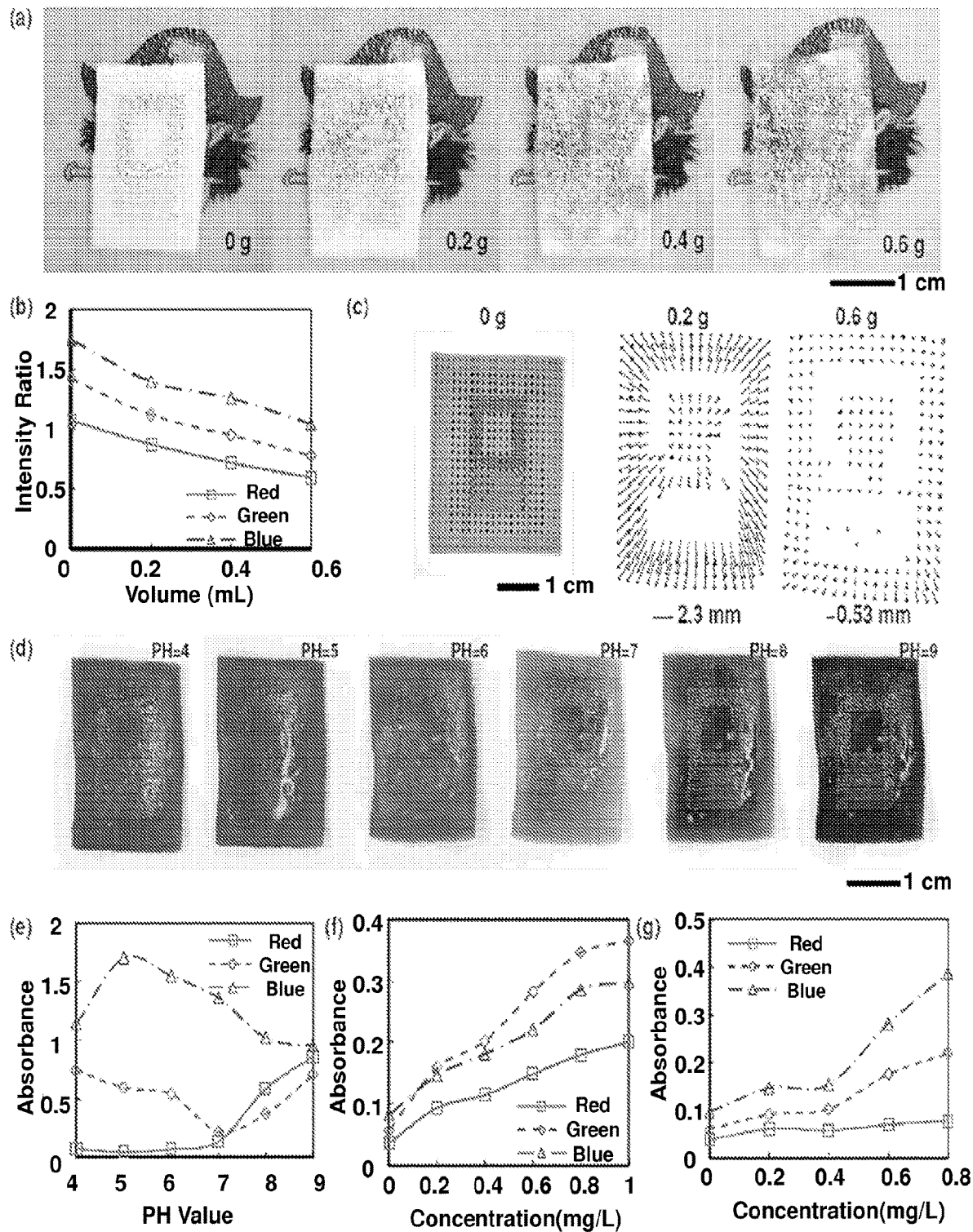
FIG. 4. (a) Images that illustrate a simple colorimetric detection scheme, based on systematic increases in transparency with water absorption. (b) The ratio of RGB intensity for a sensor like the one illustrated in (a), as a function of water absorption. (c) An image and vector diagrams corresponding to a sensor and its expansion due to water absorption. (d) Series of pictures of a sensor doped with a pH indicator, each collected with absorbed water at a different pH value. (e) Absorbance of RGB channels at different pH values. (f) Absorbance of RGB channels at different copper concentrations. (g) Absorbance of RGB channels at different iron concentrations.

In addition to dielectric response, absorption of water changes both the transparency, due to index matching effects, and the overall dimensions, due to swelling (FIGS. 4a and 4c). These effects can be used as additional measurement parameters to complement the electrical data described previously. The optical behavior can be illustrated by placing a sensor on a region of the skin with a temporary tattoo pattern. Continuous introduction of a buffer solution, up to a total of 0.6 mL, leads to increasing levels of transparency. Selected regions of the images in FIG. 4a can be used to obtain RGB (red, green, and blue) intensities at different locations. The resulting data (FIG. 4b) indicate that the water content is inversely proportional to the ratio of the RGB intensity on the sensor and the skin. The water also induces changes in the lateral dimensions. These changes can be measured by optically tracking the displacements of an array of opaque dots (Cr, by electron beam evaporation through a shadow mask) on the device (FIG. 4c). The results indicate a large displacement response to introduction of 0.2 mL of the buffer solution (≈2.3 mm dot displacement), but with diminishing response for an additional 0.4 mL (≈0.5 mm dot displacement). Nevertheless, these motions, which may be limited by mechanical constraints associated with mounting on the skin, might have some utility in measuring sweat loss.

Figure 8:
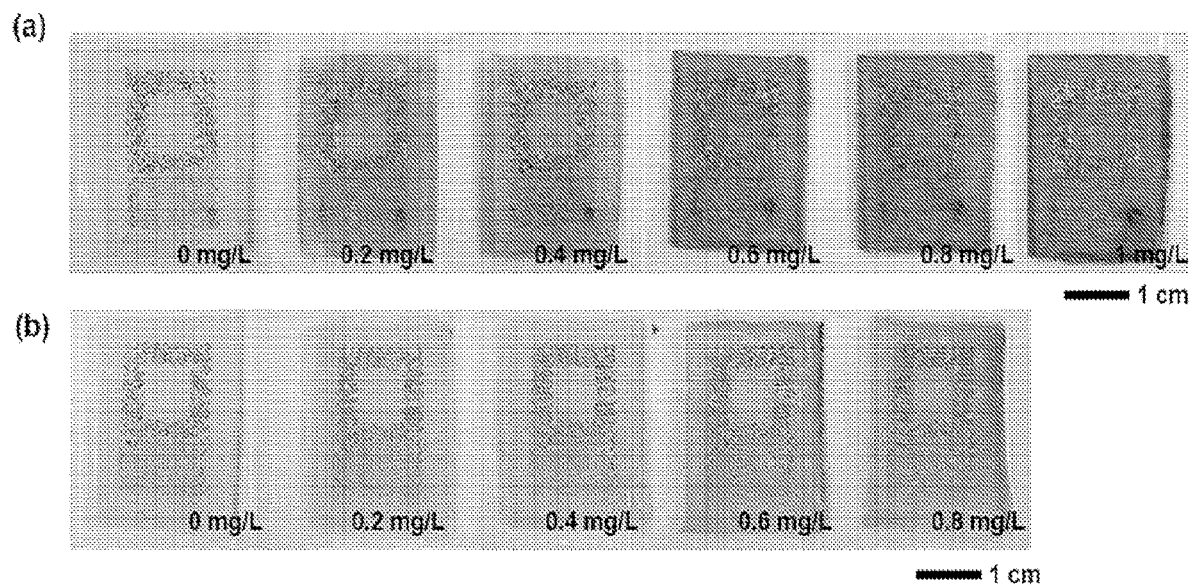
FIG. 8. (a) Color changes in the sensor when the free copper concentration changes from 0 to 1 mg/L, (b) Color changes in the sensor when the iron concentration changes from 0 to 0.8 mg/L.

The substrates can be rendered more highly functional, from an optical standpoint, by introduction of chemicals or immobilized biomolecules. Resulting interactions with the sweat can be evaluated through electrical dielectric measurement or simply colorimetric detection. For example, silicone substrates doped with colorimetric indicators render sensitivity to relevant biophysical/chemical parameters, such as pH values (FIG. 4d), free copper concentrations (FIG. 8(a)), and iron concentrations (FIG. 8(b)). To demonstrate pH detection, standard buffer solutions with pH values from 4 to 9 are introduced into a substrate that is dyed with a mixture of several different pH indicators (bromothymol blue, methyl red, methyl yellow, thymol blue, and phenolphthalein). These chemicals reversibly react with free —OH groups and/or protons in the buffer solutions, leading to changes in absorption spectra. Accordingly, the substrate undergoes a series of color changes that reveal the pH values (FIG. 4d). In addition, buffer solutions with copper (FIG. 8(a)) and iron (FIG. 8(b)) at physiological concentrations (0.8 to 1 mg/L) can also be detected using similar colorimetric schemes. The intensities of individual colors (red, green, and blue) extracted from the images determine changes in analyte concentrations (FIGS. 4e, 4f and 4g). This type of strategy has potential utility when used in combination with the sorts of wireless schemes introduced here. For example, near field communication[38] enabled devices such as cellphones also offer digital image capture capabilities, for simultaneous colorimetric measurement.

3. Conclusions

The results presented here provide materials and design strategies for integrating flexible and stretchable wireless sensors on functional substrates. Demonstrated devices intimately mounted on the skin enable non-invasive, wireless quantification of sweat loss as well as colorimetric detection of sweat composition. Similar strategies can be used to develop sensors for monitoring a range of key parameters associated not only with sweat but with other body fluids.

4. Experimental Section

Figure 9:
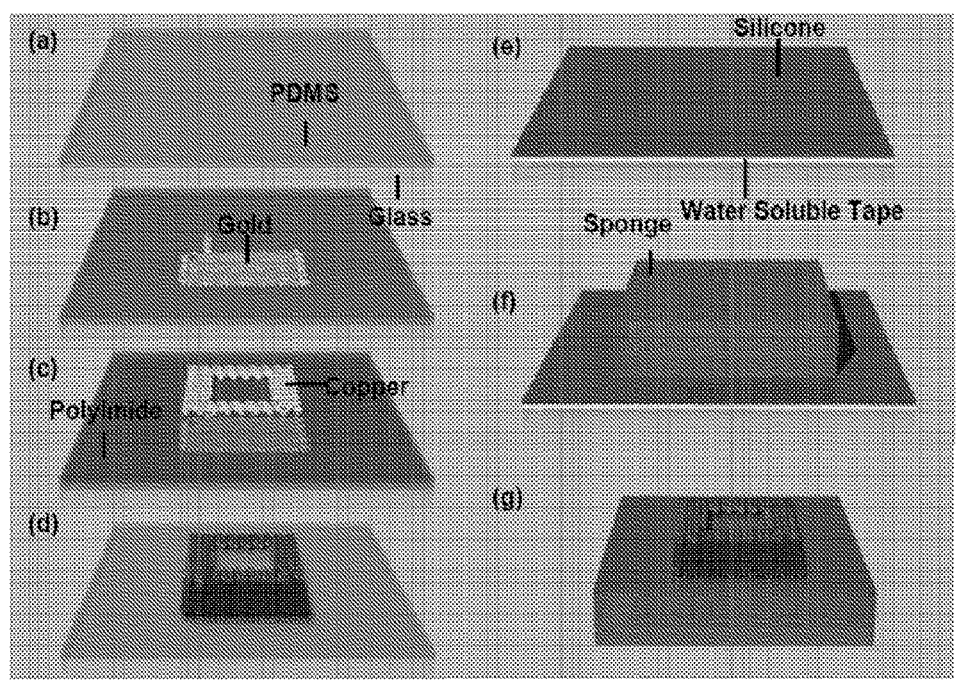
FIG. 9. (a)-(g) Fabrication processes for a wireless sweat sensor.

To fabricate the device, a layer of polydimethylsiloxane (PDMS, 20 µm thick) is first spin-coated onto a glass slide (FIG. 9(a)). Curing the PDMS at 120° C. for 10 min and treating its surface with reactive ion etching (RIE) for 5 min (20 sccm $O_2$, 300 mTorr pressure, 150 W power) allows conformal spin-coating of a layer of polyimide (PI; 1 µm thick) on top. A bilayer of chrome (5 nm) and gold (200 nm) deposited by electron beam (ebeam) evaporation is photolithographically patterned to form serpentine interdigitated electrodes (FIG. 9(b)). An additional spin-coated PI (1 µm) layer electrically insulates the surfaces of the electrode patterns, while selective regions on the PI layer are etched by RIE for electrical contact between the electrode and serpentine coils formed by patterning a layer of ebeam deposited copper (6 µm) (FIG. 9(c)). The entire patterns are encapsulated by another spin-coated PI layer (1 µm). Patterned RIE yields an open mesh layout, capable of release onto the surface of a target substrate by use of water-soluble tape (Aquasol ASWT-2, Aquasol Corporation, North Tonawanda, N.Y., USA). To prepare the functional substrates, a layer of uncured silicone (10 µm thick) is spin-coated onto a water soluble tape fixed on its edges to a glass slide by Scotch tape. Pre-curing the silicone at 150° C. for 1 min transforms the liquid precursor into a tacky, soft solid (FIG. 9(e)). Placing the substrates on the silicone film with gentle pressure allows the partially cured film to crosslink with porous structures on the surface. The silicone and the substrates are then fully cured at 120° C. to achieve robust bonding (FIG. 9(f)). The resulting structure is removed from the glass, and rinsed with water to remove the water soluble tape. Deposition of $Ti/SiO_2$ (5/60 nm) onto the exposed backside of the sensor facilitates chemical bonding to the PDMS film on the functional substrates after UV ozone activation. Dissolving the water soluble tape yields an integrated device with excellent levels of mechanical stretchability and flexibility (FIG. 9(g) and FIG. 1b). The functional substrates can be immersed into colorimetric indicators, followed by baking at 100° C. on a hotplate to dry the devices.

Five hydrophilic porous substrates serve as the sweat absorption materials, including Whatman GB003 cellulose paper (GE Healthcare Life Sciences, Pittsburgh, Pa., USA), Scotch-Brite recycled cellulose sponge (3M Cooperation, St. Paul, Minn., USA), polyvinyl alcohol sponge (Perfect & Glory Enterprise Co., Ltd., Taipei), Kendall hydrophilic polyurethane foam dressing (Covidien Inc., Mans-feld, MA, USA), and Mepilex silicone foam dressing (Mölnlycke Health Care AB, Sweden). For colorimetric detection, a universal pH indicator (pH 2-10) (Ricca Chemical, Arlington, Tex., USA) yields responses to buffer solutions with well-defined pH (Sigma-Aldrich Corporation, St. Louis, Mo., USA). Colorimetric copper and iron ion detection is enabled by a copper color disc test kit (CU-6, Hach Company, Loveland, Colo., USA) and an iron color disc test kit (IR-8, Hach Company, Loveland, Colo., USA), while standard stock solutions of copper and iron (Hach Company, Loveland, Colo., USA) are diluted to achieve different ion concentrations.

The sensors can be integrated onto the skin. Briefly, spray bandage (Nexcare No Sting Liquid Bandage Spray, 3M Cooperation, St. Paul, Minn., USA) is first applied onto the corresponding skin region. Evaporation of the solvent results in a tacky, water-permeable film that does not significantly influence the transdermal water loss from the skin and provides sufficient adhesion to fix the sweat sensors onto the skin. The sensor is then applied to the skin with continuous pressure over several seconds. The bonding is reversible, but is sufficiently strong to accommodate heavy sweating and shear forces.

The electrical responses of the sensors are evaluated using a HP 4291A impedance analyzer (Agilent Technologies, Santa Clara, Calif., USA) with a frequency range from 1 MHz to 1.8 GHz. The analyzer connects to a one-turn hand-wound copper primary coil whose resonance frequency is significantly different from the sweat sensor. The coil is placed 2 mm away from the sweat sensor during the measurement. However, small variations in the distance between the coil and the sweat sensor are tolerable, with negligible effects on the results. A xyz mechanical stage and a rotational platform allow manual adjustment of the position and orientation of the primary coil relative to the sweat sensor. The primary coil provides a time varying electromagnetic field that induces alternating voltages in the sweat sensor. Changes of sweat content within the substrate of the sensor lead to changes in the capacitance of the sweat sensor and its $f_0$. A syringe pump (KD Scientific Inc., Holliston, Mass., USA) is used to deliver buffer solutions to the sensors during the in vitro experiments. The sweat sensors with a CP substrate and a silicone porous material are mounted on the arms of two volunteers for 2 hour in vivo testing, with reference substrates of the same materials and sizes placed in close proximity to the sweat sensors (FIG. 2b). For the first hour, the volunteers exercise continuously to generate sweat, and then stop to rest for the second hour. During the measurement, the sweat sensors remain on the skin, while the reference sensors are peeled off every 5 min to record their weight using a precise balance and reattached back to the same positions afterwards.

The absorbance values are estimated from the digital images by accessing the RGB (red, green, blue) values of the selected regions on the experimental images using ImageJ[39]. The average RGB values are determined from multiple pixels enclosed within a rectangular frame drawn by ImageJ with a plugin called, "measure RGB". The Absorbance (A) defined as the negative log of the transmittance ($I_n/I_{blank}$), is then calculated using the following formula:

$$A = -\log(I_n/I_{blank}) \quad (1)$$

in which $I_n$ denotes the R, G or B values for the functional substrates and $I_{blank}$ the R, G, or B value for the background, both obtained from the experimental images.

REFERENCES

[1] M. Chan, EstC, J.-Y. Fourniols, C. Escriba, E. Campo, Artif. Intell. Med. 2012, 56, 137.
[2] A. Lay-Ekuakille, S. Mukhopadhyay, A. Lymberis, in Wearable and Autonomous Biomedical Devices and Systems for Smart Environment, Vol. 75, Springer, Berlin Heidelberg, 237.
[3] A. J. Bandodkar, A. M. O'Mahony, J. Ramirez, I. A. Samek, S. M. Anderson, J. R. Windmiller, J. Wang, Anal. 2013, 138, 5288.
[4] P. Bonato, IEEE Eng. Med. Biol. Mag. 2010, 29, 25.
[5] P. M. Deshmukh, C. M. Russell, L. E. Lucarino, S. N. Robinovitch, Enhancing clinical measures of postural stability with wear-able sensors, presented at Engineering in Medicine and Biology Society (EMBC), 2012 Annual International Conference of the IEEE, Aug. 28 2012-Sep. 1 2012.
[6] J. Varkey, D. Pompili, T. Walls, Pers. Ubiquit. Comput. 2011, 16,897.
[7] J. R. Windmiller, J. Wang, Electroanal. 2013, 25, 29.
[8] D.-H. Kim, N. Lu, R. Ma, Y.-S. Kim, R.-H. Kim, S. Wang, J. Wu, S. M. Won, H. Tao, A. Islam, K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, Science 2011,333, 838.
[9] R. C. Webb, A. P. Bonifas, A. Behnaz, Y. Zhang, K. J. Yu, H. Cheng, M. Shi, Z. Bian, Z. Liu, Y. S. Kim, W. H. Yeo, J. S. Park, J. Song, Y. Li, Y. Huang, A. M. Gorbach, J. A. Rogers, Nat. Mater. 2013, 12, 938.
[10] X. Huang, H. Cheng, K. Chen, Y. Zhang, Y. Liu, C. Zhu, S. C. Ouyang, G. W. Kong, C. Yu, Y. Huang, J. A. Rogers, IEEE Trans. Biomed. Eng. 2013, 60, 2848.
[11] N. Lu, C. Lu, S. Yang, J. Rogers, Adv. Funct. Mater. 2012, 22, 4044.
[12] W.-H. Yeo, Y.-S. Kim, J. Lee, A. Ameen, L. Shi, M. Li, S. Wang, R. Ma, S. H. Jin, Z. Kang, Y. Huang, J. A. Rogers, Adv. Mater. 2013, 25, 2773.
[13] K. Virkler, I. K. Lednev, Forensci. Sci. Int. 2009, 188, 1.
[14] T. L. Guidotti, J. McNamara, M. S. Moses, Indian J. Med. Res. 2008, 128, 524.
[15] V. Sikirzhytski, K. Virkler, I. K. Lednev, Sensors 2010, 10, 2869.
[16] S. Hu, J. A. Loo, D. T. Wong, Proteomics 2006, 6, 6326.
[17] P. Salvo, F. Di Francesco, D. Costanzo, C. Ferrari, M. G. Trivella, D. De-Rossi, IEEE Sens. J. 2010, 10, 1557.
[18] Y. Haixia, L. Dachao, R. C. Roberts, X. Kexin, N. C. Tien, J. Micro-electromech. Syst. 2012, 21, 917.
[19] A. Lay-Ekuakille, S. Mukhopadhyay, S. Coyle, F. Benito-Lopez, R. Byrne, D. Diamond, in Wearable and Autonomous Biomedical Supporting Information 1. Methods for Determination of Weight Gain, Porosity, and Permeability The percentage weight gain (W %) of the substrates can be obtained by measuring the weight of the materials in dry ($W_{dry}$) and water-saturated ($W_{sat}$) states. Thus, W % can be expressed as.

$$W\% = \frac{W_{sat} - W_{dry}}{W_{dry}} \times 100\% \quad (1)$$

The porosity ($\phi$) of the materials is determined by the volume of pores ($V_{pores}$) to the total volume of the medium ($V_{bulk}$), is thus defined by $$\phi = \frac{V_{pores}}{V_{bulk}} = \frac{(W_{sat} - W_{dry})/\rho_{water}}{(W_{sat} - W_{dry})/\rho_{water} + W_{dry}/\rho_{bulk}} \quad (2)$$

where, $\rho_{water}$ and $\rho_{bulk}$ are the density of the water and the substrate materials, respectively.

To obtain the water permeability of the substrates, the Darcy law[1], which describes the water flow in porous materials, can be used. It is found that the pressure gradient ($\nabla P$) that causes the water to flow in the porous materials can be described by $$\nabla P = \frac{\mu}{K} q \quad (3)$$

where q is the volume average velocity (or flux), which represents discharge per unit area, with units of length per time. The factor K is the permeability of the material and $\mu$ the viscosity of the water. Determination of $\nabla P$ typically involves an experimental setup containing two chambers with well-controlled pressures. An alternative method uses the Hagen-Poiseuille equation[2] to determine $\nabla P$ by considering the porous materials as bundles of capillaries. As a result, the pressure gradient can be further expressed as:

$$\nabla P = \frac{\nabla P}{L} = \frac{8\mu Q}{\pi R^4} \quad (4)$$

where $\Delta P$ is the pressure loss, L the length of the pipe, $\mu$ the dynamic viscosity, Q the volumetric flow rate (volume of fluid passing through the surface of the pipe per unit time), R the radius of the capillaries. Combing Eq. (3) and Eq. (4) yields $$\frac{\mu}{K} q = \frac{8\mu Q}{\pi R^4} \quad (5)$$

Here, $Q/\pi R^2$ represents the interstitial velocity of the flow, while q represents the superficial velocity of the flow. As a result, the ratio between $Q/\pi R^2$ and q is equivalent to the porosity of the materials $$\phi = \left(\frac{Q/\pi R^2}{q}\right).$$

Thus, Eq. (5) can be further simplified as $$R^2 = \frac{8K}{\phi} \quad (6)$$

The linear momentum balance of the flow within a capillary tube can be expressed as $$\frac{2\sigma\cos(\theta)}{R} = \rho g h + \frac{8\mu h h'}{R^2} + \frac{d(hh')}{dt} \quad (7)$$

where terms from left to right refer to the capillary pressure, the hydrostatic pressure, the viscous pressure loss, and the inertia terms, respectively. In Eq. (7), σ is the surface tension of water, h is the height of water in the capillary tube at time t, and θ is the contact angle at the interface of the capillary tube and the water. As the porous materials may not have uniform R (especially for the porous materials with amorphous pores), such as RCS, PVAS, and CP in FIG. 7(a), it is possible to replace R in Eq. (7) with a more general term $R_s$, which represents the static radius of the porous materials and can be obtained from the equilibrium height ($h_{eq}$) in the static case (height of the absorbed water in the porous materials when t reaches ∞). The static radius $R_s$ can be calculated from $$h_{eq} = \frac{2\sigma\cos(\theta)}{R_s \rho g} \quad (8)$$

As a result, Eq. (7) can be further expressed as $$\frac{2\sigma\cos(\theta)}{R_s} = \rho g h + \frac{8\mu h h'}{R_s^2} + \rho\frac{d(hh')}{dt} \quad (9)$$

by considering a flow regime where the influence of inertia as well as the influence of gravity can be neglected[3,4]. Thus, Eq. (8) can be simplified to $$\frac{2\sigma\cos(\theta)}{R_s} = \frac{8\mu h h'}{R_s^2} \quad \text{or} \quad (10)$$

$$\frac{h dh}{dt} = \frac{\sigma\cos(\theta)}{4\mu} \quad (11)$$

Solving this ordinary differential equation with the initial condition h(0)=0 leads to the Lucas-Washburn equation [4].

$$h^2 = \frac{\sigma R_s \cos(\theta)}{2\mu}t \quad (12)$$

According to Eq. (6), Eq. (12) can be further expressed as $$h^2 = \frac{\sigma R_s \cos(\theta)}{2\mu}t \cong \frac{4\sigma\cos(\theta)}{\mu}\frac{K}{\phi R_s}t \quad (13)$$

As a result, the permittivity (K) can then be determined using the following equation $$K = \frac{h^2 \mu \phi R_s}{4\sigma\cos(\theta)t} \quad (14)$$

where h, t, φ, and $R_s$ of individual materials can all be experimentally determined, as summarized in Table 3.

TABLE 3

Parameters of the porous materials used for functional substrates

| Materials | W % | $\rho_{bulk}$ (g/cm³) | φ | h (m) | t (s) | $R_s$ (m) | K (µm²) |
|---|---|---|---|---|---|---|---|
| RCS | 2296 | 1.5 | 0.97 | 0.025 | 25 | 2.52E−5 | 2.43 |
| PUR | 1184 | 1.2 | 0.94 | 0.008 | 130 | 1.52E−4 | 0.33 |
| PVAS | 746 | 1.2 | 0.90 | 0.013 | 130 | 6.34E−5 | 0.41 |
| CP | 332 | 1.5 | 0.83 | 0.025 | 6 | 2.50E−5 | 8.67 |
| Silicone | 1502 | 1.2 | 0.95 | 0.025 | 70 | 1.78E−4 | 8.57 |

2. Experiments for Determination of Weight Gain, Porosity, and Permeability $R_s$ can be determined from the $h_{eq}$ measurement, in which 50 cm strips of the porous materials are partially immersed into the water (approximately 1 cm strip in the water), while the heights of the water in the strips after one day immersion are measured. As PUR and silicone have more uniform pore sizes (FIG. 7(a)), their $R_s$ can also be determined by measuring the radii of 10 pores in their SEM images and taking the average numbers. The contact angle θ can be measured through the analysis of images taken by a camera on the interface of water and the porous materials (FIG. 7(b)). The relation between h and t can be obtained using video captured throughout the process of water absorption.

REFERENCES

[1] N. Fries, Capillary Transport Processes in Porous Materials: Experiment and Model, Cuvillier.

[2] S. P. Sutera, R. Skalak, Annu. Rev. Fluid Mech. 1993, 25, 1.

[3] E. W. Washburn, Phys. Rev. 1921, 17, 273.

[4] A. Hamraoui, T. Nylander, J. Colloid Interf. Sci. 2002, 250, 415.

Example 2: Epidermal Microfluidic Sweat Patch

This Example discloses an epidermal microfluidic sweat patch incorporating at least one microfluidic channel and a plurality of colorimetric indicators disposed within cavities of the patch. The patch optionally includes a near-field communication coil.

Table 4 shows concentrations of parameters and chemical species relevant to sweat monitoring.

TABLE 4

Parameters and chemical species relevant to sweat monitoring.

| Constituents | Median Concentration | Range |
| --- | --- | --- |
| Sweat gland density | 100 pores/cm$^2$ | 50~300 pores/cm$^2$ |
| Sweat rate | 50 μL/hour · cm$^2$ | 12-120 μL/hour · cm$^2$ |
| pH | | 4.0-6.8 |
| Glucose | 0.17 mM | 5.6 μM-2.2 mM |
| Lactic acid | 14 mM | 3.7-50 mM |
| Chloride | 23 mM | 0.02-280 mM |
| Sodium ion | 31 mM | 0.11-390 mM |

Figure 10:
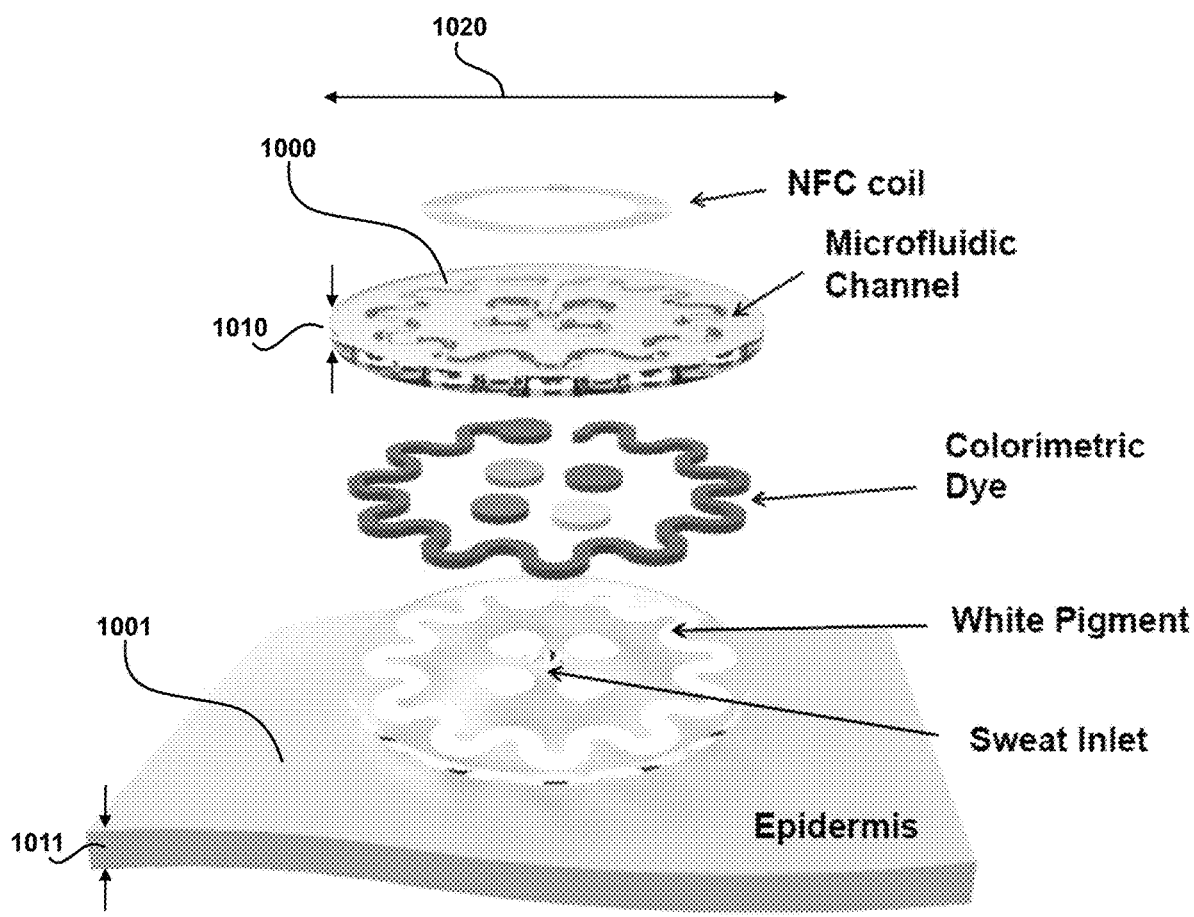
FIG. 10. Exploded view of a colorimetric sensor comprising a near-field communication coil.
Figure 11:
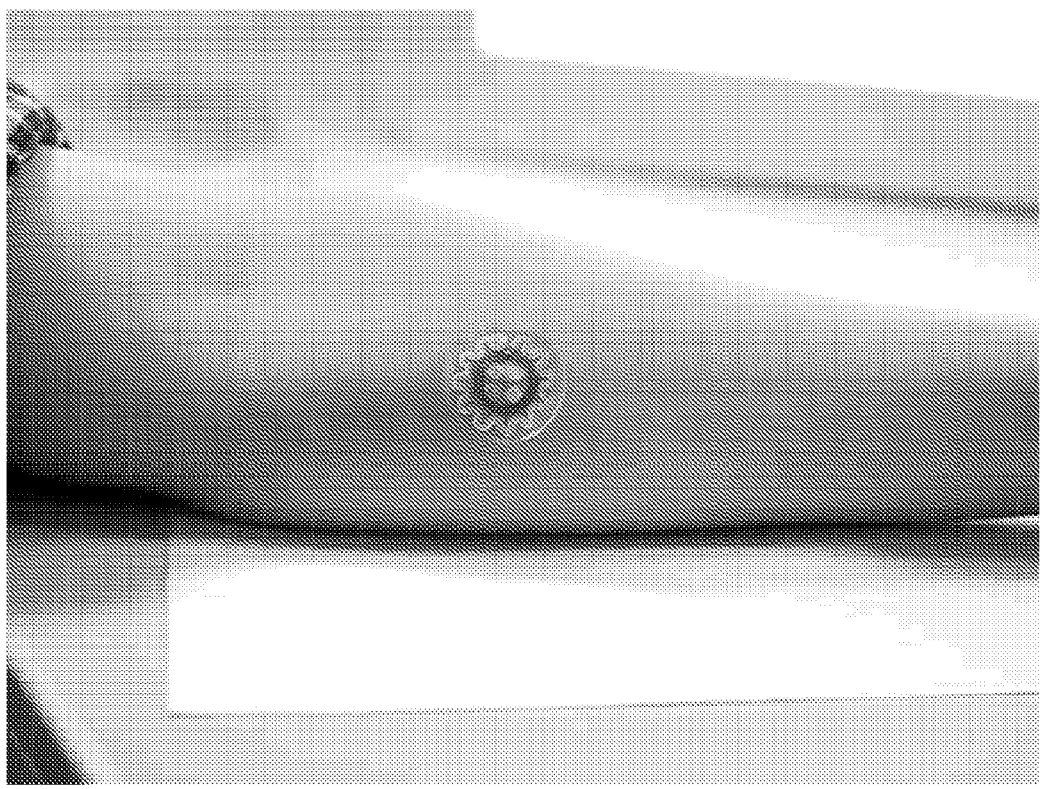
FIG. 11. Photograph of the device of FIG. 10 adhered to the skin of a subject.

FIG. 10 shows an exploded view of a colorimetric sensor comprising a near-field communication coil. The functional substrate 1000 has various properties, such as a modulus (e.g., less than or equal to 100 MPa), a porosity (e.g., greater than or equal to 0.5), a thickness 1010 (such as selected from a range of 500 pm to 2 mm), lateral dimensions or diameter 1020 (such as less than equal to 700 mm). FIG. 11 is a photograph of the device of FIG. 10 adhered to the skin of a subject.

Figure 12:
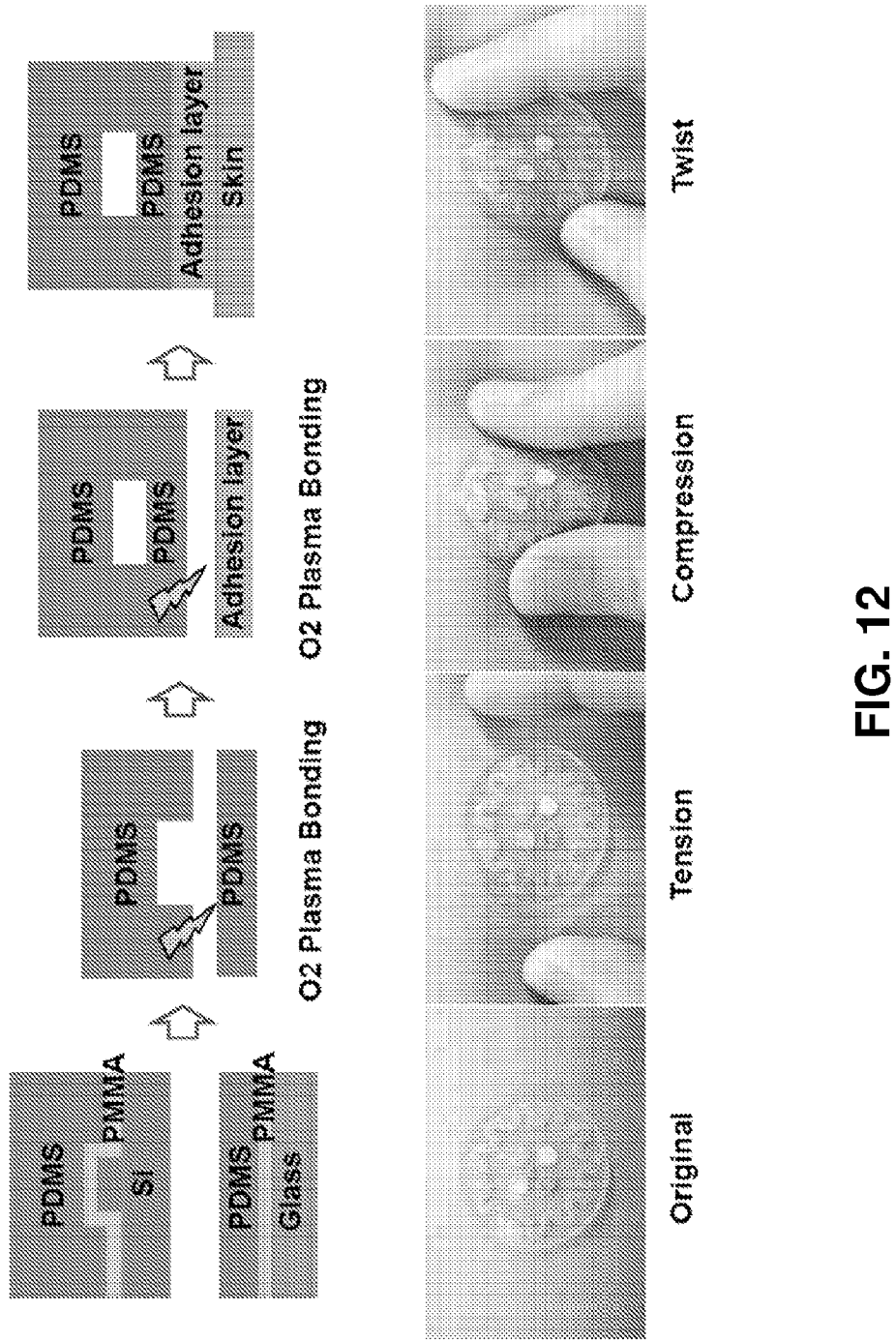
FIG. 12. Fabrication method and adhesion test on skin.

FIG. 12 illustrates a fabrication method for a sweat patch and an adhesion test on skin.

Figure 13:
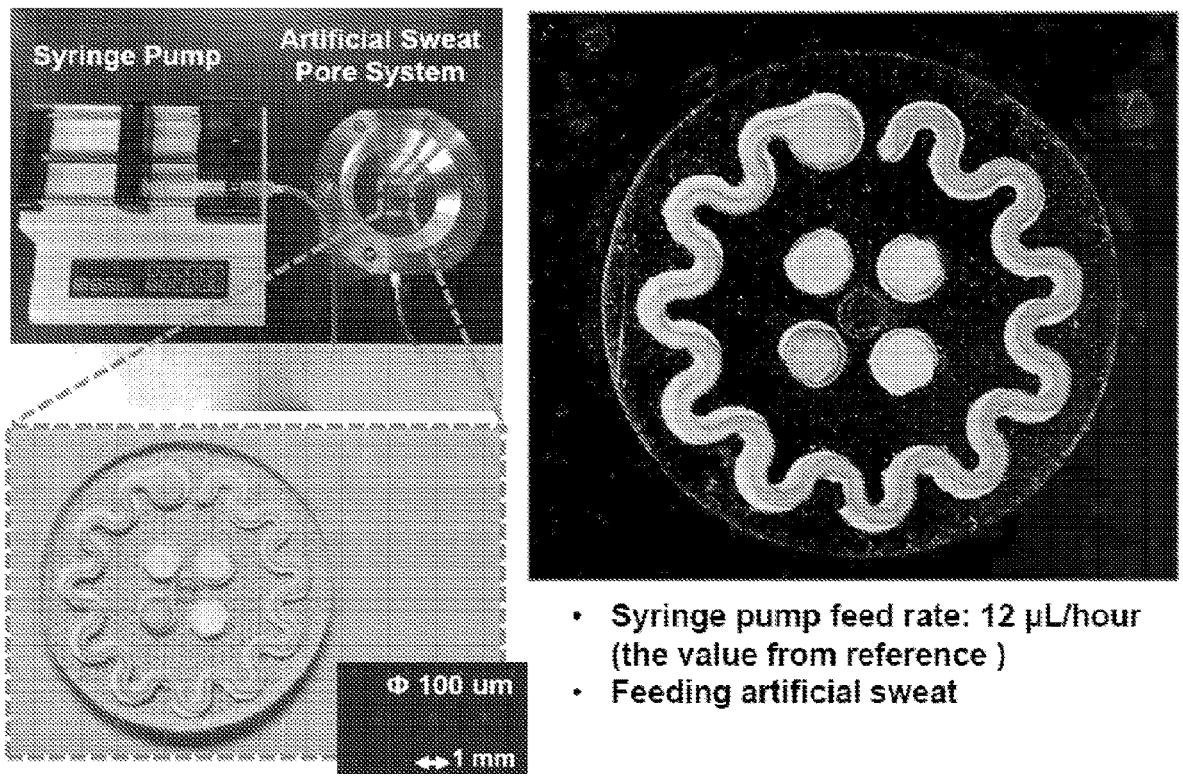
FIG. 13. Artificial sweat pore test using a syringe to feed artificial sweat at a rate of 12 µL/hr.

FIG. 13 illustrates an artificial sweat pore test using a syringe to feed artificial sweat at a rate of 12 μL/hr.

Figure 14:
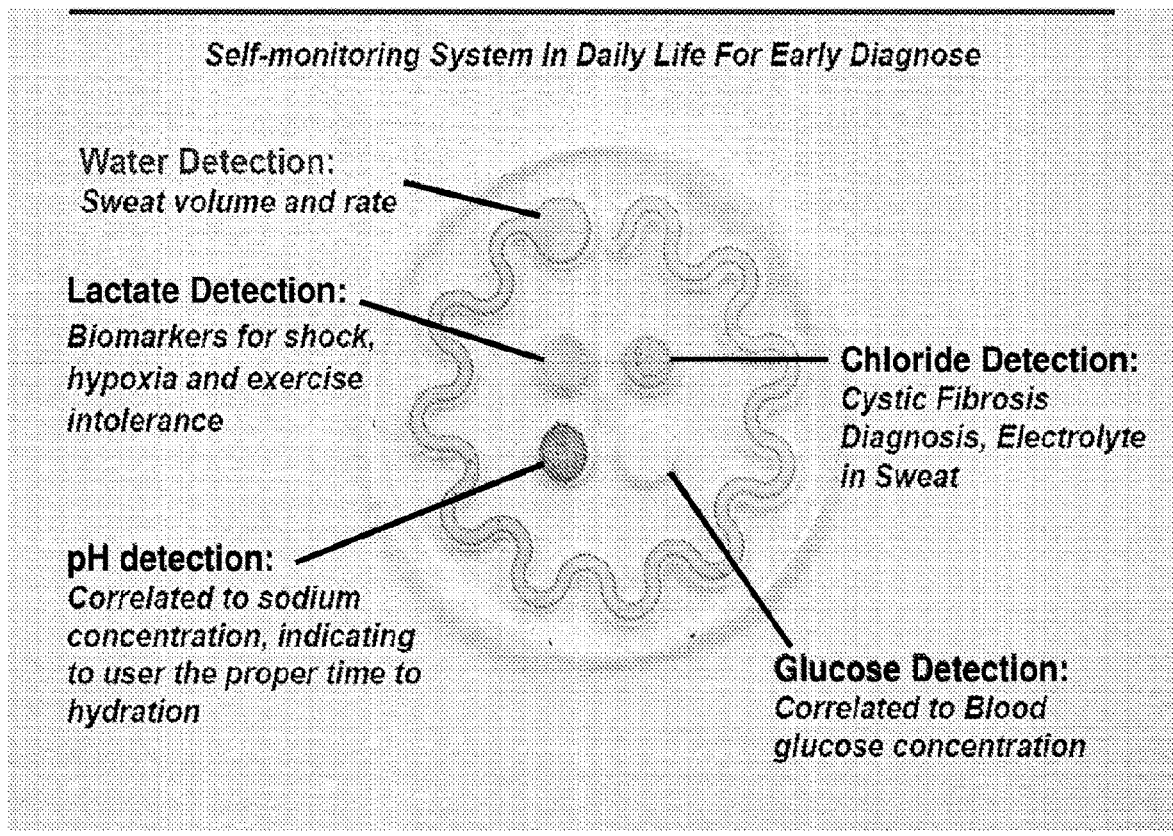
FIG. 14. Colorimetric detection of various biomarkers using a sweat sensor for self-monitoring and early diagnosis.
Figure 15:
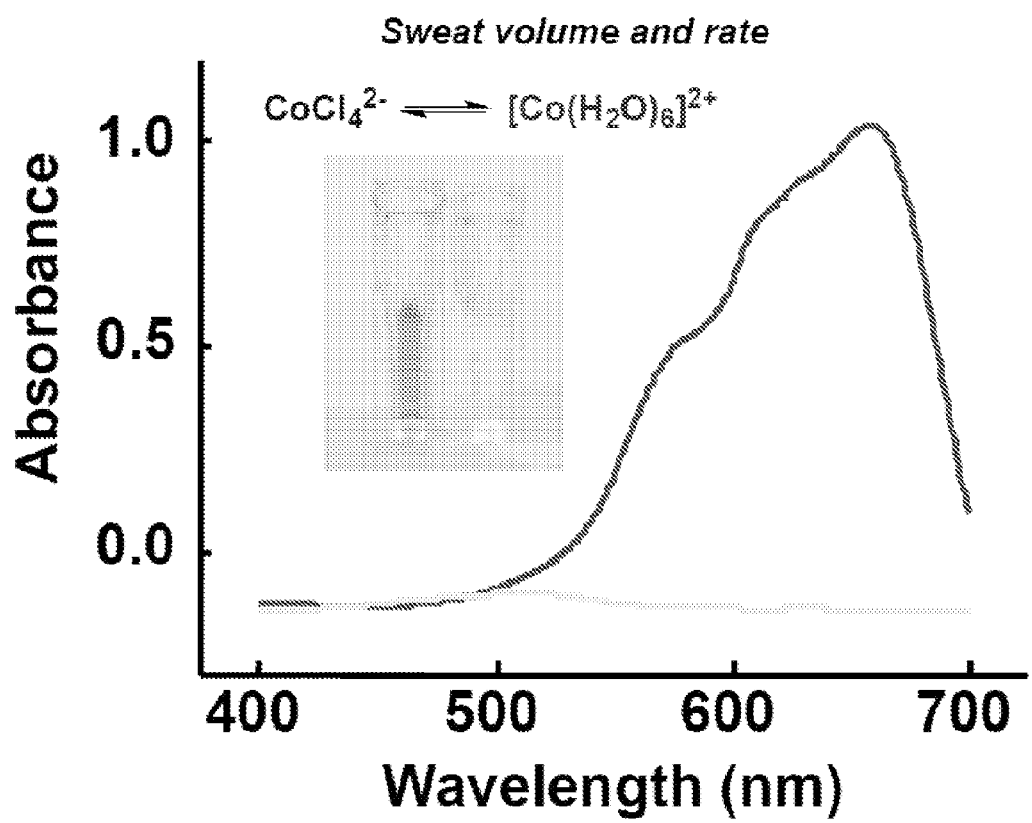
FIG. 15. Absorbance spectrum illustrating the color change of a reactant that may be used to determine sweat volume and rate.
Figure 16:
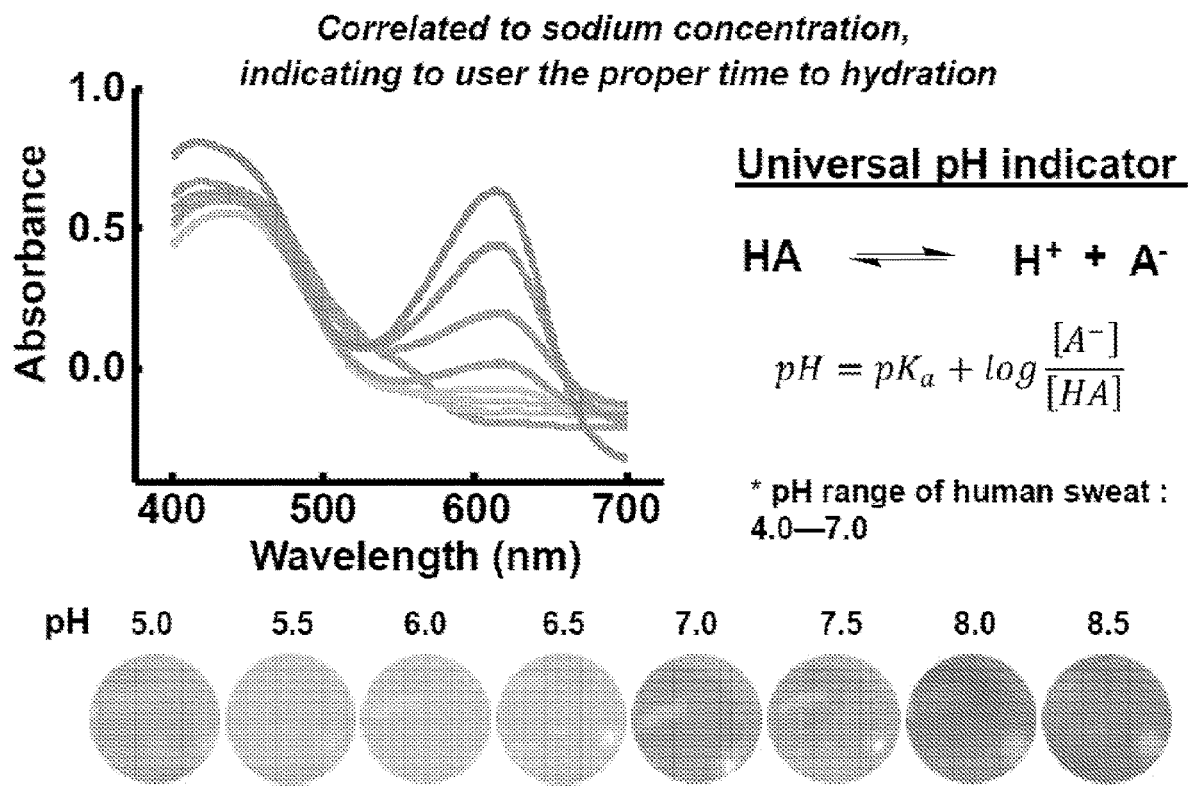
FIG. 16. Absorbance spectrum and legend illustrating the color change of a reactant(s) that may be used to determine sweat pH, which may be correlated with sodium concentration, indicating to a user the proper time to hydrate.
Figure 17:
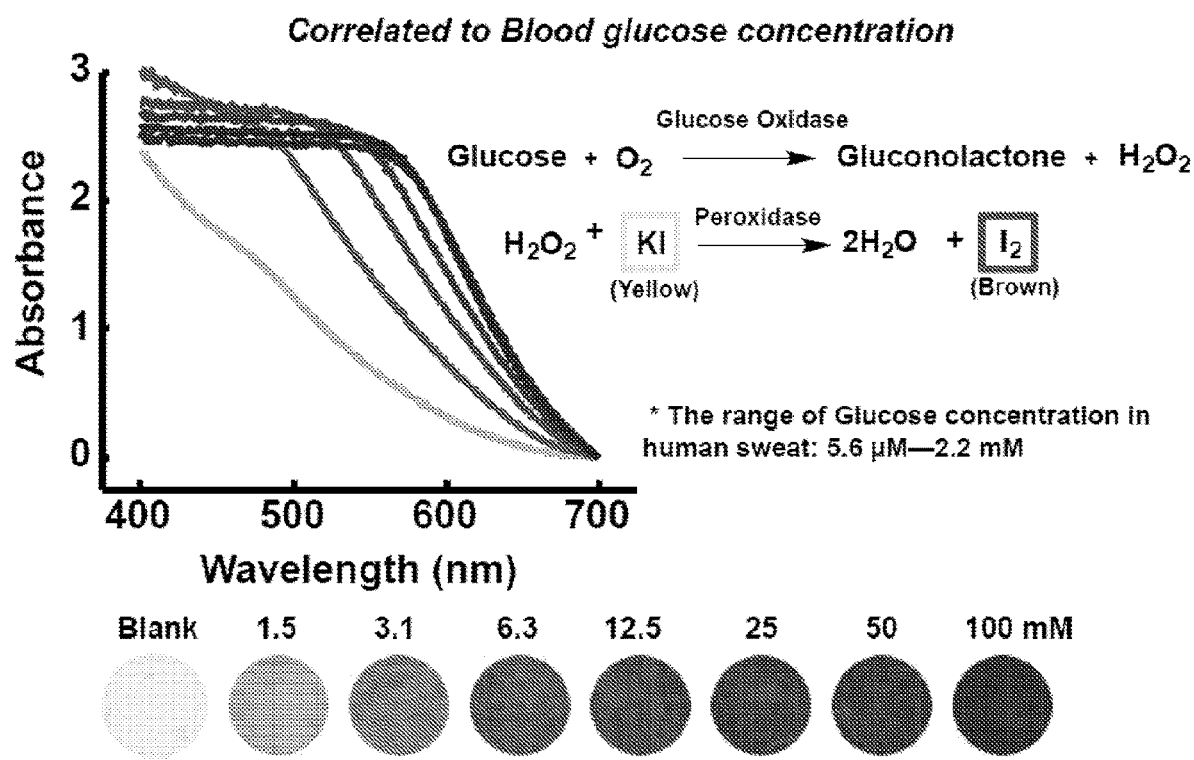
FIG. 17. Absorbance spectrum and legend illustrating the color change of a reactant(s) that may be used to determine glucose concentration in sweat, which may be correlated with blood glucose concentration.
Figure 18:
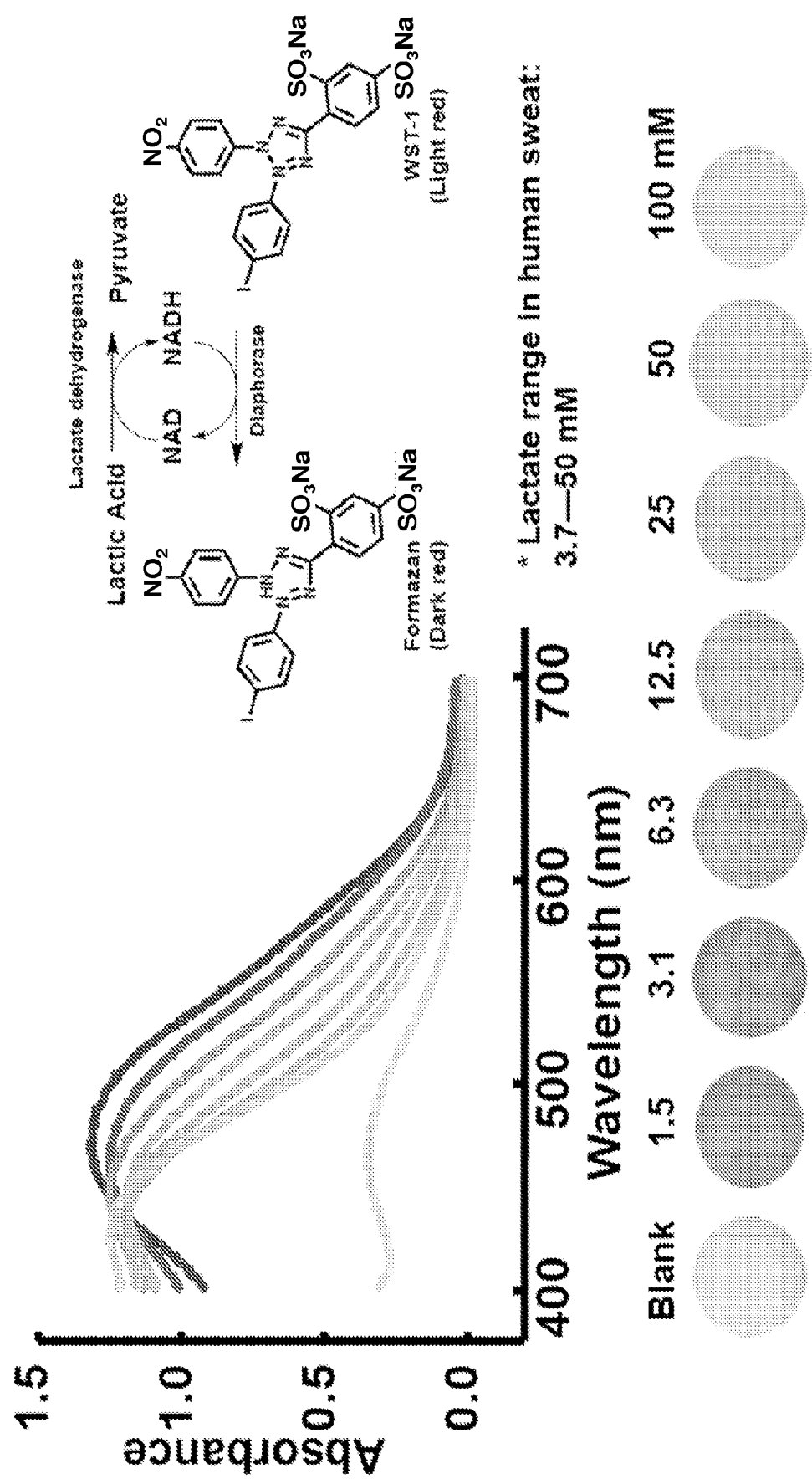
FIG. 18. Absorbance spectrum and legend illustrating the color change of a reactant(s) that may be used to determine lactate concentration in sweat, which may provide an indication of shock, hypoxia and/or exercise intolerance.

FIG. 14 shows a sweat patch incorporating colorimetric detection of various biomarkers for self-monitoring and early diagnosis. For example, FIG. 15 shows an absorbance spectrum illustrating the color change of a reactant that may be used to determine sweat volume and rate. FIG. 16 shows an absorbance spectrum and legend illustrating the color change of a reactant(s) that may be used to determine sweat pH, which may be correlated with sodium concentration, indicating to a user the proper time to hydrate. FIG. 17 shows an absorbance spectrum and legend illustrating the color change of a reactant(s) that may be used to determine glucose concentration in sweat, which may be correlated with blood glucose concentration. FIG. 18 shows an absorbance spectrum and legend illustrating the color change of a reactant(s) that may be used to determine lactate concentration in sweat, which may provide an indication of shock, hypoxia and/or exercise intolerance.

Figure 19:
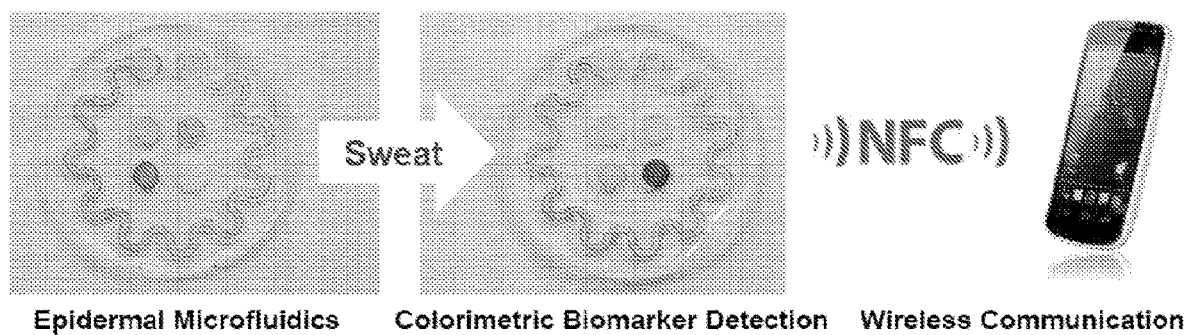
FIG. 19. A sweat sensor incorporating colorimetric biomarker indicators provides qualitative and quantitative data that may be observed by the naked eye and/or wirelessly observed by a detection device, such as a smartphone.

As shown in FIG. 19, a sweat sensor incorporating colorimetric biomarker indicators provides qualitative and quantitative data that may be observed by the naked eye and/or wirelessly observed by a detection device, such as a smartphone.

Example 3: Sweat Patches

Overview

Provided herein are epidermal microfluidic sweat patches for daily wear as personal healthcare monitoring systems that are highly conformable and stretchable. The patches allow for the non-invasive determination of sweat rate, sweat volume, and biomarker concentration, thereby providing clinically reliable information. This technology relates to self-diagnostic systems for monitoring an individual's health state by tracking color changes of indicators within the devices by the naked eye or with a portable electronic device (e.g., a smartphone). By monitoring changes over time or trends, the disclosed devices may provide early indications of abnormal conditions.

The disclosed sweat sensor enables detection of sweat volume and rate, as well as concentration of biomarkers in sweat (e.g., pH, glucose, lactate, chloride, creatinine and ethanol) via various quantitative colorimetric assays. In an embodiment, the colorimetric indicators are incorporated into a polydimethysiloxane (PDMS) substrate because PDMS is a silicon-based organic polymer approved for a wide range of medical applications, including contact lenses and medical devices.

Epidermal Microfluidics

Figure 21:
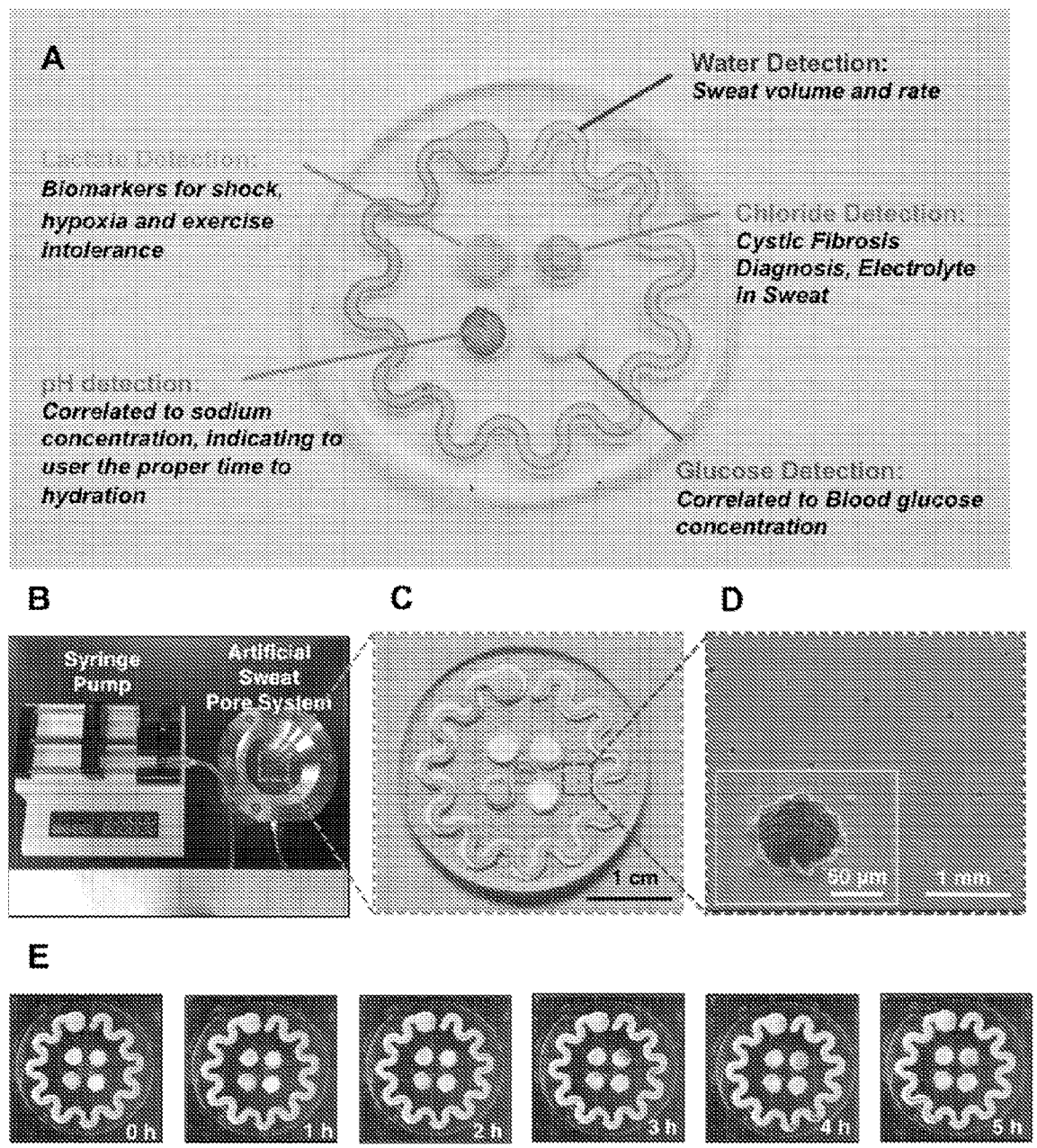
FIG. 21. (A) Picture of fabricated epidermal sweat sensor indicating informative detection schemes for sweat analysis. (B) In vitro artificial sweat pore system set up. (C) Optical image of sweat sensor applied on artificial pore membrane. (D) Scanning electron microscopy (SEM) image of the artificial pore membrane. Inset shows magnified image of single pore. (E) Representative images of sweat patch on the artificial sweat pore system while mimicking sweating events for 5 h. Sweat flowed continuously in the microfluidic systems along with color change accordingly.

Microfluidic analytical devices for sweat monitoring were developed based on a 2D channel system within poly (dimethylsiloxane) (PDMS) without pumps, valves, or fluid detectors. The chemical and physical characteristics of PDMS made it suitable for epidermal applications. For example, PDMS is optically transparent, elastomeric, non-toxic, chemically inert toward most reagents, and possesses a low surface energy.[1] The fabricated epidermal sweat patch was composed of four individual quantitative colorimetric detection reservoirs and an orbicular outer-circle serpentine fluidic channel (FIG. 21A). Each of the biomarker detection reservoirs holds 4 μL while the orbicular water detection channel contains 24 μL. The sample inlet located at the bottom of the device (0.5 cm$^2$) may cover about 50 sweat glands, thus introducing sweat into the device, filling the detection reservoirs, and allowing sweat to flow through the outer-circle channel for approximately 6 hours calculated based on an average sweat rate of 12 μL/hour·cm$^2$ for humans. Due to the interfacial permeability of PDMS, which is impermeable to liquid water but permeable to gases, the water loss of the sweat patch was moderate (3% of the total volume during the sensor life-time). The device was 3 cm in diameter and 500 μm in thickness constructed with PDMS consisting of 30:1 (v/v) base:curing agent resulting in a modulus of 145 kPa. The mass of the device was ~970 mg.

Figure 20:
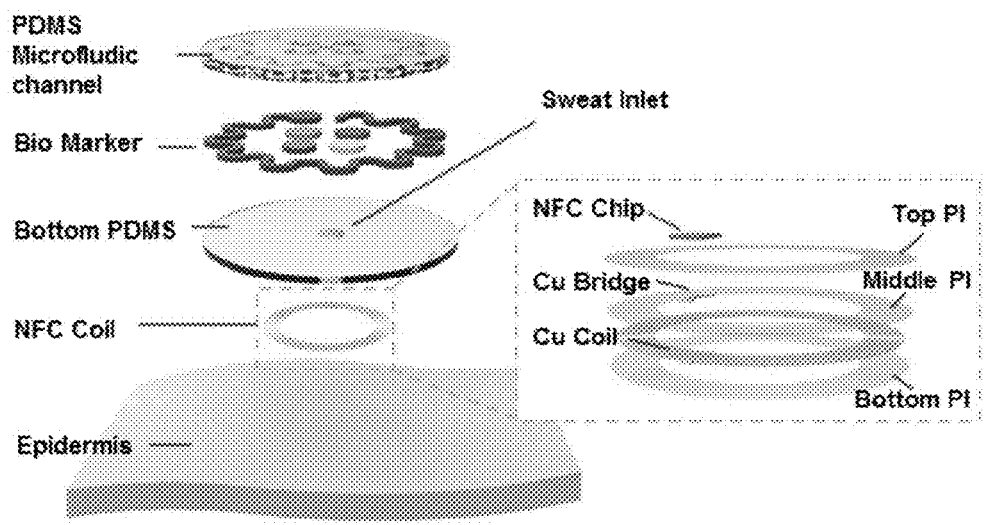
FIG. 20. (A) Schematic illustration of an epidermal microfluidic sweat sensor providing information of sweat volume and rate as well as concentration of biomarkers in sweat incorporated with wireless communication electronics. (B) Fabrication process for flexible and stretchable epidermal microfluidics. (C) Pictures of fabricated sweat sensors mounted on the skin under various mechanical stresses.
Figure 20:
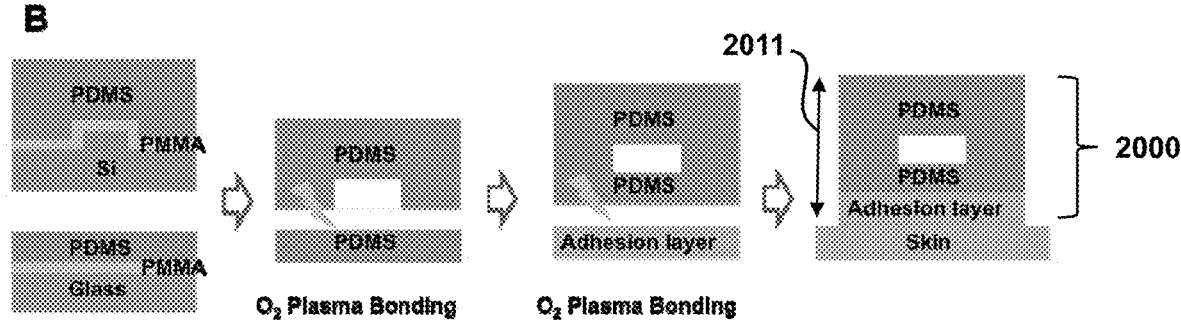
Figure 20:
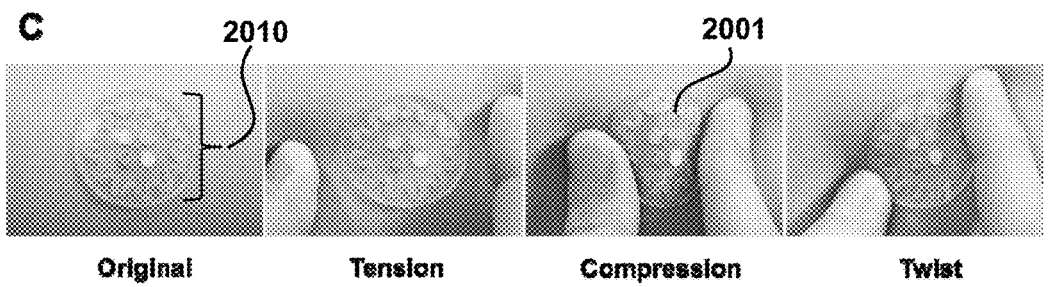

The epidermal microfluidic sweat sensors were fabricated using soft lithography. The schematic illustration and fabrication processes are shown in FIG. 20 with the device having an average modulus (reflected by element 2000), including less than or equal to 500 kPa, and a thickness 2011, including a modulus and thickness within a factor of 2 of a modulus 1001 and thickness 1011 of an epidermal layer of the skin of a subject (see FIG. 10), a net bending stiffness (reflected by element 2001) such as less than or equal to 1 nN m. The device has a footprint 2010, including selected from a range of 300 mm$^2$ to 2000 cm$^2$. A master device was prepared from a silicon wafer by photolithography and dip-etching to generate a reverse image having 300 μm deep channels. To produce replicas, the mixture of 30:1 (v/v) base:curing agent of PDMS was poured over the master that was coated with a thin layer of poly(methyl methacrylate) (PMMA) and cured at 70° C. for 1 h. Once the PDMS was fully cured, the replica was released from the master. The prepared replica was then sealed with a PDMS film by oxygen plasma bonding for 1 min to activate surface silanol groups to form siloxane bonds. Finally, the fabricated microfluidic devices were attached to a commercial medical dressing (i.e., Tegederm®) via oxygen plasma bonding and applied on the skin surface. This epidermal microfluidic sweat-monitoring device was able to withstand significant tension, compression, and twist of the skin while maintaining sufficient adhesion (FIG. 20C).

Quantitative Colorimetric Detection of Biomarkers

The colorimetric determination holds great advantages for diagnosis in quantitative analysis. In this sweat sensor, four colorimetric analyses were introduced for critical biomarkers being able to self-diagnosis and monitor a variety of medical conditions. Each detection reservoir represented a different analyte for determination of (1) water (for sweat volume and rate evaluation), (2) pH, (3) glucose, (4) lactate, and (5) chloride concentrations.

Figure 22:
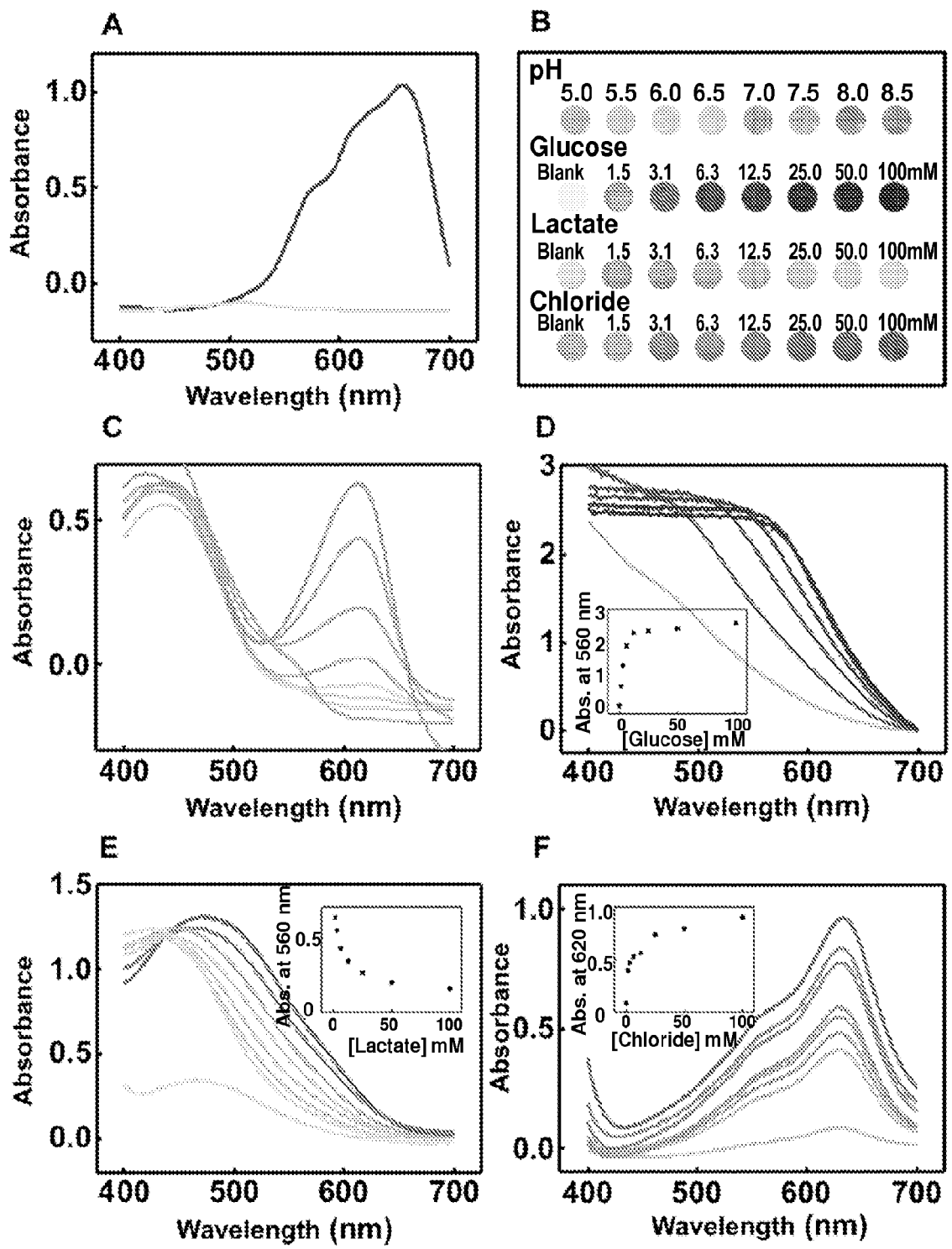
FIG. 22. Analytical colorimetric detections and respective UV-Vis spectrums of critical biomarkers in sweat. (A) Spectrum of anhydrous (blue) and hexahydrate (pale pink) cobalt (II) chloride. The presented color in the spectrum corresponds to the observed color with naked eye. (B) Optical images of resulted color change of the filter papers as a function of various pH values and analyte concentrations. (C) Spectrum of universal pH assay with various buffer solutions in the range of pH 5.0-8.5. (D-F) Spectrum of biomarkers in sweat as a function of concentration of analytes: glucose (D), lactate (E) and chloride (F). The presented color for each spectrum corresponds to exhibited color on paper-based colorimetric results, which is presented in image (B). Insets indicate calibration curves of respective analytes corresponding with concentration in the optical images (B). All spectra were determined at room temperature.

Thermal regulation and dehydration are highly related to sweat rate and volume and thus continuous monitoring is a vital tool for assessing health states of individuals and providing information relating to electrolyte balance and rehydration. The orbicular channel in the sweat sensor was coated with cobalt (II) chloride (i.e., $CoCl_2$) contained in a polyhydroxyethylmethacrylate hydrogel (pHEMA) matrix. As the sweat is introduced into the channel the blue colored anhydrous cobalt (II) chloride reacts with water turning into hexahydrate cobalt chloride (i.e., $CoCl_2.6H_2O$) presenting a pale purple color (FIG. 22A). By determining the distance of color change within the channel during a certain period of time, the sweat rate and volume could be assessed.

Not only physical sweat analysis, but chemical detection of biomarkers in sweat is essential. In some embodiments, quantitative colorimetric assays were demonstrated with paper-based reservoirs individually located in the middle of the sweat sensor. Filter paper was chosen as a matrix material among other materials (e.g., hydrogel, sol-gel, and agarose gel) since the hydrophilic cellulose fibers wicked biofluids at a fast absorption rate, as well as provided a solid support for assay reagent and allowed clear contrast regarding color changes.[2] A colorimetric sweat sensor was developed that consisted of four critical biomarker detection reservoirs: pH, glucose, lactate, and chloride.

The pH value of sweat has been known to exhibit a proportional relationship with sweat rate and sodium ion concentration. As an indicator of proper hydration time for a user, sweat pH was determined using a universal pH indicator consisting of various pH dyes (e.g., bromothymol blue, methyl red, and phenolphthalein), which covers a wide range of pH values. While the sweat was introduced in the reservoir, the pH indicator changed color based on the ratio of weak acid and its conjugate base form of the indicator based on the Henderson-Hasselbalch equation. The color change was observed according to various pH values of buffer solution in a medically reliable range (i.e., pH 4.0-7.0) as shown in FIG. 22B and its respective spectrum is presented in FIG. 22C.

Glucose concentration in the sweat is one of the most critical biomarkers for monitoring health state, especially playing a crucial role for improving diabetes treatment. In this device, the glucose was detected based on an enzymatic reaction that governed the selectivity of the measurement. Physically immobilized glucose oxidase produced hydrogen peroxide associated with oxidation of glucose and reduction of oxygen, next, iodide was oxidized to iodine by peroxidase, which was also contained in the paper-based reservoir.[3] Therefore, a color change was observed from yellow to brown, the respective colors of iodide and iodine, to indicate the concentration of glucose.[3] The color change illustrating the glucose concentration is presented in FIG. 22B as well as the respective spectrum in FIG. 22D. Thus, this device may warn of abnormal blood glucose concentrations for not only diabetes patients but also prediabetes and healthy persons by correlating perspiration glucose concentration in a completely noninvasive manner on a daily basis.[4]

The sweat lactate concentration is an indicator of exercise intolerance, tissue hypoxia, pressure ischemia, and even pathological conditions (e.g., cancer, diabetes, and lactate acidosis).[5] Lactate is produced by anaerobic energy metabolism from the eccrine gland, so lactate concentration in perspiration is a good criterion for determining individuals' abilities to endure rigorous exercise, especially for athletes and military personnel, and/or severe physical activity while on life support.[6] Enzymatic reactions between lactate and co-factor $NAD^+$ by lactate dehydrogenase and diaphorase allowed a color change of a chromogenic reagent (i.e., Formazan dyes) resulting in an orange color. As shown in FIGS. 22B and 22E, the color change within the detection reservoir was observed with regard to the concentration of lactate within the medically relevant range of 1.5-100 mM.

The representative sweat tests rely on determination of chloride ion concentration in perspiration. These tests may diagnosis cystic fibrosis (CF) since excreted chloride content increases when there are defective chloride channels in sweat glands.[7] Additionally, the level of chloride is considered to be an index of hydration. Accordingly, the level of chloride in sweat was determined using colorimetric detection by competitive binding between $Hg^{2+}$ and $Fe^{2+}$ with 2,4,6-tris(2-pyridiyl)-s-triazine (TPTZ). In the presence of chloride ion, iron ion prefers to bind with TPTZ while $Hg^{2+}$ participates as $HgCl_2$, which results in a color change from transparent to blue binding with respective metal ions. The quantitative colorimetric results are shown in FIGS. 22B and 22F.

Not only the biomarkers mentioned above, but copper ion, iron ion, and ethanol concentrations in sweat may also be detected by colorimetric assay. The trace copper ion in sweat was determined using a 1,2-bicinchoninate acid (BCA). The copper complex with BCA exhibited an intense purple color demonstrating a quantitative color change from 0 to 1 mg/mL.[8] Similarly, iron ions were detected by a colored complex formed with 1,10-phenanthroline in the range of 0-0.8 mg/L.[8b] Additionally, colorimetric detection of ethanol was demonstrated using an enzymatic reaction consisting of alcohol dehydrogenase, peroxidase, and formazan dye.

Collectively, these quantitative colorimetric analyses provide pre-diagnostic information of multiple biomarkers in sweat. By combining the colorimetric devices with telemedicine technology, this sweat patch could provide a user-friendly self-monitoring system for daily wear.

Telemedicine Technologies

Figure 23:
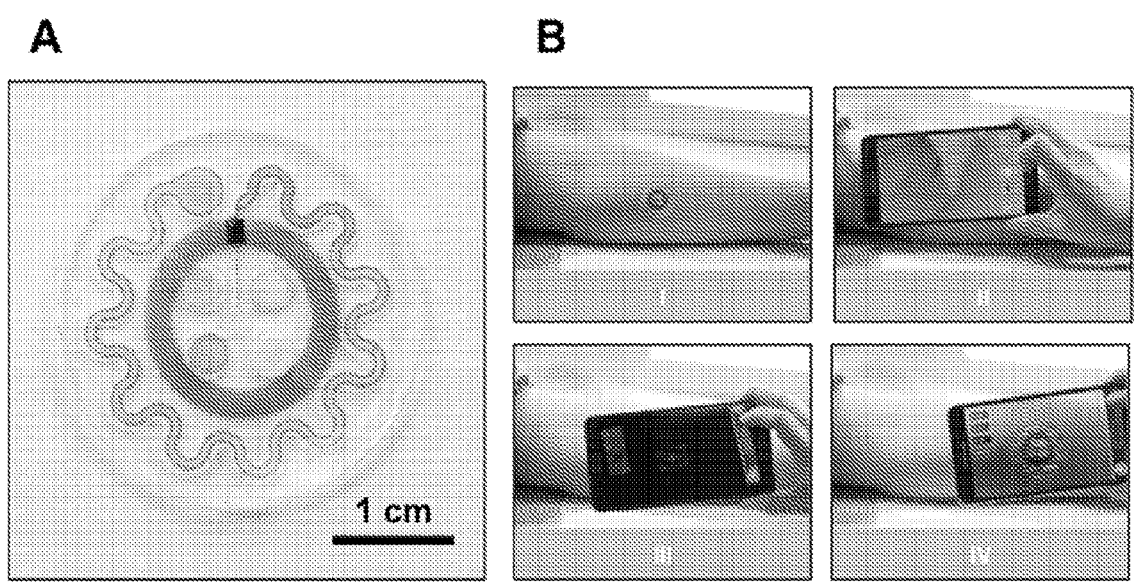
FIG. 23. (A) An image of fabricated sweat sensor incorporated with near-field communication electronics. (B) Demonstration pictures of wireless communication via smartphone. The RGB information was determined using an android image analysis app.

In order to provide personalized clinical health care with a smartphone, near field communication (NFC) electronics were applied to the sweat patch. The NFC communication devices were fabricated with an ultrathin construction using ultralow modulus materials, which enable wireless communication under extreme deformations in daily usage.[9] The NFC coils were incorporated on the sweat patch as shown in FIG. 23A. The biomedical information of sweat is quantitatively analyzed by taking images of the sweat sensor showing the color changes of the reservoirs (FIG. 23B). Using wireless NFC electronics to communicate to a smartphone permits the images to be examined based on an RGB digital color specification, converted into health informatics (e.g., concentration of biomarkers) and optionally transmitted from an individual's smartphone to medical staff or a medical records database.

REFERENCES

1. McDonald, J. C.; Whitesides, G. M., Poly(dimethylsiloxane) as a Material for Fabricating Microfluidic Devices. Accounts of Chemical Research 2002, 35 (7), 491-499.
2. Martinez, A. W.; Phillips, S. T.; Whitesides, G. M.; Carrilho, E., Diagnostics for the Developing World:

Microfluidic Paper-Based Analytical Devices. Analytical Chemistry 2010, 82 (1), 3-10.
3. (a) Martinez, A. W.; Phillips, S. T.; Butte, M. J.; Whitesides, G. M., Patterned Paper as a Platform for Inexpensive, Low-Volume, Portable Bioassays. Angewandte Chemie International Edition 2007, 46 (8), 1318-1320; (b) Martinez, A. W.; Phillips, S. T.; Carrilho, E.; Thomas, S. W.; Sindi, H.; Whitesides, G. M., Simple Telemedicine for Developing Regions: Camera Phones and Paper-Based Microfluidic Devices for Real-Time, Off-Site Diagnosis. Analytical Chemistry 2008, 80 (10), 3699-3707.
4. Moyer, J.; Wilson, D.; Finkelshtein, I.; Wong, B.; Potts, R., Correlation Between Sweat Glucose and Blood Glucose in Subjects with Diabetes. Diabetes Technology & Therapeutics 2012, 14 (5), 398-402.
5. (a) Polliack, A.; Taylor, R.; Bader, D., Sweat analysis following pressure ischaemia in a group of debilitated subjects. J Rehabil Res Dev 1997, 34 (3), 303-308; (b) Biagi, S.; Ghimenti, S.; Onor, M.; Bramanti, E., Simultaneous determination of lactate and pyruvate in human sweat using reversed-phase high-performance liquid chromatography: a noninvasive approach. Biomedical Chromatography 2012, 26 (11), 1408-1415.
6. Jia, W.; Bandodkar, A. J.; Valdes-Ramirez, G.; Windmiller, J. R.; Yang, Z.; Ramirez, J.; Chan, G.; Wang, J., Electrochemical tattoo biosensors for real-time noninvasive lactate monitoring in human perspiration. Anal Chem 2013, 85 (14), 6553-60.
7. Mishra, A.; Greaves, R.; Massie, J., The Relevance of Sweat Testing for the Diagnosis of Cystic Fibrosis in the Genomic Era. The Clinical biochemist. Reviews/Australian Association of Clinical Biochemists. 2005, 26 (4), 135-153.
8. (a) Brenner, A. J.; Harris, E. D., A quantitative test for copper using bicinchoninic acid. Anal Biochem 1995, 226 (1), 80-4; (b) Huang, X.; Liu, Y. H.; Chen, K. L.; Shin, W. J.; Lu, C. J.; Kong, G. W.; Patnaik, D.; Lee, S. H.; Cortes, J. F.; Rogers, J. A., Stretchable, Wireless Sensors and Functional Substrates for Epidermal Characterization of Sweat. Small 2014, 10 (15), 3083-3090.
9. Kim, J.; Banks, A.; Cheng, H. Y.; Xie, Z. Q.; Xu, S.; Jang, K. I.; Lee, J. W.; Liu, Z. J.; Gutruf, P.; Huang, X.; Wei, P. H.; Liu, F.; Li, K.; Dalal, M.; Ghaffari, R.; Feng, X.; Huang, Y. G.; Gupta, S.; Paik, U.; Rogers, J. A., Epidermal Electronics with Advanced Capabilities in Near-Field Communication. Small 2015, 11 (8), 906-912.

Example 4: Additional Sweat Patches

Figure 24:
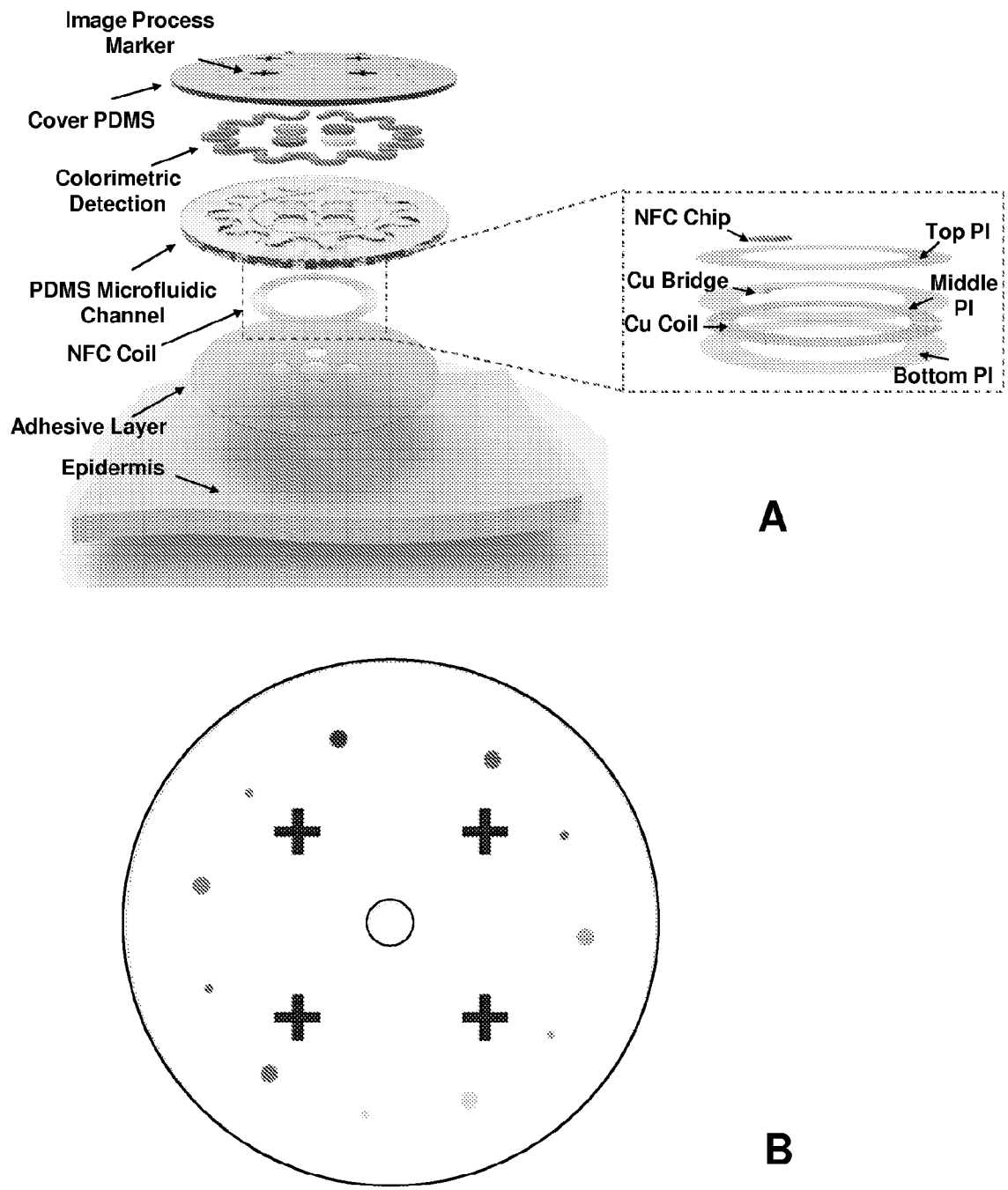
FIG. 24. (A) Schematic illustration of an epidermal microfluidic sweat sensor providing information on sweat volume and rate as well as concentration of biomarkers in sweat incorporated with wireless communication electronics and an adhesive layer. (B) Schematic illustration of image process markers applied to an epidermal microfluidic sweat sensor.

FIG. 24(A) shows a schematic illustration of an epidermal microfluidic sweat sensor providing information on sweat volume and rate as well as concentration of biomarkers in sweat incorporated with wireless communication electronics and an adhesive layer for adhering the sensor to the epidermis of a subject. FIG. 24(B) shows a schematic illustration of image process markers applied to an epidermal microfluidic sweat sensor. Image process markers are laminated on or disposed in a top layer of the sensor for white balance and color calibration, which enables the sensors to function under various light conditions. The image process markers also provide a reference for device orientation and a borderline for color change within a channel.

Figure 25:
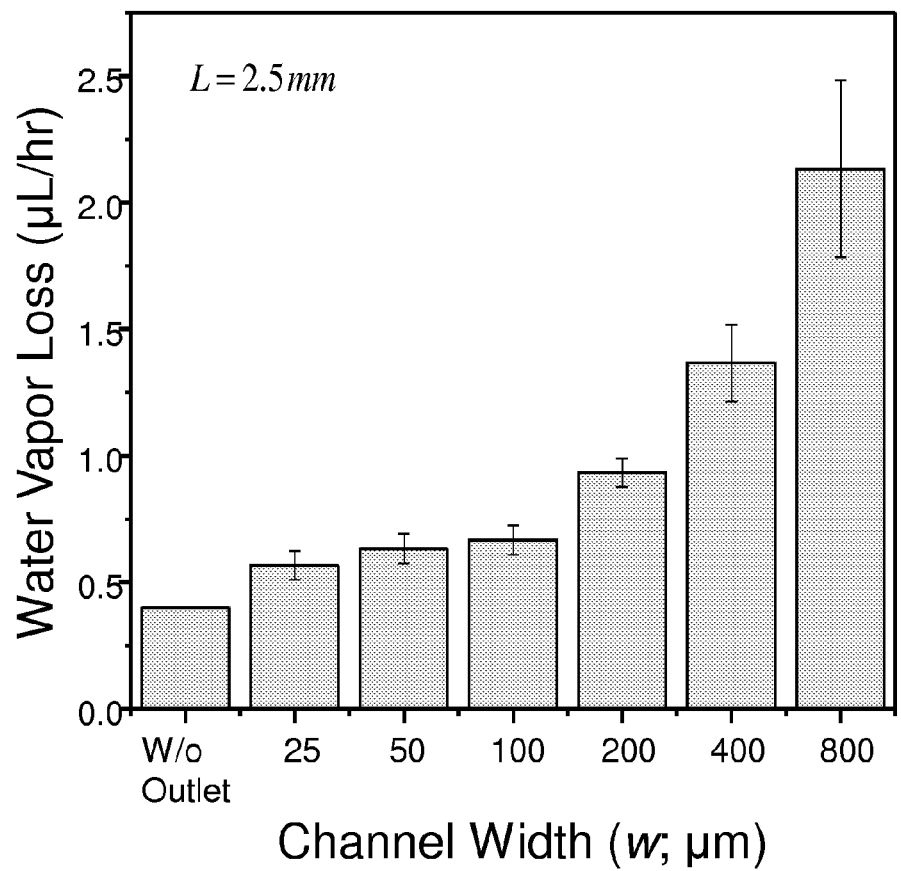
FIG. 25. Graphical representation of water loss as a function of outlet channel (A) width and (B) length.
Figure 25:
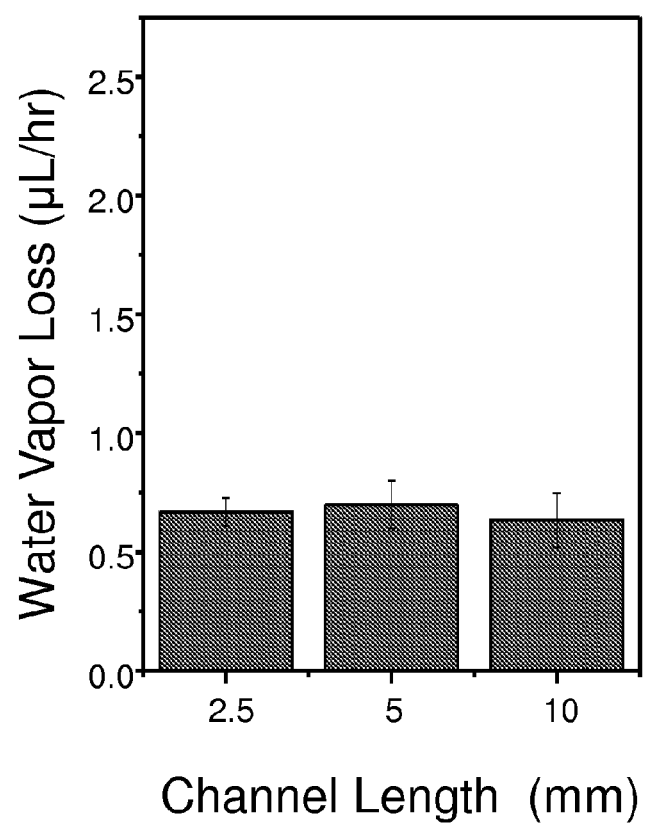
Figure 26:
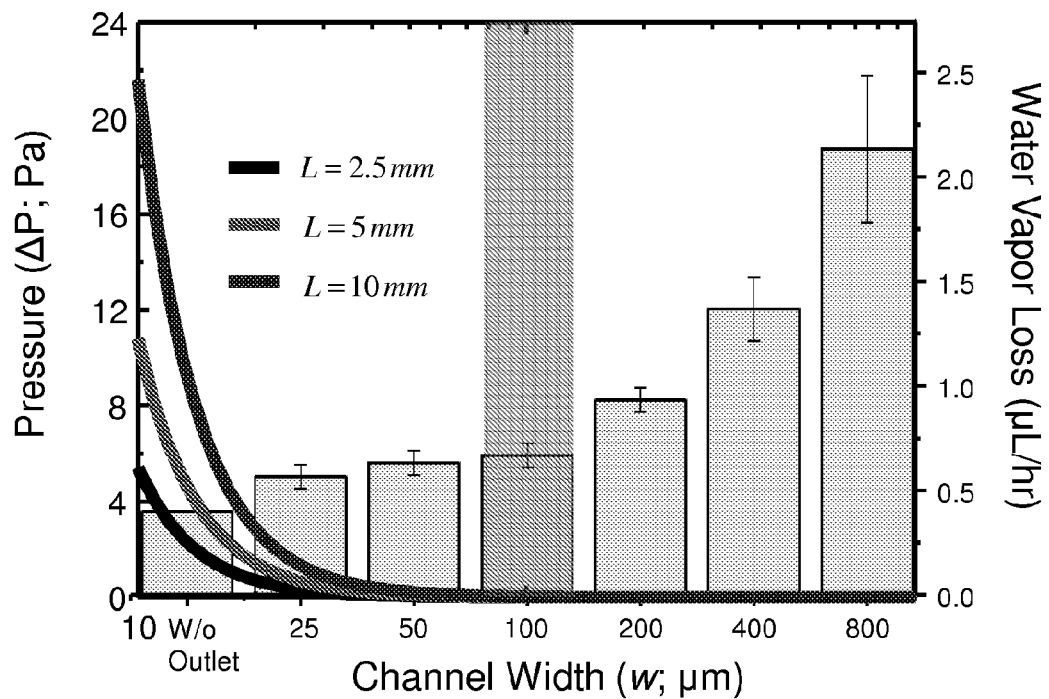
FIG. 26. Graphical representation of back pressure inside a channel showing that shorter outlet channels and larger channel widths produce lower back pressures.

FIG. 25 provides graphical representations of water loss as a function of outlet channel (A) width and (B) length. Smaller channel widths generally lead to a lower rate of water vapor loss than larger channel widths, but channel length does not significantly affect the rate of water vapor loss. FIG. 26 provides a graphical representation of back pressure inside a channel showing that shorter outlet channels and larger channel widths produce lower back pressures. At a channel width of 100 µm, back pressure became negligible for all channel lengths studied. The following equation was used to calculate the theoretical pressure in the channel:

$$\nabla P \approx \frac{8L(w=h)^2}{w^3 h^3} \frac{\mu M}{\rho} \frac{\dot{V}_{inlet} P_0}{RT} \qquad (15)$$

where h=300 µm, M=29E-3 Kg/mol, $\rho$=1.2 Kg/m$^3$, $\mu$=1.8E-5 Pa·s, $P_0$=1E5 Pa, $V_{in}$=15 µL/hour, R=8.314 J/(mol·K), T=300 K.

Figure 27:
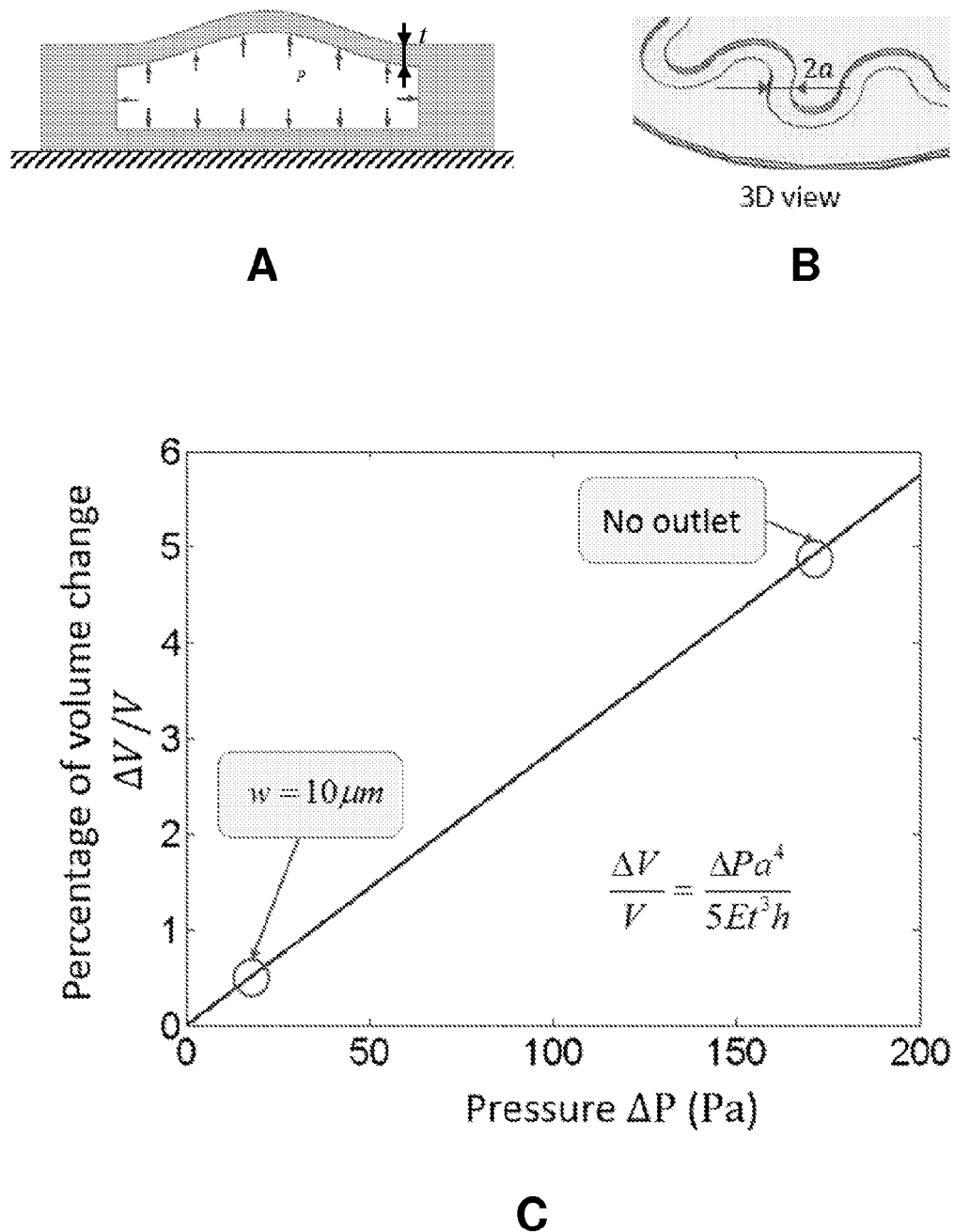
FIG. 27. (A) Schematic illustration of a cross section of a microfluidic channel deformed due to pressure. (B) Schematic illustration of a top perspective view of a section of an epidermal microfluidic sweat sensor showing a width of the microfluidic channel. (C) Graphical representation of deformation shown as volume change due to pressure.

FIG. 27 shows a schematic illustration of a cross section of a microfluidic channel deformed due to pressure (A) and a top perspective view of a section of an epidermal microfluidic sweat sensor showing a width of the microfluidic channel (B), as well as a graphical representation of deformation shown as volume change due to pressure. The volume change was calculated using:

$$\frac{\Delta V}{V} = \frac{\nabla P a^4}{5 E t^3 h} \qquad (16)$$

where 2a=1 mm, t=100 µm, E=145 KPa and v=0.5. At an outlet width greater than 10 µm, a pressure-induced volume change can be avoided.

Figure 28:
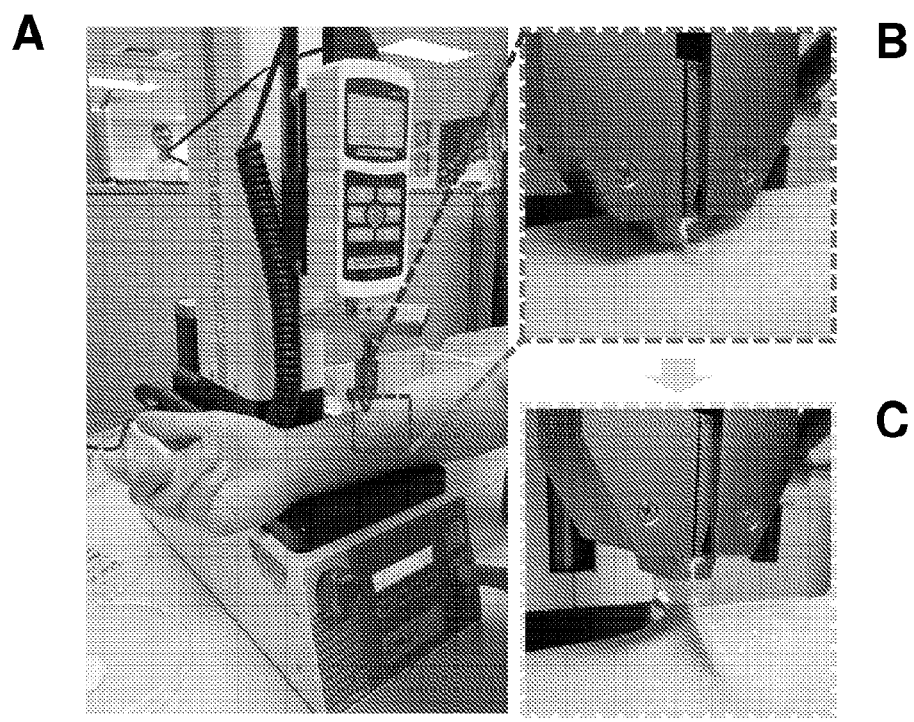
FIG. 28. (A) Experimental set-up for 90° peel adhesion property testing (standard ISO 29862:2007) using a force gauge (Mark-10, Copiague, N.Y.). Images of (B) holding devices adhered on the skin with a force gauge and (C) peeling devices at an angle of 90°. (D) Force measurement while displacing the device at a rate of 300 mm/min indicated by the gray region where peeling occurs. Determined average peeling force is 5.7 N.
Figure 28:
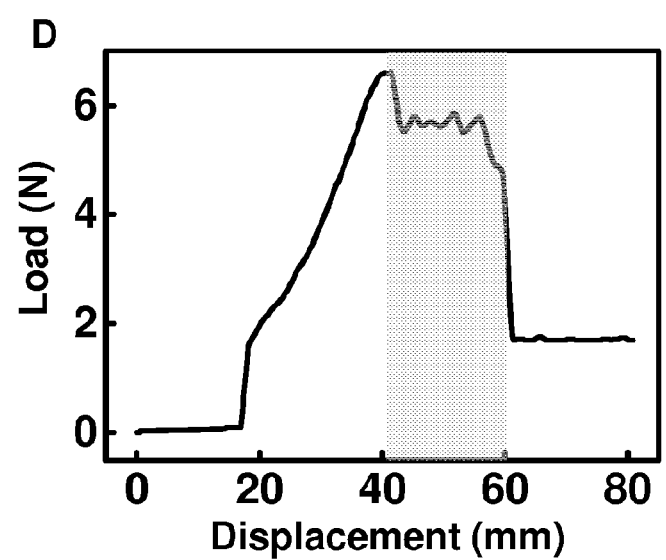

To harvest biofluids using pump-less microfluidics, sufficient adhesion force is required to drive fluid into the microfluidics system. The disclosed microfluidic devices demonstrate great adhesion on the epidermis facilitated by medical-grade adhesives (e.g., Tagaderm®). FIG. 28 shows an experimental set-up for 90° peel adhesion property testing (standard ISO 29862:2007) using a force gauge (Mark-10, Copiague, N.Y.) (A). A holding devices is adhered on the skin with a force gauge (B) and devices are peeled at an angle of 90° (C.). The force measurement while displacing the device at a rate of 300 mm/min is shown graphically in (D) and the area where peeling occurs is indicated by the gray region. The average peeling force was determined to be 5.7 N. Thus, the disclosed microfluidic sweat sensors may be bonded to the epidermis of a subject with an adhesion force in the range from 1 N to 10 N, or 2 N to 8 N, or 3 N to 6 N.

Figure 29:
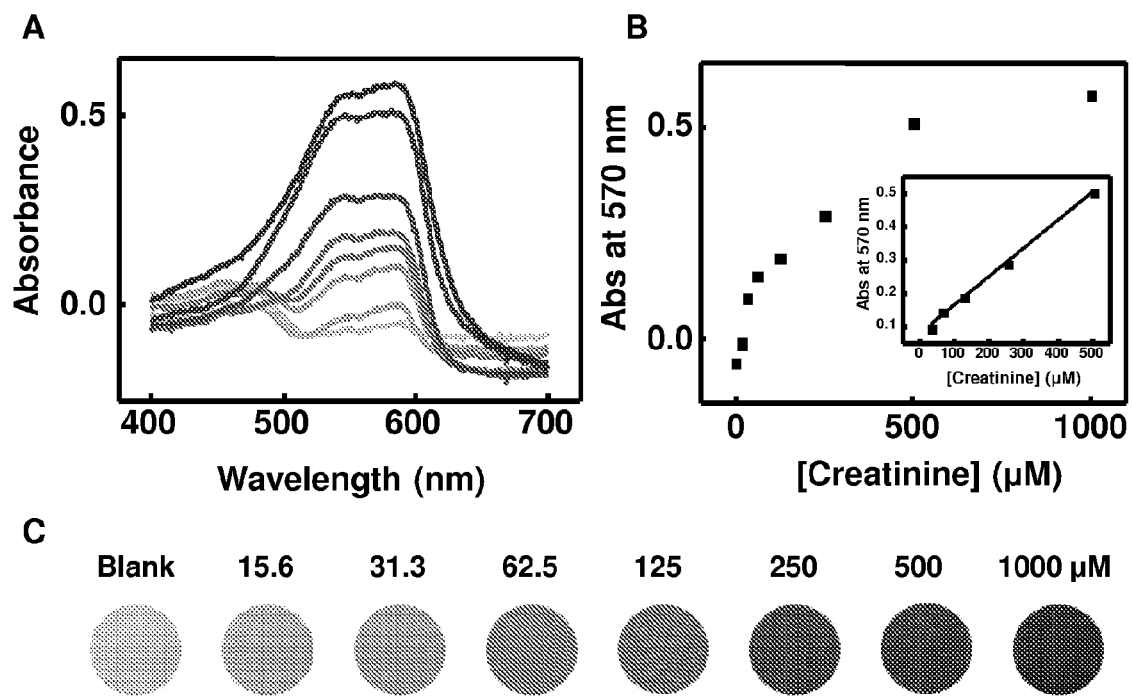
FIG. 29. Colorimetric determination of creatinine. (A) UV-VIS spectrum with various creatinine concentrations (i.e., 15-1000 µM) and (B) constructed calibration based on this spectrum. The presented color for each spectrum corresponds to exhibited color on paper-based colorimetric detection reservoirs as a function of creatinine concentration, which is presented in optical image (C).

FIG. 29 illustrates one example of colorimetric determination of creatinine. A UV-VIS spectrum illustrating various creatinine concentrations (i.e., 15-1000 µM) is shown in (A) and a constructed calibration curve based on this spectrum is shown in (B). The presented color for each spectrum corresponds to exhibited color on paper-based colorimetric detection reservoirs as a function of creatinine concentration, which is presented in optical image (C). This colorimetric analysis is based on an enzymatic reaction using a mixture of creatinine amidohydrolase, creatine amidinohydrolase and sarcosine oxidase. Reaction of creatinine with this enzyme mixture generates hydrogen peroxide proportional to the concentration of creatinine in biological fluids. The hydrogen peroxide concentration is determined colorimetrically by the chromogen 2,5-dichloro-2-hydroxybenzenesulfonic acid and 4-amino-phenazone in a reaction catalyzed by horseradish peroxidase.

Figure 30:
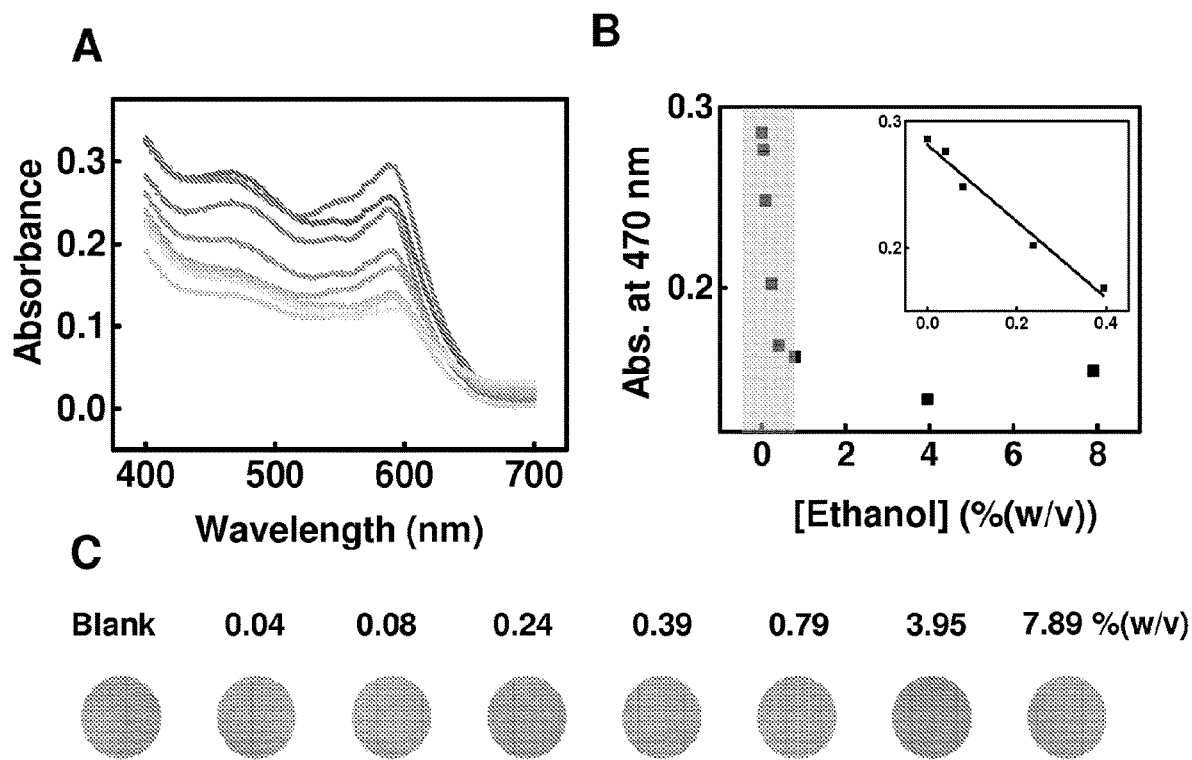
FIG. 30. Colorimetric determination of ethanol. (A) UV-VIS spectrum with various ethanol concentrations (i.e., 0.04-7.89% (w/v)) and (B) constructed calibration based on this spectrum. The presented color for each spectrum corresponds to exhibited color on paper-based colorimetric detection reservoirs as a function of ethanol concentration, which is presented in optical image (C).

FIG. 30 illustrates one example of colorimetric determination of ethanol. Ethanol is detected via reaction with alcohol dehydrogenase in the presence of formazan dye. A UV-VIS spectrum illustrating various ethanol concentrations (i.e., 0.04-7.89% (w/v)) is shown in (A) and a constructed calibration curve based on this spectrum is shown in (B). The presented color for each spectrum corresponds to exhibited color on paper-based colorimetric detection reservoirs as a function of ethanol concentration, which is presented in optical image (C).

Figure 31:
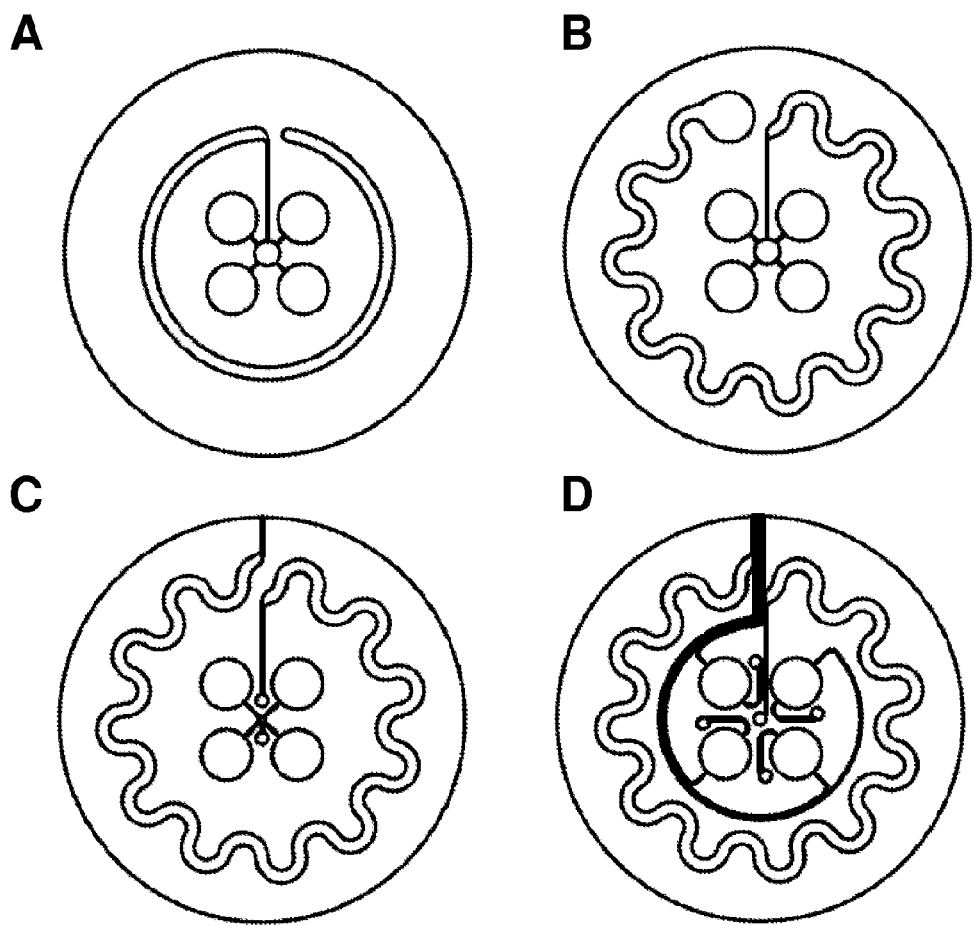
FIG. 31. (A)-(D) Various microfluidic sweat sensor designs.
Figure 32:
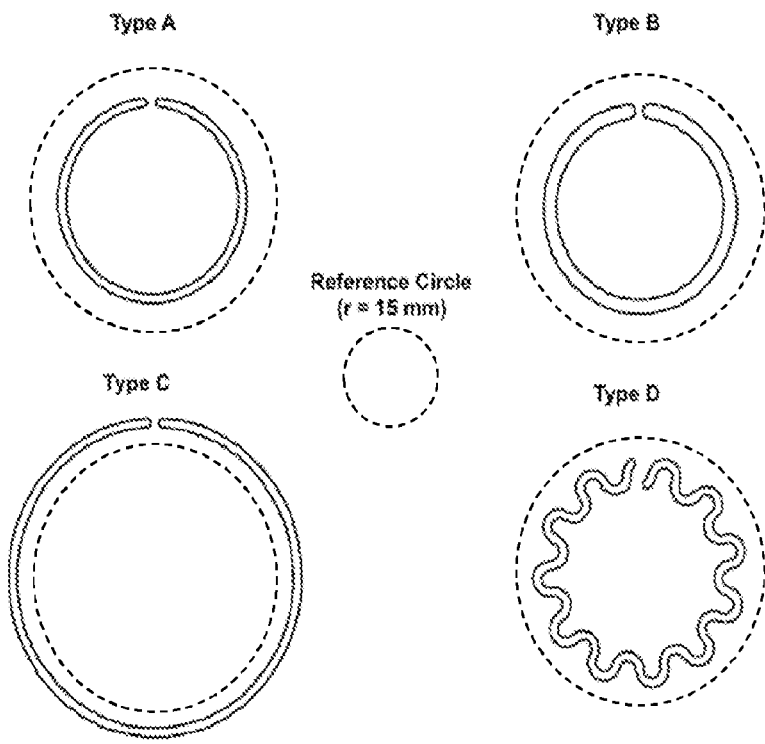
FIG. 32. Various types of orbicular channel designs and respectively calculated channel properties.

FIG. 31 shows various microfluidic sweat sensor designs including four individual quantitative colorimetric detection reservoirs and an orbicular outer-circle fluidic channel. In some embodiments, a single microfluidic channel is in fluidic communication with all of the colorimetric detection reservoirs and an orbicular fluidic channel. In an other embodiment, one microfluidic channel transports fluids from the epidermis of a subject to the colorimetric detection reservoirs and a second microfluidic channel transports fluids from the epidermis of the subject to the orbicular fluidic channel (C). In another embodiment, each colorimetric detection reservoir and the orbicular microfluidic channel may be independently connected to a microfluidic channel that transports fluid from the epidermis of a subject. Optionally, each of the colorimetric detection reservoirs may comprise an outlet to a channel that allows vapor to escape to the surrounding environment. As shown in (D), the outlet channel may be tapered to increase in volume nearer the outlet to the surrounding environment, thereby accommodating larger quantities of vapor without increasing back pressure within the outlet channel. In any of the embodiments disclosed, the orbicular fluidic channel may be circular or serpentine and the orbicular fluidic channel may have a sealed distal end, optionally including a reservoir, or an outlet to the surrounding environment. As shown in FIG. 32, a serpentine orbicular fluidic channel provides a greater area and channel volume than a circular orbicular fluidic channel while controlling for channel width and height to avoid collapse of the channel. For example, a serpentine channel may provide an increased area of up to 58% compared to a circular channel having an identical channel width. An increased area of the orbicular channel increases the amount of time a microfluidic sweat sensor can be used for monitoring a subject without being replaced or dried.

STATEMENTS REGARDING INCORPORATION BY REFERENCE AND VARIATIONS

All references throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods and steps set forth in the present description. As will be obvious to one of skill in the art, methods and devices useful for the present embodiments can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

The following references relate generally to fabrication methods, structures and systems for making electronic devices, and are hereby incorporated by reference to the extent not inconsistent with the disclosure in this application.

| Application No. | Filing Date | Publication No. | Publication Date | Patent No. | Issue Date |
|---|---|---|---|---|---|
| 11/001,689 | Dec. 1, 2004 | 2006/0286488 | Dec. 21, 2006 | 7,704,684 | Apr. 27, 2010 |
| 11/115,954 | Apr. 27, 2005 | 2005/0238967 | Oct. 27, 2005 | 7,195,733 | Mar. 27, 2007 |
| 11/145,574 | Jun. 2, 2005 | 2009/0294803 | Dec. 3, 2009 | 7,622,367 | Nov. 24, 2009 |
| 11/145,542 | Jun. 2, 2005 | 2006/0038182 | Feb. 23, 2006 | 7,557,367 | Jul. 7, 2009 |
| 11/421,654 | Jun. 1, 2006 | 2007/0032089 | Feb. 8, 2007 | 7,799,699 | Sep. 21, 2010 |
| 11/423,287 | Jun. 9, 2006 | 2006/0286785 | Dec. 21, 2006 | 7,521,292 | Apr. 21, 2009 |
| 11/423,192 | Jun. 9, 2006 | 2009/0199960 | Aug. 13, 2009 | 7,943,491 | May 17, 2011 |

-continued

| Application No. | Filing Date | Publication No. | Publication Date | Patent No. | Issue Date |
| --- | --- | --- | --- | --- | --- |
| 11/465,317 | Aug. 17, 2006 | — | — | — | — |
| 11/675,659 | Feb. 16, 2007 | 2008/0055581 | Mar. 6, 2008 | — | — |
| 11/782,799 | Jul. 25, 2007 | 2008/0212102 | Sep. 4, 2008 | 7,705,280 | Apr. 27, 2010 |
| 11/851,182 | Sep. 6, 2007 | 2008/0157235 | Jul. 3, 2008 | 8,217,381 | Jul. 10, 2012 |
| 11/585,788 | Sep. 20, 2007 | 2008/0108171 | May 8, 2008 | 7,932,123 | Apr. 26, 2011 |
| 11/981,380 | Oct. 31, 2007 | 2010/0283069 | Nov. 11, 2010 | 7,972,875 | Jul. 5, 2011 |
| 12/372,605 | Feb. 17, 2009 | — | — | — | — |
| 12/398,811 | Mar. 5, 2009 | 2010/0002402 | Jan. 7, 2010 | 8,552,299 | Oct. 8, 2013 |
| 12/405,475 | Mar. 17, 2009 | 2010/0059863 | Mar. 11, 2010 | 8,198,621 | Jun. 12, 2012 |
| 12/418,071 | Apr. 3, 2009 | 2010/0052112 | Mar. 4, 2010 | 8,470,701 | Jun. 25, 2013 |
| 12/522,582 | Jul. 9, 2009 | — | — | — | — |
| 12/564,566 | Sep. 22, 2009 | 2010/0072577 | Mar. 25, 2010 | 7,982,296 | Jul. 19, 2011 |
| 12/669,287 | Jan. 15, 2010 | 2011/0187798 | Aug. 4, 2011 | — | — |
| 12/778,588 | May 12, 2010 | 2010/0317132 | Dec. 16, 2010 | — | — |
| 12/844,492 | Jul. 27, 2010 | 2010/0289124 | Nov. 18, 2010 | 8,039,847 | Oct. 18, 2011 |
| 12/892,001 | Sep. 28, 2010 | 2011/0230747 | Sep. 22, 2011 | 8,666,471 | Mar. 4, 2014 |
| 12/916,934 | Nov. 1, 2010 | 2012/0105528 | May 3, 2012 | 8,562,095 | Oct. 22, 2013 |
| 12/947,120 | Nov. 16, 2010 | 2011/0170225 | Jul. 14, 2011 | — | — |
| 12/996,924 | Dec. 8, 2010 | 2011/0147715 | Jun. 23, 2011 | 8,946,683 | Feb. 3, 2015 |
| 12/968,637 | Dec. 15, 2010 | 2012/0157804 | Jun. 21, 2012 | — | — |
| 13/046,191 | Mar. 11, 2011 | 2012/0165759 | Jun. 28, 2012 | — | — |
| 13/071,027 | Mar. 24, 2011 | 2011/0171813 | Jul. 14, 2011 | — | — |
| 13/095,502 | Apr. 27, 2011 | — | — | — | — |
| 13/100,774 | May 4, 2011 | 2011/0266561 | Nov. 3, 2011 | 8,722,458 | May 13, 2014 |
| 13/113,504 | May 23, 2011 | 2011/0220890 | Sep. 15, 2011 | 8,440,546 | May 14, 2013 |
| 13/120,486 | Aug. 4, 2011 | 2011/0277813 | Nov. 17, 2011 | 8,679,888 | Mar. 25, 2014 |
| 13/228,041 | Sep. 8, 2011 | 2011/0316120 | Dec. 29, 2011 | — | — |
| 13/270,954 | Oct. 11, 2011 | 2012/0083099 | Apr. 5, 2012 | 8,394,706 | Mar. 12, 2013 |
| 13/349,336 | Jan. 12, 2012 | 2012/0261551 | Oct. 18, 2012 | — | — |
| 13/441,618 | Apr. 6, 2012 | 2013/0100618 | Apr. 25, 2013 | 8,754,396 | Jun. 17, 2014 |
| 13/441,598 | Apr. 6, 2012 | 2012/0327608 | Dec. 27, 2012 | 8,729,524 | May 20, 2014 |
| 13/472,165 | May 15, 2012 | 2012/0320581 | Dec. 20, 2012 | — | — |
| 13/486,726 | Jun. 1, 2012 | 2013/0072775 | Mar. 21, 2013 | 8,934,965 | Jan. 13, 2015 |
| 13/492,636 | Jun. 8, 2012 | 2013/0041235 | Feb. 14, 2013 | — | — |
| 13/549,291 | Jul. 13, 2012 | 2013/0036928 | Feb. 14, 2013 | — | — |
| 13/596,343 | Aug. 28, 2012 | 2012/0321785 | Dec. 20, 2012 | 8,367,035 | Feb. 5, 2013 |
| 13/624,096 | Sep. 21, 2012 | 2013/0140649 | Jun. 6, 2013 | — | — |
| 13/801,868 | Mar. 13, 2013 | 2013/0320503 | Dec. 5, 2013 | 8,664,699 | Mar. 4, 2014 |
| 13/835,284 | Mar. 15, 2013 | 2014/0220422 | Aug. 7, 2014 | — | — |
| 13/853,770 | Mar. 29, 2013 | 2013/0333094 | Dec. 19, 2013 | — | — |
| 13/974,963 | Aug. 23, 2013 | 2014/0140020 | May 22, 2014 | 8,905,772 | Dec. 9, 2014 |
| 14/033,765 | Sep. 23, 2013 | 2014/0092158 | Apr. 3, 2014 | — | — |
| 14/140,299 | Dec. 24, 2013 | 2014/0163390 | Jun. 12, 2014 | — | — |
| 14/155,010 | Jan. 14, 2014 | 2014/0191236 | Jul. 10, 2014 | — | — |
| 14/173,525 | Feb. 5, 2014 | 2014/0216524 | Aug. 7, 2014 | — | — |
| 14/209,481 | Mar. 13, 2014 | 2014/0373898 | Dec. 25, 2014 | — | — |
| 14/220,910 | Mar. 20, 2014 | 2014/0374872 | Dec. 25, 2014 | — | — |
| 14/220,923 | Mar. 20, 2014 | 2015/0001462 | Jan. 1, 2015 | — | — |
| 14/246,962 | Apr. 7, 2014 | 2014/0361409 | Dec. 11, 2014 | — | — |
| 14/250,671 | Apr. 11, 2014 | 2014/0305900 | Oct. 16, 2014 | — | — |
| 14/251,259 | Apr. 11, 2014 | 2014/0323968 | Oct. 30, 2014 | — | — |
| 12/778,588 | Sep. 5, 2014 | 2015/0132873 | May 14, 2015 | — | — |
| 14/504,736 | Oct. 2, 2014 | 2015/0141767 | May 21, 2015 | — | — |
| 14/521,319 | Oct. 22, 2014 | — | — | — | — |
| 14/532,687 | Nov. 4, 2014 | 2015/0080695 | Mar. 19, 2015 | — | — |
| 14/599,290 | Jan. 16, 2015 | — | — | — | — |
| 12/669,287 | Apr. 14, 2015 | — | — | — | — |
| 12/398,811 | May 7, 2015 | — | — | — | — |
| PCT/US2014/015825 | Feb. 19, 2014 | WO2014/126927 | Aug. 21, 2014 | — | — |
| PCT/US2014/014932 | Feb. 5, 2014 | WO 2014/124044 | Aug. 14, 2014 | — | — |
| PCT/US2014/014944 | Feb. 18, 2014 | WO 2014/124049 | Aug. 14, 2014 | — | — |
| PCT/US2014/021371 | Mar. 6, 2014 | WO 2014/138465 | Sep. 12, 2014 | — | — |
| PCT/US2014/032848 | Apr. 3, 2014 | WO 2014/165686 | Oct. 9, 2014 | — | — |

Every formulation or combination of components described or exemplified herein can be used to practice the invention, unless otherwise stated.

Whenever a range is given in the specification, for example, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements and/or limitation or limitations, which are not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

We claim:

1. A device for monitoring a biofluid that is sweat comprising:
a functional substrate that is mechanically matched to skin for establishing conformal contact with skin; wherein said functional substrate provides for microfluidic transport of sweat released from sweat glands through a sweat inlet positioned at a surface of said functional substrate; and
a plurality of sensors supported by said functional substrate, and a plurality of cavities of said functional substrate, wherein each of said plurality of sensors comprise a colorimetric indicator disposed within a respective cavity of the plurality of cavities;
wherein each of said cavities are connected to said sweat inlet by a microfluidic channel for detection of multiple biomarkers in said sweat, and said sweat released from sweat glands flows along the microfluidic channel to said cavities, wherein each colorimetric indicator detects concentration of: glucose, lactate, chloride, creatinine and/or ethanol; and
a sweat volume channel for gauging sweat volume, said sweat volume channel being transparent and configured to fill with sweat from a first end and display a distance traveled by sweat from said first end along the channel, wherein said distance traveled by sweat corresponds to volume of sweat collected.

2. The device of claim 1 further comprising a component for extracting interstitial fluid or blood from a subject.

3. The device of claim 2, wherein the component for extracting interstitial fluid or blood is selected from the group consisting of: a microneedle component, a reverse iontophoresis component and a thermal microabrasion component.

4. The device of claim 1, wherein said functional substrate is substantially colorless and substantially transparent.

5. The device of claim 1, wherein said functional substrate has a modulus less than or equal to 100 MPa.

6. The device of claim 1, wherein said functional substrate has a thickness selected from a range of 500 μm to 2 mm.

7. The device of claim 1, wherein said functional substrate is selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA) and polycarbonate.

8. The device of claim 1, wherein said functional substrate has a dielectric constant greater than or equal to 2.0.

9. The device of claim 1, wherein said functional substrate has lateral dimensions or a diameter less than or equal to 700 mm.

10. The device of claim 1, wherein said functional substrate has a permeability for said biofluid greater than or equal to 0.2 g/h m$^2$.

11. The device of claim 1, wherein said functional substrate has a coefficient of thermal expansion selected from a range of 1/° C. ($\times 10^{-6}$) to 3/° C. ($\times 10^{-4}$).

12. The device of claim 1, wherein said functional substrate has a porosity greater than or equal to 0.5.

13. The device of claim 1, wherein said microfluidic transport is spontaneous microfluidic transport via capillary force.

14. The device of claim 1 further comprising at least one microfluidic channel having a substantially uniform lateral dimension.

15. The device of claim 1, wherein said microfluidic channel has a length selected from a range of 1 mm to 7 cm and/or a width selected from a range of 100 μm to 1 mm.

16. The device of claim 1, further comprising a component for extracting blood from a subject.

17. The device of claim 1, wherein at least one sensor is a pH colorimetric indicator.

18. The device of claim 1, wherein said sensor comprises an electrical sensor, a chemical sensor, a biological sensor, a temperature sensor, an impedance sensor, an optical sensor, a mechanical sensor or a magnetic sensor.

19. The device of claim 1, wherein said sensor is an LC resonator.

20. The device of claim 1 further comprising an actuator.

21. The device of claim 20, wherein said actuator generates electromagnetic radiation, acoustic energy, an electric field, a magnetic field, heat, a RF signal, a voltage, a chemical change or a biological change.

22. The device of claim 20, wherein said actuator comprises a heater, a reservoir containing a chemical agent capable of causing a chemical change or a biological change, a source of electromagnetic radiation, a source of an electric field, a source of RF energy or a source of acoustic energy.

23. The device of claim 1 further comprising a transmitter, receiver or transceiver.

24. The device of claim 1 further comprising at least one coil, wherein said at least one coil is a near-field communication coil.

25. The device of claim 1, wherein said colorimetic indicator changes color in response to an analyte in said biofluid.

26. The device of claim 25, wherein said colorimetric indicator is embedded in a matrix material selected from the group consisting of filter paper, polyhydroxyethylmethacrylate hydrogel (pHEMA), agarose gel, sol-gel and combinations thereof.

27. The device of claim 25, wherein said colorimetric indicator comprises:
    a cobalt dichloride salt;
    a chemical selected from the group consisting of glucose oxidase, peroxidase, potassium iodide and combinations thereof;
    a chemical selected from lactate dehydrogenase, diaphorase, formazan dyes and combinations thereof;
    a 2,4,6-tris(2-pyridiyl)-s-triazine (TPTZ) complexed with mercury ion or iron ion;
    a 1,10-phenanthroline; or
    a universal pH indicator.

28. The device of claim 1, wherein the device is a skin-mounted sensor and said skin-mounted sensor quantitatively and/or qualitatively monitors said biofluid of a subject.

29. The device of claim 1, wherein the device has a modulus and a thickness within a factor of 2 of a modulus and a thickness of an epidermal layer of the skin of a subject.

30. The device of claim 1, wherein the device has an average modulus less than or equal to 500 kPa.

31. The device of claim 1, wherein the device has a net bending stiffness less than or equal to 1 nN m.

32. The device of claim 1, wherein the device has a footprint selected from a range of 300 $mm^2$ to 2000 $cm^2$.

33. A method for monitoring a biofluid that is sweat comprising:
    providing the device of claim 1, wherein the functional substrate is mechanically matched to skin;
    applying said device to the skin of a subject; and
    obtaining data from said at least one sensor; wherein said data provide quantitative and/or qualitative information about said sweat of said subject.

34. The method of claim 33, wherein the device further comprises a component for extracting interstitial fluid or blood from a subject.

35. The device of claim 1, wherein at least one of said plurality of sensors is configured to provide a sweat rate.

36. The device of claim 1, comprising four sensors for detecting four sweat biomarkers, wherein:
    a first sensor detects glucose;
    a second sensor detects lactate;
    a third sensor detects chloride; and
    a fourth sensor detects pH.

37. The device of claim 1, wherein said sweat volume channel includes a color changing compound disposed along the length of said sweat volume channel, the color changing compound being configured to change color upon contacting sweat to facilitate visualization of said distance traveled by sweat from said first end along said channel.

38. The device of claim 37, wherein said color changing compound is contained in a hydrogel matrix disposed on an inner surface of said sweat volume channel.

39. The device of claim 1, wherein said sweat volume channel has an orbicular shape.

40. The device of claim 1, wherein said sweat volume channel has a serpentine orbicular shape.

* * * * *